United States Patent
Krawczyk et al.

(10) Patent No.: US 11,225,756 B2
(45) Date of Patent: Jan. 18, 2022

(54) METHOD FOR PRODUCING LOW MOLECULAR WEIGHT AROMATIC LIGNIN-DERIVED COMPOUNDS

(71) Applicant: CMBLU PROJEKT AG, Alzenau (DE)

(72) Inventors: Nastaran Krawczyk, Gießen (DE); Alexander Moeller, Gießen (DE); Peter Geigle, Alzenau (DE)

(73) Assignee: CMBLU PROJEKT AG, Alzenau (DE)

( * ) Notice: Subject to any disclaimer, the term of this patent is extended or adjusted under 35 U.S.C. 154(b) by 238 days.

(21) Appl. No.: 16/091,437

(22) PCT Filed: Apr. 7, 2017

(86) PCT No.: PCT/EP2017/000462
§ 371 (c)(1),
(2) Date: Oct. 4, 2018

(87) PCT Pub. No.: WO2017/174207
PCT Pub. Date: Oct. 12, 2017

(65) Prior Publication Data
US 2019/0085006 A1 Mar. 21, 2019

(30) Foreign Application Priority Data

Apr. 7, 2016 (WO) .................. PCT/EP2016/000575
Feb. 13, 2017 (WO) .................. PCT/EP2017/000198

(51) Int. Cl.
| | |
|---|---|
| *D21C 11/00* | (2006.01) |
| *C08H 8/00* | (2010.01) |
| *E05F 5/12* | (2006.01) |
| *C10G 27/00* | (2006.01) |
| *C10G 1/08* | (2006.01) |
| *C10G 1/00* | (2006.01) |
| *E05F 3/22* | (2006.01) |

(Continued)

(52) U.S. Cl.
CPC ........ *D21C 11/0007* (2013.01); *C07C 303/06* (2013.01); *C07C 309/43* (2013.01); *C07C 309/46* (2013.01); *C07G 1/00* (2013.01); *C08H 8/00* (2013.01); *C10G 1/00* (2013.01); *C10G 1/08* (2013.01); *C10G 3/42* (2013.01); *C10G 15/08* (2013.01); *C10G 27/00* (2013.01); *C10G 29/00* (2013.01); *D21C 11/0042* (2013.01); *D21C 11/0057* (2013.01); *D21H 11/04* (2013.01); *D21H 11/06* (2013.01); *D21H 17/12* (2013.01); *D21H 17/74* (2013.01); *E05F 3/223* (2013.01); *E05F 5/12* (2013.01); *H01M 8/188* (2013.01); *B01D 61/027* (2013.01); *B01D 61/145* (2013.01); *B01D 2257/70* (2013.01); *C07C 303/44* (2013.01); *C07C 2602/10* (2017.05); *C07C 2603/24* (2017.05); *C07C 2603/26* (2017.05); *C10G 2300/1011* (2013.01); *C10G 2300/1014* (2013.01); *C10G 2400/30* (2013.01); *D21D 5/18* (2013.01); *E05F 2003/228* (2013.01); *E05Y 2201/638* (2013.01); *H01M 2300/0011* (2013.01)

(58) Field of Classification Search
CPC .................... D21C 11/0007; D21C 11/00057
See application file for complete search history.

(56) References Cited

U.S. PATENT DOCUMENTS

| | | | |
|---|---|---|---|
| 1,916,627 A | 7/1933 | Mersch | |
| 1,963,383 A | 6/1934 | Rogers | |

(Continued)

FOREIGN PATENT DOCUMENTS

| | | | |
|---|---|---|---|
| CN | 102040483 A | 5/2011 | |
| CN | 103000924 A | 3/2013 | |

(Continued)

OTHER PUBLICATIONS

SMOOK, Handbook for Pulp and Paper Technologists, 1992, Angus Wilde Publications, 2nd edition, chapters 7 and 8 (Year: 1992).*

(Continued)

*Primary Examiner* — Anthony Calandra
(74) *Attorney, Agent, or Firm* — Harness Dickey & Pierce P.L.C.

(57) ABSTRACT

The present invention relates to a method for producing one or more low molecular weight aromatic lignin-derived compounds. The method preferably comprises providing lignocellulosic material, subjecting the lignocellulosic material to a pulping process, separating pulp to provide a substantially pulp-free process stream comprising a modified lignin-derived component, isolating the modified lignin-derived component, subjecting the isolated modified lignin-derived component to a decomposition step comprising oxidative cracking (cracking and oxidizing) or reducing under the influence of a catalyst or electro-oxidation, and subjecting the resulting products to an isolation step, to provide a low molecular weight aromatic lignin-derived compound. Said compound may be further modified, e.g. by annulation. The inventive method preferably comprises further oxidizing said compound to a redox active compound. Additionally, the present invention relates to compounds obtainable by the inventive method and to an assembly for carrying out the inventive method. Furthermore, the present invention refers to a method for providing an existing pulp and/or paper manufacturing plant with said assembly.

27 Claims, No Drawings

(51) Int. Cl.

| | | |
|---|---|---|
| C10G 15/08 | (2006.01) | |
| C10G 29/00 | (2006.01) | |
| C10G 3/00 | (2006.01) | |
| C07G 1/00 | (2011.01) | |
| D21H 11/04 | (2006.01) | |
| D21H 11/06 | (2006.01) | |
| D21H 17/12 | (2006.01) | |
| D21H 17/00 | (2006.01) | |
| C07C 303/06 | (2006.01) | |
| C07C 309/43 | (2006.01) | |
| C07C 309/46 | (2006.01) | |
| H01M 8/18 | (2006.01) | |
| B01D 61/02 | (2006.01) | |
| B01D 61/14 | (2006.01) | |
| D21D 5/18 | (2006.01) | |
| C07C 303/44 | (2006.01) | |

(56) References Cited

U.S. PATENT DOCUMENTS

| | | |
|---|---|---|
| 3,646,071 A | 2/1972 | Frey et al. |
| 4,124,606 A | 11/1978 | Anello et al. |
| 4,420,644 A | 12/1983 | Huibers et al. |
| 5,002,634 A | 3/1991 | Dimmel et al. |
| 5,723,675 A | 3/1998 | Joo et al. |
| 5,944,953 A | 8/1999 | Lavoie et al. |
| 11,008,284 B2 | 5/2021 | Krawczyk et al. |
| 2004/0244925 A1 | 12/2004 | Tarasenko |
| 2010/0086675 A1 | 4/2010 | Berta et al. |
| 2011/0144337 A1 | 6/2011 | Santhosh et al. |
| 2011/0268652 A1 | 11/2011 | Machhammer et al. |
| 2013/0116424 A1 | 5/2013 | Peterson et al. |
| 2013/0232852 A1 | 9/2013 | Peterson et al. |
| 2013/0232853 A1 | 9/2013 | Peterson et al. |
| 2016/0009621 A1* | 1/2016 | Blair ............... B01J 23/002 562/475 |
| 2016/0013497 A1 | 1/2016 | Jones et al. |
| 2016/0032525 A1* | 2/2016 | Kurple ............ D21C 11/0007 162/16 |
| 2016/0130752 A1* | 5/2016 | Stigsson ............. C08H 6/00 162/16 |
| 2016/0197371 A1 | 7/2016 | Takechi |
| 2018/0079721 A1 | 3/2018 | Armand et al. |
| 2018/0097249 A1 | 4/2018 | Narayan et al. |
| 2018/0099917 A1 | 4/2018 | Anthony et al. |
| 2019/0390405 A1 | 12/2019 | Geigle et al. |
| 2019/0393506 A1 | 12/2019 | Hartwig et al. |
| 2020/0283380 A1 | 9/2020 | Krawczyk et al. |
| 2021/0020943 A1 | 1/2021 | Hartwig et al. |

FOREIGN PATENT DOCUMENTS

| | | |
|---|---|---|
| FR | 3030561 A1 | 6/2016 |
| GB | 1502275 A | 3/1978 |
| JP | S51100064 A | 9/1976 |
| JP | S51138666 A | 11/1976 |
| JP | S52144662 A | 12/1977 |
| JP | H9227499 A | 9/1997 |
| JP | 2001507404 A | 6/2001 |
| JP | 3813864 B2 | 8/2006 |
| JP | 2011057636 A | 3/2011 |
| JP | 2013254685 A | 12/2013 |
| JP | 2015534708 A | 12/2015 |
| JP | 2019503619 A | 2/2019 |
| JP | 2019513831 A | 5/2019 |
| KR | 20150004218 U | 11/2015 |
| RO | 76126 A2 | 5/1981 |
| SU | 1129204 A1 | 12/1984 |
| WO | 1998/013538 A1 | 4/1998 |
| WO | 2009083940 A2 | 7/2009 |
| WO | 2011131959 A1 | 10/2011 |
| WO | 2014052682 A2 | 4/2014 |
| WO | 2014081235 A1 | 5/2014 |
| WO | WO-2014/0081235 A1 | 5/2014 |
| WO | 2014204985 A1 | 12/2014 |
| WO | 2015048550 A1 | 4/2015 |
| WO | 2015148357 A1 | 10/2015 |
| WO | 2017174098 A1 | 10/2017 |
| WO | 2017174207 A1 | 10/2017 |
| WO | WO-2017/0174206 A1 | 10/2017 |
| WO | 2018146341 A1 | 8/2018 |
| WO | WO-2018/0146343 A1 | 8/2018 |

OTHER PUBLICATIONS www.chem.uiuc.edu, Oxidation of phenols, 1999 [downloaded online Nov. 20, 2020], (Year: 1999).*
Evgenii T Denisov and D I Metelitsa, 1968, Russ. Chem. Rev. 37 656 (Year: 1968).*
SMOOK, Handbook for Pulp and Paper Technologists, 1992, Angus Wilde Publications, 2nd edition, chapter 6. (Year: 1992).*
Klen et al., Lignin depolymerization over Ni/C catalyst in methanol, a continuation: effect of substrate and catalyst loading, 2015, Catal. Sci. Technol.,5, 3242. (Year: 2015).*
Kaiho et al., Construction of the di(trimethylolpropane) cross linkage and the phenylnaphthalene structure coupled with selective β-O-4 bond cleavage for synthesizing lignin-based epoxy resins with a glass transition temperature, Sep. 16, 2016, Green Chem., 18, pg. 6526 (Year: 2012).*
Hu L., et al., "Methods to Improve Lignin's Reactivity as a Phenol Substitute and as Replacement for Other Phenolic Compounds: A Brief Review," Bio Resources, 6(3): 3515-3525 (2011).
Huber G. W. et al., "Synthesis of transportation fuels from biomass: chemistry, catalysts, and engineering," Chem. Rev., 106(9): 4044-4098 (2006).
International Search Report issued in PCT/EP2017/000461 dated Dec. 6, 2017.
International Search Report issued in PCT/EP2017/000462 dated Sep. 6, 2017.
Moodley B. et al., "The electro-oxidation of lignin in Sappi Saiccor dissolving pulp mill effluent," (Jan. 1, 2011), HTTP://www.scielo.org.za/pdf/wsa/v37n1/v37n1a06.pdf, retrieved May 29, 2017.
Vandenberghe A., and Willems J.F., "Sulphonation of Alkylhydroquinones," Bull. Soc. Chim. Belges, 74(9-10): 397-406 (1965).
Written Opinion issued in PCT/EP2017/000461 dated Dec. 6, 2017.
Written Opinion issued in PCT/EP2017/000462 dated Sep. 6, 2017.
Xu, C. et al., "Lignin depolymerisation strategies: towards valuable chemicals and fuels," Chem. Soc. Rev., 43, 7485-7500 (2014).
Zakzeski J., et al., "The Catalytic Valorization of Lignin for the Production of Renewable Chemicals," Chem. Rev. 110, 3552-3599 (2010).
Office Action dated Mar. 20, 2020 issued in U.S. Appl. No. 16/091,436.
Office Action from corresponding Eurasian Patent Application No. 201892234 dated Sep. 10, 2019.
Azarov, V.I., "Khimiya drevesiny i sinteticheskikh polimerov," Sankt-Petersburg, pp. 366-373 (1999).
Brauns, F.E., "Khimiya lignina," Moscow, pp. 558-570 (1964).
U.S. Appl. No. 16/480,958, filed Jul. 25, 2019.
U.S. Appl. No. 16/480,956, filed Jul. 25, 2019.
U.S. Appl. No. 16/484,301, filed Aug. 7, 2019.
U.S. Appl. No. 16/968,732, filed Aug. 10, 2020.
International Search Report from PCT Application No. PCT/EP2018/053595 dated Jun. 12, 2018.
Written Opinion from PCT Application No. PCT/EP2018/053595 dated Jun. 12, 2018.
Wedege et al., "Organic Redox Species in Aqueous Flow Batteries: Redox Potentials, Chemical Stability and Solubility," Scientific Reports, 6(1) (2016).
Written Opinion from PCT Application No. PCT/EP2018/053596 dated May 3, 2018.
International Search Report from PCT Application No. PCT/EP2018/053596 dated May 3, 2018.
International Search Report from PCT Application No. PCT/EP2018/053597 dated May 8, 2018.

(56) References Cited

OTHER PUBLICATIONS

Written Opinion from PCT Application No. PCT/EP2018/053597 dated May 8, 2018.
Nedege, K., et al., "Organic Redox Species in Aqueous Flow Batteries: Redox Potentials, Chemical Stabilitiy and Solubility," Scientific Reports, 6(1): 1-13 (2016).
International Search Report from PCT Application No. PCT/EP2019/053602 dated Apr. 3, 2019.
Written Opinion from PCT Application No. PCT/EP2019/053602 dated Apr. 3, 2019.
Smook, Gary A., "Handbook for Pulp and Paper Technologists," Angus Wilde Publications, 2nd edition, chapters 7 and 3 (1992).
Denisov, E.T., and Metelitsa, D.I., "Oxidation of Benzene," Russ. Chem. Rev., 37 (656), 1968.
www.chem.uiuc.edu, "Oxidation of Phenols," (1999).
Dominguez-Ramos, A., et al., "Electrochemical Oxidation of Lignosulfonate: Total Organic Carbon Oxidation Kinetics," Ind. Eng. Chem. Res., 47(24): 9848-9853 (2008).
Duval, A., et al., "Fractionation of lignosulfonates: comparison of ultrafiltration and ethanol solubility to obtain a set of fractions with distinct properties," Holzforschung, 69(2): 127-134 (2015).
Gierer, J., "Chemistry of delignification, Part 1: General concept and reactions during pulping," Wood Science and Technology, 19: 289-312 (1985).
Gierer, J., "Chemistry of delignification: Part 2: Reactions of lignins during bleaching," Wood Science and Technology, 20: 1-33 (1986).
Miyazawa, T., et al., "Highly regioselective propanoylation of dihydroxybenzenes mediated by Candida antarctica ipase B in organic solvents," Tetrahedron Letters, 49: 175-178 (2008).
Weatherbee, C., et al., "A New Approach to Tertiary b-Chloroalkylamines. Synthesis of b-Chloroalkylaminomethylhydroquinonesl", Journal of Organic Chemistry, 21(10): 1138-1141 (1956).
Zhang, S., et al., "An Organic Electroactive Material for Flow Batteries," Electrochimica Acta, 190: 737-743 (2016).
Weetall, H. H., et al., "Biotechnology and Bioengineering—A Direct Fuel Cell for the Production of Electricity from Lignin," vol. 27, No. 7, pp. 1-11 (1985).
Mark, H. B., and Atkin, C. L., "Electrode Reactions of Aromatica Compounds in Strong Acid Solutions," Analytical Chemistry, 36(3): 514-520 (1964).
Arai, G., and Onozuka, M., "The Reaction of 1, 4-Naphthoquinone-2-sulfonate with Sodium Sulfite," The Chemical Society of Japan, 12:1899-1903, (1981).
Office Action from corresponding U.S. Appl. No. 16/480,956 dated Aug. 17, 2021.
Office Action from corresponding U.S. Appl. No. 16/480,958 dated Aug. 23, 2021.

* cited by examiner

METHOD FOR PRODUCING LOW MOLECULAR WEIGHT AROMATIC LIGNIN-DERIVED COMPOUNDS

The present invention relates to the field of valorizing lignin-comprising material, typically a by-product of pulping processes. The present invention provides a method for producing low molecular weight aromatic lignin-derived compounds. The inventive method comprises the steps of providing modified lignin-derived components obtainable from a pulping process and subjecting the same to a decomposition step comprising oxidative cracking (cracking and oxidizing) or reductive cracking (cracking and reducing) by means of a catalyst or by electrooxidation. After purification and optional annulation, the obtained low molecular weight aromatic lignin-derived compound is preferably further oxidized to a redox active compound, such as a monocyclic or bicyclic hydroquinone and/or quinone compound, and optionally further derivatized. Moreover, the present invention relates to compounds obtainable by the inventive method, to an assembly for carrying out the inventive method, and to a method to implement said assembly in a state-of-the-art pulp and/or paper manufacturing plant.

Lignin is among the most abundant naturally occurring organic materials together with cellulose and chitin (Sitte et al. 2002; S. 353-356). In total, lignin constitutes about 30% of non-fossil organic carbon and 20-35% of the dry mass of wood (W. Boerjan et al. (2003). "Lignin biosynthesis". Ann. Rev. Plant Biol. 54 (1): 519-549). Generally, the term "lignin" denominates phenolic macromolecules, which are composed of different monomeric building blocks. They are rigid biopolymers, which are part of plant cell walls and cause lignification of plant cells. About 20-30% of the dry mass of plants consists of lignin. It fills the volume in the cell wall established by cellulose, hemicellulose, and pectin components, particularly in xylem tracheids. Typically, lignin is covalently linked to hemicellulose and, therefore, crosslinks plant polysaccharides, conferring mechanical strength to the cell wall and, thus, to the plant as a whole (Chabannes, M.; et al. (2001). "In situ analysis of lignins in transgenic tobacco reveals a differential impact of individual transformations on the spatial patterns of lignin deposition at the cellular and subcellular levels". Plant J. 28 (3): 271-282). Therefore, height increment of plants requires lignin.

About 50% of the wood consumed on a global scale is used to produce timber-framed constructions and various pulp and/or paper products (Gellerstedt, G., 2009. The worldwide wood resource, in: Ek, M., Gellerstedt, G., Henriksson, G., (Eds.), Pulp and paper chemistry and technology, Volume 1, Wood chemistry and wood biotechnology. Walter de Gruyter, Berlin, Germany). The dominant method for producing (paper) pulp are various chemical pulping processes, among which the Kraft pulping process (in short "Kraft process") is the most frequently applied process. Even although applied on a smaller scale only, the sulfite pulping process (commonly designated as "sulfite process") is of economic relevance as well. Both generate a variety of modified lignin-derived molecules, such as Kraft lignin or lignosulfonate, as by-products of the pulping process. In addition, other processes in the art, e.g., "soda pulping" which generates soda lignin, or processes involving organic solvents, such as "organosolv", are established as well. They are, however, of minor relevance in practice. Even less, are other pulping processes, such as the "steam explosion process", the "ammonia fiber explosion process" and the "hot water process".

Any chemical pulping applied aims to dissolve and remove lignin and hemicellulose and to liberate wood cellulose fibers. Typically, (some) hemicellulose is also degraded in the process (Brannvall, 2009 Overview of pulp and paper processes, in: Ek, M., Gellerstedt, G., Henriksson, G., (Eds.), Pulp and paper chemistry and technology, Volume 2, Pulping chemistry and technology. Walter de Gruyter, Berlin, Germany). Currently, about 70 million tons of lignin and/or lignin derivatives are produced world-wide by the Kraft process, which accounts for over 80% of the total amount of produced lignin. Sulfite pulping by the sulfite process pre-dates the Kraft process, but has largely been replaced by the Kraft process due to increased cellulose fiber strength resulting from the Kraft process.

Currently, about 99% of the modified lignin material provided by the Kraft or the sulfite process are passed to combustion units, usually combustion units installed at the site of the pulp and/or paper manufacturing plant. The resulting heat is used as the plant's internal energy source. Heat released from burning lignin and/or lignin derivatives is used for steam and power generation, typically rendering the respective plant energetically autonomous.

However, lignin oversupply is a common phenomenon, e.g., in state-of-the-art Kraft pulping plants, as such plants have become more energy efficient. Meanwhile, less lignin is required as energy source to operate such a plant (J. Lora, 2008. Industrial commercial lignins: sources, properties and applications, in: Belgacem, M. N., Gandini, A., (Eds.), Monomers, polymers and composites from Renewable Resources. Elsevier, Amsterdam.). It is expected that this trend will continue in the future.

To reduce lignin oversupply, genetically modified plants made of wood with reduced lignin contents were envisaged and tested. However, it was found that environmental conditions have a larger impact on the lignin content than the genetic modifications tested (E. L. Tilstona, et al., Genetic modifications to lignin biosynthesis in field-grown poplar trees have inconsistent effects on the rate of woody trunk decomposition. Soil Biology and Biochemistry 36 (11), November 2004; S. 1903-1906). For this and other reasons, genetic modifications generating plants of lower lignin contents are not to be expected to reduce organic lignin production, such that lignin is expected to continue to be an abundant by-product of pulp and/or paper production. Oversupply of lignin may even be fostered, as biorefineries (converting cellulosic biomass into liquid fuels) will generate substantially more lignin as by-product than what may be consumed by local consumption units (A. J. Ragauskas et al., Lignin Valorization: Improving Lignin Processing in the Biorefinery Science, 16 May 2014: Vol. 344, Issue 6185, pp.).

Lignin material typically obtained as by-product of the pulping processes, for example, Kraft lignin or lignosulfonate is composed of numerous complex lignin derivatives. Typically, "lignosulfonates" are yielded from the pulping liquor of the sulfite process (sulfite pulping), or may be produced by so-called postsulfonation of lignin-derived polymers obtained by the Kraft process (sulfate pulping).

Currently, modified lignin-derived components, such as lignosulfonates, are primarily employed as dispersants and binders in construction, mining and agricultural industries. The largest dispersant use of lignosulfonates is its admixture for concrete, while copper mining, carbon black and coal represent its most prominent applications as binder. Demand in downstream markets is greatly influenced by the overall economic. Consumption of lignosulfonates is predicted by some experts to grow moderately at an average annual rate of about 2.5% until end of 2016. However, competing products are likely to reduce lignosulfonate's demand. Consequently, it may be expected that the overall supply of lignosulfonate will further rise as a function of increasing amounts of modified lignin derivatives resulting from the ever growing paper manufacturing industry and more efficient pulp and/or paper manufacturing plants.

Hence, conversion of excess unmodified polymeric lignin resulting from, for example, pulp and/or paper production may be a source, for the provision of value-added material. Such an approach is a demanding field of research. In this regard, it is the object of the present invention to provide a method for production of value-added material starting from (un)modified polymeric lignin.

This object is solved by the claimed subject matter. Particularly, the object underlying the present invention is solved according to a first aspect by the method of claim 1 comprising preferably steps (A) to (F). By a second aspect, the present invention refers to low molecular weight lignin derived compounds, which are obtainable by a method according to the first aspect. By a third aspect, the present invention is directed to an assembly, which allows to carry out steps (C) to (F) of the inventive method.

By its first aspect, the present invention is directed to a method for producing at least one low molecular weight aromatic lignin-derived compound, wherein the method comprises the provision of lignocellulosic material (step A). The lignocellulosic material is preferably chopped. Such material is subjected to a pulping process in subsequent step (B). In step (C), the pulp obtained in step (B) is separated in a pulp separating step from the process stream obtainable from the pulping process in step (B), to provide a substantially pulp-free process stream. That substantially pulp-free process stream comprises modified lignin-derived components, hemicellulose, inorganic material, such as reactive agents. Therein, the essentially pulp-free process stream, which contains the modified lignin-derived components, may be provided as one single process stream or may be partitioned in at least two (partial) process streams. By subsequent method step (D), the fraction of modified lignin-derived components comprised either (alternative D.1) in the process stream provided by step (C) or (alternative D.2) in at least one of the at least two (partial) process streams provided by step (C) is isolated from the process stream(s) and its/their other components (e.g. hemicellulose and/or hydrolysis products thereof).

Thereafter, the isolated fraction of modified lignin-derived components of step (D) is subjected to chemical decomposition by step (E), wherein chemical decomposition step (E) may be carried out by either (alternative E.1) oxidative cracking (cracking and oxidizing) of the modified lignin-derived components in the presence of a homogeneous catalyst comprising a metal or a metalloid component. The terms "oxidative cracking (cracking and oxidizing)" and "cracking and oxidizing" may be used interchangeably herein. Alternatively, chemical decomposition step (E) may be enabled (by alternative E.2) by reductive cracking (cracking and reducing) of the modified lignin-derived components in the presence of a heterogeneous catalyst comprising a metal or a metalloid component. The terms "reductive cracking (cracking and reducing)" and "cracking and reducing" may be used interchangeably herein. Finally, (by alternative E.3) the modified lignin-derived components may be subjected to electrooxidation, preferably in alkaline or acidic solution. The inventive method is characterized by its final step (F), wherein the resulting lignin-derived products provided by step (E) are subjected to an isolation step. Hereby, the target compounds, i.e. low molecular weight aromatic lignin-derived compounds, may be purified by isolation from, e.g., higher molecular weight aromatic lignin components and/or preferably from other non-lignin-derived residual components, including e.g. inorganic reactive agents.

Thus, the present invention is based on the unprecedented combination of state-of-the-art large-scale pulp and/or paper manufacturing processes as source of enormous quantities of modified lignin-derived components representing by-products of such processes. The inventive method comprises conversion or decomposition of said modified lignin-derived components (as by-products of the pulping process (step (B)) to low molecular weight lignin-derived compounds and their subsequent isolation, i.e. by a purification step from residual material. Said method yields low molecular lignin-derived compounds, preferably low molecular weight aromatic lignin-derived compounds. They are preferably of low polydispersity due to the method's final purification step (F). By said inventive combination, established process steps in pulp and/or paper production may precede the steps of converting the initial lignin-derived material to at least one low molecular weight aromatic lignin-derived compound. By applying state-of-the-art chemistry, such compounds may subsequently be further modified and/or derivatized. Consequently, the inventive method combines two separate processes, i.e. by using by-products of a pulping process as starting material for subsequent generation of low molecular weight aromatic lignin-derived compounds. Thereby, energy consumption may be reduced and renewable resources may advantageously be employed to provide (ideally within an integrated plant) low molecular weight aromatic lignin-derived compounds. These compounds may serve as precursors for the production of, e.g., redox active compounds, which were previously (economically) amenable by non-renewable sources only (e.g. as by petrochemical methods).

Hence, the present invention provides a method for the production of at least one low molecular weight aromatic lignin-derived compound, preferably of low polydispersity. Said low polydispersity may essentially be achieved by at least one isolation step (F), e.g. by filtration or extraction, to isolate the desired modified lignin-derived products resulting from decomposition in step (E). Thereby, the method of the present invention provides chemically well-defined organic compounds, i.e. specialty materials. In particular, they may be subject to further derivatization, e.g., to redox active compounds according to preferred embodiments of the present invention. As such, the present invention refers to an inventive method allowing to provide products resulting from reaction steps (A) to (F) and, optionally, from further downstream steps. The method uses a renewable and abundant source of lignocellulosic material as starting material. Typically, the product resulting from reaction steps (A) to (F) is by itself commercially exploitable. Optionally, the product resulting from step (F) is further derivatized to produce compounds of characteristic nature, e.g. redox active compounds, which may be advantageously and versatilely used.

"Lignin" is generally understood herein as wood-derived heterogeneous phenolic macromolecule or, rather, a group of phenolic macromolecules of plant origin, which is or are composed of different monomeric building blocks. Hence, it is understood to be a natural copolymer. More specifically, lignin may be generally defined as an amorphous three-dimensional polymer, which is mainly and naturally composed of phenolic building blocks. Lignin in its "native" state, i.e. as part of the natural lignocellulosic material, is the starting material of the inventive method for any "modified lignin" and, subsequently, any "lignin-derived" target compound as described herein as product of the inventive methods.

Lignin typically comprises p-coumaryl, coniferyl and sinapyl alcohol as the phenolic building blocks, which are linked (randomly) with ether (C—O—C) bonds, such as "β-O-4", "4-O-5" and, to a less frequent extent, "1-O-4". The most frequently seen covalent linkage in natural softwood and hardwood lignin is typically the "β-O-4" bond, which accounts, e.g., for approximately 45-50% of all bonds in spruce and up to 60% in birch. Additionally, carbon-carbon (C—C) linkages may occur in natural lignin, such as "5-5", "β-5", "β-β" and "β-1", amongst which the "5-5" linkage is most frequently seen C—C linkage, in particular in softwood, such as spruce. Typical linkages as "β-O-4", "4-O-5" and "5-5" are depicted in the following:

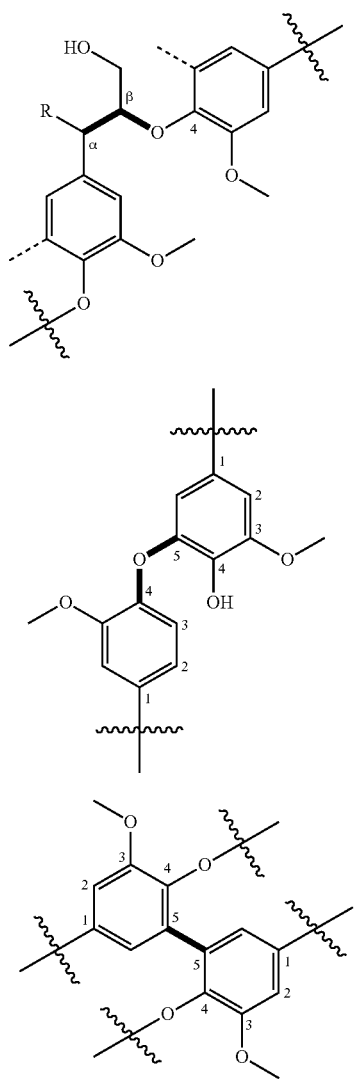

A "building block" as used herein may preferably be understood as an organic moiety, which comprises at least one bond to covalently link said building block to another building block of the same or different chemical structure to form a plurality of covalently associated building blocks.

Preferably, a building block according to the present invention is a "phenolic building block", i.e. any moiety comprising a six-membered aromatic ring, covalently functionalized by at least one hydroxyl group (—OH). Hence, the lignin "building block" is typically characterized by a monocyclic, typically an aromatic moiety, with the monocycle typically being substituted at at least one position. Typically, each lignin building block exhibits a carbocyclic monocycle with one or two substituents acting as linkers to another building block and one or two substituents, which do not exhibit any linking function. A building block in the context of the present invention corresponds to a "monomer". A "dimer" as used herein typically comprises two such building blocks covalently linked. Thus, the dimer is typically characterized by two isolated monocyclic moieties covalently linked by a linker group or by a bond (biphenylic ring system). Biphenylic ring systems (as characteristic moiety of dimers) occur with lower frequency in plant lignin, in some plants (e.g. in spruce) with higher frequency. More generally, any such dimeric compounds belong to the class of bicycles.

A larger plurality of any such covalently connected or linked building blocks forms typically the larger 3-dimensional lignin structure. In the context of the present invention, a "polymer" refers to a natural lignin molecule as it occurs in plants, e.g. as part of lignocellulosic material. The lignin polymer is typically a copolymer of distinct building blocks. Natural lignin's "building block" corresponds to a "monomer". Accordingly, a building block typically is a (repeating) structural part of the natural polymer lignin. The (phenolic) building block has typically 9 carbon atoms ($C_9$) or, less frequently seen, 8 carbon atoms ($C_8$). Typically, the building blocks have a molecular weight of about 130 to 300 Da, preferably of 150 to 250 Da, more preferably of 160 to 190 Da. Preferably, their basic monomeric $C_9$ or $C_a$ structure is not altered in the course of the natural lignin modifying process by e.g. pulping.

As a derivative of natural lignin, the "modified lignin-derived component" is a lignin molecule, which underwent a pulping process, such as "Kraft lignin" or "lignosulfonate". A "modified lignin-derived component" typically has a lower molecular weight than natural lignin, from which it is derived. However, the "modified lignin-derived component" is larger than the monomeric or dimeric target compound, preferably having a molecular weight of at least 1.000 Da. The nature (and the actual molecular weight) of the "modified lignin-derived component" may vary largely depending, e.g., on the starting material, on the (pulping) method, by which the modified lignin-derived component is obtained, and on the reaction conditions applied by the inventive method. However, it is common to the modified lignin-derived components that they are composed of $C_8$ or $C_9$ building blocks after, e.g., a pulping process, as they occur in natural lignin.

It follows from natural lignin's complex and somewhat random chemical structure that lignin-derived components, such as products of the pulping process, are typically heterogeneous. The pulping process provides a larger variety of lignin-derived components, which may typically contain from 8 to 150 building blocks. Moreover, lignin-derived components of the same number of building blocks are also diverse in terms of their chemical nature, as they reflect individual portions of the heterogeneous natural lignin polymer. That chemical and structural heterogeneity of lignin-derived material obtained from e.g. the pulping process traditionally impeded the preparation of homogeneous and/or high quality products by prior art methods, such that adequate economic exploitation of lignin-derived material was difficult to achieve in the art. That prior art issue is overcome by the inventive method.

Pulping processes, nevertheless, typically yield "modified" lignin-derived components based on $C_8$ or $C_9$ building blocks, wherein some or all of the building blocks may be modified. Modifications preferably occur at the linking groups of those building blocks of natural lignin, which are dissociated by the pulping process, and/or at substitution sites of the building blocks, in particular at the aromatic ring system of a building block, e.g. by side chain modification or e.g. by sulfonation. Accordingly, the molecular weight of the modified building blocks of lignin-derived components may typically be slightly higher than the molecular weight of the building blocks of the natural lignin polymer.

The method according to a first aspect of the present invention comprises by its step (A) the provision of lignocellulosic material of plant origin as starting material. "Lignocellulosic material", understood to be the starting material for the method of the present invention, may be provided as any form of plant biomass, which naturally comprises cellulose, lignin and hemicellulose. Therein, cellulose (a polysaccharide consisting of a linear chain of several hundred to many thousands of β(1→4) linked D-glucose units) typically forms a scaffold of fibers together with hemicellulose. Lignin is typically embedded within this scaffold, typically without being covalently linked to cellulose and/or hemicellulose. "Hemicellulose" is any of several heteropolymeric polysaccharides, which include xylan, glucuronoxylan, arabinoxylan, glucomannan, and xyloglucan. It is typically present along with cellulose in almost all plant cell walls. In contrast to cellulose, hemicellulose usually has a random, amorphous structure with little strength.

Said lignocellulosic material typically is the starting material for any pulping process with the object to obtain "pulp". "Pulp" is understood herein to essentially comprise a mixture of (preferably pure) cellulosic fibrous material, which does not contain lignin or lignin-derived components or contains only minor residual amounts of lignin components. Said lignocellulosic material may be derived from any appropriate plant origin, e.g. wood, fiber crops or waste paper origin. In case waste paper is used as starting material for the inventive method, such waste paper is typically of lower paper quality, such as newspaper paper. It usually comprises higher amounts of residual lignin, while higher quality paper is typically lignin-free. Field crop fiber or agricultural residues (instead of wood fiber) may be preferred as being of more sustainable nature. However, wood is the preferred renewable source, with about 90 percent of pulp originating from wood plantations or reforested areas. Non-wood fiber sources may be employed by the inventive method as well (as far as it is for global pulp production), for a variety of reasons, including seasonal availability, problems with chemical recovery, brightness of the pulp etc. Non-wood pulp processing, however, usually requires more water and energy than wood pulp pressing.

Lignocellulosic material of known and invariant character is preferred, such that the inventive method's downstream products remain essentially unaltered, preferably provided in the form of chopped lignocellulosic material, e.g. in the form of wood chips. "Chopped" lignocellulosic material is understood—by the present invention—to be advantageously mechanically processed starting from plant material of natural origin, such that it is chopped to smaller pieces. Said lignocellulosic material is typically processed by any form of grinding, crushing and/or milling, which results in smaller pieces of the lignocellulosic material, i.e. the chopped lignocellulosic material, which is preferred in the context of the present invention. It may be preferred to employ lignocellulosic material with a lignin content of at least 15%, more preferred of at least 20%, most preferred of 20 to 35%.

The lignocellulosic material according to the present invention is preferably provided in the form of woodchips. "Woodchips" are understood as a medium-sized solid material made by cutting, or chipping, larger pieces of wood. Characteristic values (such as water content, ash content, particle size distribution, bulk density, nitrogen content, chlorine content) are preferably chosen such that they fulfil generally accepted provisions, such as the European Standard EN 14961. Wood chips as typically used for chemical pulping processes are preferably used for the inventive method as well as they are usually relatively uniform in size and substantially free of bark. The optimum size may vary with the wood species. Preferred sizes of the main fraction are about 3 to 45 mm with a fine fraction, defined as particles below 1 mm, of preferably less than 5%. Common wood chips used in pulp production, which are preferred in the method of the present invention, are on average 12-25 mm (0.47-0.98 in) long and 2-10 mm (0.079-0.394 in) thick. Damage of the wood fibers is preferably avoided, as fibers free of physical defects are advantageous for the pulp properties. As the method of the present invention shares the same starting material as the pulping process, the starting material should satisfy the requirements of both the inventive method as a whole and the pulping process. For roundwood it is most common to use disk chippers. Therein, "roundwood" is understood as industrial roundwood, which is commonly defined, e.g., in the FAO Forest Products Yearbook to include all industrial wood (e.g. sawlogs and veneer logs, pulpwood and other industrial roundwood) and marketed forms, such as chips, particles or wood residues.

The inventive method comprises by its step (B) processing of the lignocellulosic (starting) material, which is preferably chopped, by a pulping process. A "pulping process" is understood in the context of the present invention as process of chemically and/or mechanically disjoining cellulose fibers from other constituents of the lignocellulosic starting material of the pulping process, such as any wood, fiber crops or waste paper. Said pulping process generally yields pulp. Pulp is—in contrast to a processes for the manufacturing of pulp—the by-product (reflecting the essentially cellulosic fraction) of the present inventive method. It may still comprise (minor) amounts of lignin or derivatives thereof as impurities of the cellulosic fibrous material.

Distinct pulping processes may be used as a matter of choice to provide feedstocks for obtaining the lignin-derived components intermediates of the method of the present invention. The pulping process separates the principle components of the lignocellulosic material, degrades the polymers to smaller compounds and occasionally causes other chemical transformation, depending from the method employed.

These employed pulping processes may preferably be those overly used in the pulp and paper industries (i.e., Kraft or sulfite process) or other processes such as organosolv. Each process type has its advantages and disadvantages. The choice of the employed pulping process as step (B) of the inventive method may depend on the type of lignin-derived components, which is envisaged as intermediate before decomposition and eventual further derivatization. The modified lignin-derived components obtainable as "by-product" of the chosen pulping process may be employed for further processing (e.g. derivatization) by downstream reactions of the inventive method. The choice of the pulping process may thereby determine the target compounds obtainable by the inventive method.

The Kraft process is by far the most prevalent pulping process worldwide. It is typically a high pH pulping process in aqueous solution (typically aqueous sodium hydroxide) containing one or more of salt or non-salt agents selected from sulfide, sulfhydryl and polysulfide. It usually further comprises a sulfate salt. Despite the sulfides employed, relatively little sulfur is typically contained in the product stream following pulping. The Kraft process is versatile in terms of the lignocellulosic starting material, which is treated in aqueous solution at elevated temperature and pressure. It is energy efficient and recycles most of the employed reactive agents, such as reactive agents required for the pulping process. Said process yields "Kraft lignin". Typically, the modified lignin-derived components (Kraft lignin) have a molecular weight of about 2.000 to 5.000 Da, preferably 2.000 to 3.000 Da. They may be components of the natural 3-D lignin polymers, potentially further chemically functionalized by the introduction of additional functional groups and linkages (e.g. stilbenes). The process chemistry surrounding Kraft process including a description of the ways in which lignin linkages are disrupted during the process are described in Chakar and Ragauskas Ind Crops Prod 2004, 20, 131. Gierer et al. (Wood Sci Technol. 1985, 19, 289 and Wood Sci Technol. 1986, 20, 1) describes the structural changes that occur to lignin as a result of chemical bleaching during the Kraft process.

Alternatively, the sulfite process may be employed, which is the second most prevalent pulping process worldwide. It is typically a low pH pulping process (although it may be conducted between pH 2 and 12) in aqueous solution containing one or more of salt or non-salt agents exhibiting one or more of sulfite or bisulfite groups or anions. For the sulfite process, the lignocellulosic starting material is treated in aqueous solution at elevated temperature and pressure. The process yields "lignosulfonate", which is typically soluble in water and in some highly polar organics and amines. Lignosulfonate is generally more water-soluble than "Kraft lignin". Sulfite pulping is generally less destructive than Kraft pulping, i.e. the natural lignin polymer is degraded to modified lignin-derived components being larger (and in particular exhibiting a higher average molecule weight and higher monomer molecular weights) than the corresponding components in Kraft pulping. Thus, "lignosulfonate" typically has a molecular weight of about 3.000 to 100.000 Da, preferably 5.000 to 20.000 Da.

As a further alternative, the "organosolv process is typically carried out by treatment of wood or bagasse with various organic solvents. "Bagasse" is the fibrous residue that remains once plant material (such as sugar cane) has been crushed and juice or sap have been extracted.

The "Alcell process" is one of the most well-known organosolv processes. It involves dissolution of lignin in either ethanol or ethanol/water mixtures. The advantage of the organosolv process is that it allows to automatically generate separate process streams of cellulose, hemicelluloses, and lignin. Thereby, all components of the lignocellulosic biomass starting material may be individually processed. That process is generally considered as environmentally attractive, as it does not employ aggressive reactive agents (e.g. sulfides) and harsh conditions used in the more common Kraft or sulfite processes. The organosolv process typically yields organosolv lignin as the modified lignin-derived components, which may be employed in further downstream reaction steps of the present invention. Organosolv lignin is typically low in sulfur content. It has a low molecular weight of about 1.000 to 2.000 Da. It is typically also of higher purity than the lignin-derived components obtained from other pulping processes. A disadvantage of the organosolv process are the costs of solvent recovery.

Another pulping process, which may be employed by the present invention, is the "steam explosion process involving steam impregnation under pressure followed by rapid pressure release, which separates the lignocellulosic constituents. Covalent linkages of 3D lignin are ruptured as well, such that a complex mixture of lignin derived fragments is obtained. Typically, wood or bagasse is exposed to steam at overpressure and elevated temperature, such as a total pressure of 1.38 to 3.45 MPa and a temperature from about 453 to 503 K for about 1-20 min before rapid pressure release. The molecular weight distribution of the lignin fragments obtained by the steam explosion process is typically similar to the organosolv process. In addition, the process uses no sulfur, and separating the process streams is also possible.

Pyrolysis of lignocellulosic material (as a further alternative of step (B)) generally leads to pyrolyzed lignin-derived fragments, which may also be considered as modified lignin-derived components to be employed by the present invention. The pyrolysis process typically involves relatively high temperatures, typically at least 600 K, such as between 720 and 750 K. No waste other than flue gas and ash is produced by that process, whereas increased energy consumption is required to fuel the process. Pyrolysis lignin exhibits structural characteristics significantly different from lignin components obtained from other "pulping processes. It involves $C_8$— rather than $C_9$ building blocks, potentially allowing for unique downstream reactions according to the present invention. Thereby, specific aromatic hydrocarbons are made available as target compounds, which are not available via other processes.

Several other methods for isolating (modified) lignin from wood or plant biomass or starting material are described in the art as well, including the "ammonia fiber explosion" (AFEX) process and the "hot water process", which may also be employed as step (B), and are described in further detail by Bozell et al. (Top Value Added Candidates from Biomass. Volume II: Results of Screening for Potential Candidates from Biorefinery: Lignin; Pacific Northwest National Laboratory: Richland, Wash., 2007) and Kamm et al. (Biorefineries—Industrial Processes and Products; VCH: Wcinheim, Germany, 2006; Vol. 2). Finally, the "dilute acid process" as a further option for step (B) of the inventive method may ensure effective separation of lignin from other biomass components. It may, however, provide lower yields. Corrosion of equipment (due to the acidic environment) may also be an issue. The "alkaline oxidation process" may use $O_2$ or $H_2O_2$ to degrade lignin. However, the process may suffer from slower delignification rates. The dilute acid process and alkaline oxidation process may both provide modified lignin-derived components with similar molecular weight (distributions) as organosolv lignin.

Further, the inventive method comprises by its step (C) the step of separating pulp obtained by step (B) from the process stream obtainable from step (B) (and, thereby, from the envisaged modified lignin-derived components) in a pulp separating step. Hereby, the process stream of step (B) is converted to (i) a substantially cellulose-free stream with enriched fractions of modified lignin-derived components, hemicellulose and/or fragments of any thereof, and (ii) pulp, which is understood herein to essentially comprise a mixture of (enriched) cellulose fibrous material. The pulp fraction may be separated by step (C) as dry matter or as a pulp containing stream. The pulp or pulp containing stream is further processed according to state-of-the-art technologies for, e.g., manufacturing paper. The stream(s) containing the fraction of modified lignin-derived components is subjected to step (D) of the inventive method.

As used herein, a "stream" or "process stream" is generally understood as a liquid medium comprising intermediates of the inventive method resulting from the preceding method step, which serve as starting (process) material for the subsequent method step. Generally, the stream includes its components dissolved, suspended or dispersed in said liquid medium. Distinct fractions of the (process) stream may be obtained reflecting components of homogenous nature, which may be isolated by fractionation from the process stream.

A "fraction" may represent a part of a whole or, more generally, any number of (equal) parts. In particular, a fraction is understood herein to be a part of a (process) stream according to the present invention, which typically comprises at least two different fractions.

Accordingly, different fractions may be organic matter comprising (residual) cellulosic material and non-cellulosic material such as modified lignin-derived components (e.g. Kraft lignin or lignosulfonate) and hemicelluloses. Further, fractions of a stream according to the present invention may be inorganic reactive agents, which are required to run the process, e.g. inorganic buffer salts. Another fraction, typically the largest both in terms of volume and mass, is the solvent/dispersant. The solvent usually is an aqueous solvent/dispersant from the pulping process, which may be diluted or concentrated in the steps following step (B), which is herein understood to form a part of the total dry mass carried in the stream according to the present invention. A particularly important fraction of the stream in the context of the present invention is the fraction of modified lignin-derived components.

As used herein, the term "lignin-derived material" has the broadest meaning with regard to any lignin, which underwent one or more process steps, from process step (B) onwards, according to the present invention. Therein, a "derived" material has to be understood as a chemical derivative according to the present invention. A lignin-derived material may be of any molecular weight smaller than the natural lignin polymer, including a small molecule, i.e. a low molecular weight compound as used herein. In this regard, both "modified lignin-derived components" and "lignin-derived compounds" according to the present invention are lignin-derived material.

A "modified lignin-derived component" has to be understood in the context of the present invention as a lignin molecule, which underwent a pulping process according to step (B) of the inventive method. Thereby, it may be modified with regard to, for example, molecular weight and/or solubility in water. Typically, intramolecular bonds such as ether bonds are broken up within the lignin. Thus, the macromolecule usually shrinks in size, i.e. in molecular weight. In contrast, a "native" lignin molecule starting material, i.e. a lignin, which is not (yet) modified by a pulping process, typically is larger than modified lignin-derived components. Additionally, or alternatively, hydrophilic groups such as sulfonate groups may be introduced into the lignin molecule. Hence, typical modified lignin-derived components are, for example, Kraft lignin and lignosulfonate, but also other lignin derivatives resulting from further pulping processes are comprised in the context of the present invention, such as organosolv lignin. These may be, for example, soda pulping, which is generating soda lignin, processes involving organic solvents such as organosolv providing organosolv lignin and even less frequent processes such as the steam explosion process or the ammonia fiber explosion process and the hot water process providing respective modified lignin. Hence, modified lignin-derived components are typically used herein to refer to lignin derivatives in contrast to a low molecular weight lignin-derived compound, which is a preferred product of the inventive method.

A (chemical) "derivative" is typically a compound that is derived from a similar compound by a chemical reaction. Thus, a derivative may be understood herein as a compound that can be imagined to arise from another compound, if one atom or group of atoms is replaced with another atom or group of atoms, or the term may be understood as a structural analog. The term "structural analogue" is generally common in organic chemistry.

Typically, "modified lignin-derived components" as used herein are present as a fraction of a (process) "stream". Such a stream may comprise residual or waste material and the solvent and/or dispersant from which the intermediate of interest is preferably isolated. Typically, the solvent and/or dispersant accounts for at least 50% (w/w) of the total weight of material forwarded as a "stream" to the next method step, or at least 60% (w/w), or at least 70% (w/w), or at least 80% (w/w), or at least 90% (w/w), or at least 95% (w/w). The solvent and/or dispersant is typically an aqueous medium, but may alternatively be an organic solvent, depending on the pulping process. Generally, the stream flows unidirectionally, from the preceding method step to the more downstream method steps. Valves, pumps and/or gravity-assisted means may typically be employed to facilitate the required flow of the stream downwards to the final step of the method of the present invention.

The inventive method comprises step (C) for separating the pulp from the process stream from the pulping step (B). Typically, upon pulping, the lignin in the lignocellulosic material is broken into smaller molecules, which are more soluble in the pulping liquid. Cellulose is degraded to a minor degree, although individual cellulose fibers may detach from the chopped lignocellulosic material during the pulping process and dissolve rather in the pulping liquid than natural lignin. As a consequence, a residual cellulosic scaffold remains. However, to a varying degree, cellulose fibers are also present in the liquid in dispersed form, i.e. not in the larger scaffold structure of fibers.

In step (C) of the inventive method, preferably both the scaffold and the dispersed cellulose fibers are separated from the process stream. A preferred embodiment of separating the cellulose which is present in the scaffolds, is "blowing" the cellulose scaffold of the chopped lignocellulosic material, which underwent the pulping of step (B), into a collection tank ("blow tank"). The residual cellulosic scaffolds may be blown into a blow tank that usually operates at atmospheric pressure. This blowing typically releases steam and volatiles. Volatiles are understood herein as organic chemicals that have a high vapor pressure at ordinary room temperature. Typically, they are characterized by an individual odor. The volatile fraction may be condensed and collected. When employing "northern softwoods" as the starting material for the present invention, the volatile fraction typically encompasses raw turpentine.

The pulp separation in step (C) may preferably further comprise to separating cellulose from the liquid, which was not blown out as part of the blown out residual cellulosic scaffold, e.g. the dispersed cellulose fibers. The pulp separation according to step (C) may encompass distinct sieves or screens and/or centrifugal separation. The sieves are typically arranged in a multistage cascade-like assembly. By such an arrangement, considerable amounts of pulp is preferably captured, and thus, separated from the process stream containing the fraction of interest according to the inventive method, i.e. the fraction of modified lignin-derived components.

The process stream (optionally subject to blowing, sieving and/or filtration) may also undergo one or more washing steps to separate pulp. Thereby, (residual) dispersed cellulose fibers are separated from the process stream. Usually, a pulp mill encompasses 3-5 washing stages in series. Pulp washing as used herein is typically carried out by pulp washers using counter-current flow in between two subsequent stages such that the pulp moves in the opposite direction to the flow of washing water. While the washing water becomes a part of the process stream comprising the target modified lignin according to the present invention, cellulose is effectively separated and ready for conventional use such as paper production. Various techniques may be involved in pulp washing, such as thickening/dilution, displacement and diffusion. The washing equipment may comprise, for example, pressure diffusers, atmospheric diffusers, vacuum drum washers, drum displacers and wash presses.

Said separation step or steps may provide a substantially pulp-free process stream as a result of step (C). Said pulp-free stream, which is herein forwarded for its further processing in step (D), is commonly designated as "black liquor" (due to its color), when applying the Kraft process or "brown liquor", when applying the sulfite process in step (B). It typically comprises modified lignin-derived components and random fragments thereof (i.e. lignin-derived molecules formed during the pulping process, but having a lower molecular weight than the typical modified lignin-derived components) and hydrolysis products of hemicellulose. Hemicellulose is typically hydrolyzed in any pulping process, e.g. in acidic or alkaline medium, yielding smaller pieces of hemicellulose such as poly- or oligosaccharide fragments or even mono- or disaccharides thereof, which are all usually dissolved in the pulping liquid and/or the process stream. Further, (in)organic salts as residual components of the reactive agents used for the pulping process may be comprised in the essentially pulp-free process stream, such as sodium carbonate and/or sodium sulfate.

By step (D) of the inventive method, the fraction of modified lignin-derived components is isolated from the above components of the essentially pulp-free process stream obtainable from step (C). The process stream of step (C) entering to step (D) may be provided by either one single stream (according to alternative D.1) or as at least two streams (according to alternative (D.2)).

By providing two or more (partial) streams (according to alternative D.2), it may be controlled, which amount of the modified lignin-derived components is further processed according to the inventive method. Hence, stream separation in alternative (D.2) is a tool to fine tune the inventive method when determining its flow rate and turnover of the process. By dividing the stream into two or more partial streams, supply of modified lignin-derived components either to downstream process steps (E) and (F) or its (conventional) use for combustion for energy supply (e.g. of the pulping plant) may be controlled as well.

By said dividing step, the sum of the flow rates of the partial streams is typically equal to the flow rate prior to the dividing step. The flow rate of each of the two or more partial streams may correspond to e.g. up to 50%, 33%, and 25% etc. of the flow rate of the initial pulp-free process stream prior to the division. Alternatively, one of the partial streams may exhibit a higher flow rate than the other partial stream(s). Typical percentile ratios of flow rates may be 5:95, 10:90, 15:85, 20:80, 25:75, 30:70, 35:65, 40:60 and 55:45. When dividing e.g. into three partial streams, each process stream may have a flow rate corresponding to one third of the flow rate of the stream. Alternatively, one or two partial streams may have a flow rate higher or lower than the third stream, provided that the sum of the flow rates of the partial streams preferably equals the flow rate of the initial stream. Thereby, e.g. modified lignin-derived components comprised in all partial streams may be simultaneously supplied to (conventional) combustion as an energy source, to further processing according to the inventive method and, e.g., to storage facilities, e.g. a container. Hence, said stream division may provide a "buffer capacity" depending on the status of the plant and the turnover of the method as a whole, which adds versatility and efficiency to the method, preferably without generating extra waste.

Dividing the stream for further processing according to step (D.2) may be carried out by technical means known in the field of fluid process technology. Preferably, the dividing means are adjustable in such a way, that defined portions of the stream of step (C) may be mechanically divided into two or more, three or more or four or more partial streams. The means for dividing may be selected from a flap, hatch, clack, lid, valve, damper or shutter or a combination thereof. Said means may operate electrically and/or hydraulically. Alternatively, the stream may be divided into partial streams by vacuum and/or pressurized gas, i.e. portions of the stream may be sucked or blown into two or more passages. Therein, a passage is understood as any form of duct, which passes the respective stream to its next stage. The dividing means and/or of the passages conducting the partial process streams are typically made of non-corroding metal, preferably coated or non-coated stainless steel.

By step (D) of the inventive method, all or a portion of the fraction of modified lignin-derived components is isolated from the one (alternative (D.1)) or from at least one of at least two process streams (alternative (D.2)). By alternative step (D.1), isolation of the fraction of modified lignin-derived components from the single process stream may be controlled by the isolation means applied, e.g. by the parameters applied (e.g. the amount of precipitation agent, pH, extraction or filtration characteristics, which define the setting in step (D.1). Hence, step (D.1) is less flexible than step (D.2) and requires more complex controlling efforts. Thus, dividing the product stream into partial product streams adds flexibility to the control of the yield envisaged for the fractions comprised in the essentially pulp-free process stream. Therefore, by alternative step (D.2), isolation of the fraction of modified lignin-derived components is applied to one or more of the partial streams provided at the stage of step (C). Isolation, i.e. controlled removal of the fraction of modified lignin-derived components from the process stream(s) may alternatively be applied to all partial process streams, if required. Typically, the essentially pulp-free process stream provided by step (C) is divided into two partial process streams, with one of them subjected to isolation of the fraction of modified lignin-derived components from the process stream and the other partial process streams being used for combustion and/or other uses.

In particular, the fraction of modified lignin-derived components may be isolated from the solvent and/or dispersant of the process stream, such that the fraction of modified lignin-derived components may be obtained as dry matter. It may then be re-dissolved in a suitable solvent or dispersed in a suitable dispersant, e.g. an aqueous solvent or dispersant, to be further processed in the subsequent method step. Alternatively, the fraction of modified lignin-derived components may be enriched, e.g. by reducing the solvent and/or dispersant content of the fraction of modified lignin-derived components, such that a concentrated solution or dispersion is provided. Isolation of step (D) may be carried out by any appropriate means employed in the field of solid-fluid or fluid-fluid separation. The isolation may, for example, involve filtration, extraction, counter current flow separation and precipitation. Any technology may be used according to step (D) of the invention to control the amount of isolated modified lignin-derived components, which may then be subjected to further processing.

Whether filtration is applied by step (D) or not may depend on whether the modified lignin-derived components are dissolved in the fluid phase or suspended as solid components. Filtration is preferably used for separation of suspended or dispersed solid, i.e. preferably dispersed particles of a size of about >1 μm. By filtration, oversize solid particles are typically retained by the membrane with the yield depending on the character of the modified lignin components, their particle size and the filter's cut off.

"Filtration" is hereby understood as a physical purification or enrichment method involving membrane technology by permeable membranes. Membranes are characterized by their nominal pore size. It typically describes the maximum pore size distribution. As that parameter provides only vague information about the retention capacity of the membrane, the "cut-off" is typically used as the parameter to characterize separation properties of membrane-associated filtration. The exclusion limit or "cut-off" of the membrane is usually specified in the form of NMWC (nominal molecular weight cut-off, or MWCO, molecular weight cut off, with units in Dalton). It is commonly defined as the minimum molecular weight of a globular molecule that is retained to 90% by the membrane. In practice, the MWCO of the membrane should be at least 20% lower than the molecular weight of the molecule that is to be separated. For example, a 1 kDa filter is suitable to let pass a small molecule with a molecular weight of, e.g., 500 Da, while the larger modified lignin-derived components of a molecular weight of, e.g., 2.000 Da are not able to pass.

Preferably, filtration is used herein to isolate, in step (D), the dispersed or suspended modified lignin-derived components obtained in step (B). The filter cut-off is set in such a way, that it is suitable to discriminate the molecular weight of the target modified lignin-derived components and of other components in the process stream. The other components may be larger (e.g. residual natural lignin and/or fragments thereof having a higher molecular weight than the modified lignin-derived components) or smaller (e.g. reactive agents of the pulping process, hydrolyzed hemicellulose) than the target components. If the target modified lignin-derived components are of a larger molecular weight than all other components in the process stream, the filter is selected to have a cut off such that the target components are typically retained in the filter. Otherwise, if other components are larger—in terms of molecular weight-than the modified lignin-derived components, the cut-off may typically be selected such that the target components may typically be found in the filtrate.

Typically, the filtration in isolation step (D) may be a combination of (different) filtration steps. Therein, for example, in one step the cut off of the filter is selected to be higher than the molecular weight of the modified lignin-derived components. Accordingly, other components with a higher molecular weight are kept in the filter and the modified-lignin-derived components remain in the filtrate, i.e. in the residual process stream. In another step, the residual process stream may be subjected to a second filtration, wherein the cut-off is selected to be lower than the molecular weight of the modified lignin-derived components. Accordingly, the target modified lignin-derived components are retained in the filter and, thereby, isolated from the residual process stream. Thereby, the target components may be obtained as dry matter and may subsequently be dissolved for further processing.

The more the different fractions within the process stream differ in terms of their molecular weight, the more effective may the isolation by filtration be carried out. For example, as the Kraft process typically yields modified lignin-derived components (Kraft lignin) of lower molecular weight than the sulfite process, filtration may be very preferred to separate Kraft lignin from lignin-derived material of higher molecular weight, such as non-modified or re-polymerized lignin-derived material or other debris in step (D).

Alternatively, extraction e.g. by means of an organic solvent, may be performed. As used herein, "extraction" is typically a separation process comprising the separation of a target substance from its environment. It may include liquid-liquid extraction and/or solid phase extraction. Extraction may use two immiscible phases to separate dissolved modified lignin-derived components from the original phase into another. By extraction, organic compounds are extracted by an organic solvent from the aqueous phase. Common solvents for extraction are classified by their polarity from ethyl acetate (lowest polarity) to water (highest polarity):ethyl acetate<acetone<ethanol<methanol<acetone:water (7:3) <ethanol:water (8:2)<methanol:water (8:2)<water, in the order of the Hildebrand solubility parameter. The solution containing the extracted fraction (i.e. the components) may be dried, e.g. by using a centrifugal evaporator or a freeze-drier.

For example, Kraft lignin may be extracted by step (D) from the process stream, it less soluble in an aqueous medium than in appropriate organic solvents (such as methanol, ethanol, acetone and aqueous mixtures thereof known in the art).

Alternative extraction techniques may include supercritical carbon dioxide extraction, ultrasonic extraction, heat reflux extraction, microwave-assisted extraction, instant controlled pressure drop extraction (DIC), and perstraction. Amongst them, perstraction may be preferred. Typically, "perstraction" includes two liquid phases, with only one phase including a solvent for extraction. Perstraction may advantageously be more gentle, faster and cheaper than traditional biphasic extraction techniques. "Stripping" may be employed as another gentle extraction alternative, which allows the fraction of modified lignin-derived components may be isolated from the process stream. "Stripping" is generally a physical separation process, wherein one or more components are removed from a liquid stream by a vapor stream. In industrial applications, the liquid and vapor streams may be employed co-currently or flow countercurrent. Stripping is usually carried out in either a packed or trayed column.

Isolation of the fraction of modified lignin-derived components in step (D) may generally be achieved by counter-current flow, with the flow forwarded in opposite directions. For the inventive method the concentration of dissolved modified lignin-derived components along the concentration gradient may be envisaged. The counter-current exchange method may maintain the gradient of the two flows essentially stable for the entire contact zone. Hence, countercurrent flow is particularly suitable to isolate dissolved modified lignin-derived components and may be less preferred for dispersed modified lignin-derived components.

Further, precipitation may be employed as an isolation method to allow a solid fraction to be isolated from solution. Precipitation may also be employed to control the amount of precipitated modified lignin (within a given time window) by the choice of the added amount of precipitation agent and/or the pH. Preferably, precipitation of step (D) may be conducted by means of the addition of a cation, preferably a di- or multivalent cation, most preferably of calcium.

The remainder of modified lignin-derived components, which are not further employed by the present invention, may be channeled to the paper manufacturing process or may serve for other applications such as energy provision, or may be stored for later use or may be discarded.

Precipitation in step (D) may be in particular preferred for lignosulfonate or, equivalently, for sulfonated Kraft lignin. Precipitation by pH is less preferred, e.g. for lignosulfonate, as it is generally soluble in water over the entire pH range and may not be readily isolated by pH modification. However, precipitation by calcium salt addition may be preferred. E.g., excess lime (i.e. a calcium-containing inorganic material, in which carbonates, oxides and hydroxides typically predominate) may be added to the process stream, such that calcium lignosulfonate may precipitate. This process is generally known as Howard process. It is the most straightforward recovery method known. Typically, up to 95% of the stream's lignosulfonate may be isolated by precipitation. Modified lignin resulting from the Kraft process ("Kraft lignin") may be sulfonated in step (B) and thereafter subjected to, e.g., lime precipitation.

In step (E) of the inventive method, the isolated fraction of modified lignin-derived components of step (D) is subjected to a chemical (and optionally physical) decomposition step. The reaction may allow to convert the fraction of modified lignin-derived components of higher molecular weight to lower molecular weight compounds characterized by structural elements or units of the initial lignin polymer. Step (E) corresponds to a decomposition reaction of the modified lignin-derived components resulting in a heterogeneous ensemble of preferably low molecular weight compounds of typically aromatic nature.

Disruption of the modified lignin-derived components into smaller subunits is an important step for lignin valorization. The smaller subunits may preferably resemble the desired target compounds, and may expose various functional groups on the aromatic rings to further catalytic transformation e.g. in step (G) of the inventive method.

Chemical decomposition comprises (alternative E.1) oxidative cracking (cracking and oxidizing) of the modified lignin-derived components isolated in step (D). Typically, such decomposition is carried out in the presence of a homogeneous metal ion-based or a metalloid-based catalyst.

By alternative step (E.2), reductive cracking (cracking and reducing) is applied to decompose the modified lignin-derived components in the presence of a heterogeneous metal ion-based or metalloid-based catalyst.

By alternative (E.3), said step is characterized by electro-oxidation of the modified lignin-derived components in alkaline or acidic solution.

Alternatively, decomposition may be accomplished enzymatically (E.4). Another possibility is to apply photooxidation (E.5). According to a further alternative, decomposition can be effected in ionic liquids (E.6).

Chemical decomposition is typically understood as the provision of a plurality of lower molecular weight compounds by chemical and/or physical degradation of higher molecular weight starting material. Typically, such a reaction yields compounds comprising fragments or moieties of the higher molecular weight starting material. Chemical decomposition may be studied by chemical analysis, e.g. by mass spectrometry, gravimetric analysis, and thermogravimetric analysis. Preferably, decomposition according to the inventive method is carried out by catalytic reaction, or alternatively, electrolytically. Thermal decomposition may be employed as well according to the invention, but is less preferred, as it usually yields an even broader spectrum of diverse low molecular weight lignin-derived compounds. A larger fraction of these compounds following decomposition is of aromatic nature reflecting aromatic ring systems of the building blocks of the natural lignin polymer provided in step (A).

Decomposition may result in a heterogeneous ensemble of lignin-derived products comprising (modified) lignin-derived building blocks, i.e. "monomers" or "dimers", preferably biphenylic dimers. Preferably, the resulting modified lignin-derived products herein essentially consist of monomers and dimers, i.e. the resulting lignin-derived products of step (E) do preferably not comprise larger (oligomeric) modified lignin-derived fragments but only modified lignin-derived monomers and dimers. Higher molecular weight modified lignin-derived components converted by step (E), preferably chemically modified lignin polymers (such as lignosulfonate and Kraft lignin), decompose in a controllable manner at elevated temperatures, preferably below the pyrolytic temperature of, e.g. 1000° C., such as at least 300° C., preferably at least 400° C., more preferably 400 to 500° C. and in the presence of a suitable catalyst (e.g. in a oxidative cracking (cracking and oxidizing)/reducing reaction) and/or when subjected to electro-oxidation.

Generally, "cracking" describes any type of molecular dissociation under the influence of, e.g., heat, catalysts, electric currents and/or solvents. "Cracking" of the isolated fraction of modified lignin-derived components, e.g. lignosulfonates, is understood as the reaction underlying the decomposition or decomposition of step (E.1) or (E.2). Cracking kinetics and the products of that reaction are typically dependent on the temperature and/or the catalysts applied. In addition, the ensemble of products resulting from cracking is dependent on the nature of the lignin-derived fraction used as starting material for the decomposition reaction. Accordingly, the fraction of modified lignin-derived components, e.g. Kraft lignin or lignosulfonate, may be subjected by step (E) to a catalytic reaction at a temperature significantly lower than pyrolytic temperature or to electric current, preferably by electro-oxidation.

"Oxidation" is involved in the decomposition reaction according to step (E.1). As used herein, "oxidation" refers to any reaction, which includes loss of electrons. More specifically, the term refers to the introduction oxygen-containing functional groups, e.g. a hydroxyl group. For the method of the present invention, aromatic ring systems are typically functionalized by an oxygen-containing functional group and/or by the substitution of a hydroxyl group by an oxo group. Oxidation is typically achieved by an oxidizing agent. An oxidizing agent may—more generally—correspond to any chemical species that removes electron(s) from another species. More specifically, it transfers (electronegative) oxygen to a substrate.

"Catalysis" is involved in step (E.1) and (E.2). It typically allows to enhance the kinetics of a chemical reaction by the presence of a catalyst lowering the activation energy.

Preferred catalysts for oxidizing of the (modified) lignin-derived components in step (E.1) are catalysts comprising metal ions, such as salts with catalytically active cations, or coordination (metal or metalloid) complexes. In general, a "coordination complex" is typically known in chemistry to consist of a central atom, which may be a metallic or metalloid atom, e.g. a metal ion or a metalloid ion. It is called the coordination center. The surrounding sphere of bound molecules or ions is known as ligands or complexing agents. Alternatively, catalysts may be of metalloid character including coordination complexes, with a metalloid atom as the coordination center, such as boron. In particular, catalysts used according to step (E.1) are homogeneous catalysts, but may also be heterogeneous catalysts. Generally, homogeneous catalysis is based on catalytic reactions with the catalyst being in the same phase as the reactant(s). More specifically, a homogeneous catalyst is dissolved for catalysis in the solution.

Heterogenous catalysts of interest for step (E.1) of the inventive method include $TiO_2$, $Pt/TiO_2$, $Fe(III)/TiO_2$, $Pd/Al_2O_3$, $Ni/MgO$, $CH_3ReO_3$, Cu—Ni, Cu-Mnm, Cu—Co—Mn, Cu—Fe—Mn, Cu—Ni—Ce/$Al_2O_3$, Cu—Mn/$Al_2O_3$.

Homogenous catalysts of interest for step (E.1) of the inventive method may be selected from the following, non-limiting examples of suitable catalysts.

Homogenous catalysts applicable in step (E.1) of the inventive method may include metalloporphyrins, including catalysts formed from the metalation of the porphyrin with transition metal salts. Metalloporphyrins of interest as catalysts in step (E.1) of the inventive method include Mn(TSPc)Cl, Fe(TSPc)C, Fe(TF$_5$PP)Cl, CoTSPc, FeTSPc, Rh(TSPP), Fe(TF$_5$PP)Cl and Mn(TSPP)Cl. Crestini and Tagliatesta provide an extensive review on the oxidation of lignin using metalloporphyrin complexes (cf. Crestini and Tagliatesta. The Porphyrin Handbook; Kadish, K. M., Smith, K. M., Guilard, R. Eds.; Academic Press: San Diego, Calif., 2003; Vol. 11, p 161)

Homogenous catalysts applicable in step (E.1) of the inventive method include Schiff-base catalysts, especially metallosalen catalysts. These are emerging as promising oxidation catalysts of lignin and modified lignin-derived components. The term "salen" refers to [N,N'-bis(salicylidene)ethane-1,2-diaminato]. Metallosalen catalysts of interest as catalysts in step (E.1) of the inventive method include Co(salen), [(pyr}Co(salen)], Cu-, Fe-, and Mn-triphenylphosphonium-decorated salen complexes, Co-sulphosalen, Co(salen)/SBA-15, and [Co(N-Me salpr)].

Homogenous catalysts applicable in step (E.1) of the inventive method include nonporphyrinic or Schiff base catalysts, including metallo-TAML (tetraamido macrocyclic ligand), -DTNE (1,2-bis-(4,7-dimethyl-1,4,7-triazacyclonon-1-yl)ethane) and -TACN (1,4,7,-trimethyl-1,4,7-triazacyclononane) catalysts. The metal may for instance be selected from iron or manganese. Catalysts of use in step (E.1) of the inventive method in this regard include Mn(IV)-Me$_4$DTNE and Mn(IV)-Me$_4$TACN.

Homogenous catalysts applicable in step (E.1) of the inventive method include polyoxometalates (POMs), as reviewed in detail by Gaspar et al. Green Chem. 2007, 9, 717. Polyoxometalates consist of both primary and secondary heteroatoms, where the former typically determines the structure and the latter, typically transition metal ions, may be substituted without change of structure. Thereby, secondary heteroatoms can be replaced by ions conferring desirable redox characteristics. POMs of interest as catalysts in step (E.1) of the inventive method include SiW$_{11}$Mn(III), BW$_{11}$Co(III), PW$_{11}$Ru(IV), heteropolyanion-5-Mn(II), alpha-[SiVW$_{10}$O$_{40}$]$^{5-}$, Na$_{5(+1.9)}$[SiV$_{1(-0.1)}$MoW$_{10(+0.1)}$], LaMnO$_3$, LaCoO$_3$, H$_2$MoO$_4$ and Fe$_2$(MoO$_4$)$_3$. POMs may be utilized as catalysts in conjuction of $O_2$ or $H_2O_2$ as oxidants.

Homogenous catalysts applicable in step (E.1) of the inventive method include simple metal salt-based catalysts. These may typically utilized in conjunction with $O_2$ as oxidant. Metal salt-based catalysts of interest as catalysts in step (E.1) of the inventive method include Co(OAc)$_2$/Mn(OAc)$_2$, Co(OAc)$_2$/Mn(OAc)$_2$/HBr, Co(OAc)$_2$/Zr(OAc)$_4$/HBr, Mn(OAc)$_2$, CuSO$_4$, CuSO$_4$/FeCl$_3$, Cu(OH)$_2$, FeCl$_3$, Fe$_2$O$_3$, NaBr 2,2,6,6-tetramethylpiperidine-1-oxyl-radical (TEMPO), CuO, and CoO.

Homogenous catalysts applicable in step (E.1) of the inventive method further include miscellaneous catalysts, including hexacyanoruthenate(II)), Ru/CN)$_6^{4+}$, tris-(4,4'-dimetyl-2,2'-bipyridine)iron(II) and [Cu(phen)(OH)$_2$].

In principle, step (E.1) of the inventive method can be performed with any of the aforementioned homogenous catalysts.

By alternative step (E.2), the fraction of modified lignin-derived components is reduced, typically by addition of a reducing agent. A "reducing agent" is understood as an agent which "donates" electron(s) to another chemical species (electron donor). The catalyst typically employed by step (E.2) is a heterogeneous catalyst, which is defined as a catalyst provided in another phase, typically in solid or gaseous phase, than the reactant(s), which are typically provided in solution.

For the present method, the modified lignin-derived components are typically provided in solution and the catalyst is usually provided as solid matter. Generally, heterogeneous catalysis provides the advantage that reaction products may readily be separated from the catalyst component. Advantageously, heterogeneous catalysts are usually more stable and decompose more slowly than homogeneous catalysts. They may be recycled.

Heterogenous catalysts applicable for reductive cracking (cracking and reducing) of lignin include, without limitation, Cu.CrO, Raney Ni, Rh, Pd.FeS, Co—Mo, Ni—Mo, Co—Mo—P, Fe$_2$O$_3$, Mo, Ni—Mo—P, Mo$_2$N, Ni—W, Rh—Co, Ni—Cu, NiO—MoO$_3$, MoO$_3$Ru, M or M—Mo (wherein M is selected from Co, Cu, Ir, Ru, Pd, Fe, Rh, Pt or Ni). Optionally, the support (i.e. a material to which the catalyst is affixed) may be selected from carbon, Al$_2$O$_3$, TiO$_2$, SiO$_2$—Al$_2$O$_3$, ZrO$_2$, CeO$_2$, zeolite, MgO or nothing.

A homogeneous catalyst may, however, alternatively be employed. Suitable homogenous catalysts include (1,5-hexadiene)RhCl dimer, colloidal rhodium, [(1,5-C$_6$H$_{10}$)RhCl]$_2$, rhodium nanoparticles, [(C$_6$H$_6$)Ru$_4$H$_{4l}$]Cl$_2$, [(Ru(C$_5$H$_5$)Cl(TPPDS)$_2$], NaBH$_4$+I$_2$, and RuCl$_2$(PPh$_3$)$_3$.

With regard to step (E.3), "electro-oxidation" is understood as oxidation at the surface of an electrode and/or in an electrical (electrochemical) cell. Preferably, any such electrical cell employed by step (E.3) is a single galvanic cell or a flow cell. A flow cell is characterized by the ionic solution (electrolyte) passing continuously or batch-wise through the cell. The ionic solution is typically stored in separate storage tanks.

Enzymatic decomposition according to step (E.4) of the inventive method may be accomplished by contacting the modified lignin-derived components with suitable enzymes (or organisms producing the same, in particular fungi) under appropriate conditions. Enzymes of interest in this regard include inter alia oxidases, peroxidases and hydrolytic enzymes, e.g. derived from *Phaerochaete chrososporium* or *Pycnoporus cinnabarinus*.

Photooxidation (E.5) may involve subjecting the modified lignin-derived components to visible or UV light, typically with a wavelength of up to 500 nm.

Alternatively, the modified lignin-derived components may be subjected to decomposition reactions in ionic liquids according to step (E.6) of the inventive method. Ionic liquids are composed of ionic organic/inorganic salts that are liquid at low temperature (<100° C.). They typically have low vapour pressures, are chemically and thermally stable and are able to dissolve in a wide range of compounds. Various decomposition reactions can be carried out in ionic liquids, for instance acetylation, acid hydrolysis, heat treatment, acylation of enzymatic treatment as described above. Ionic liquids of interest for the decomposition of the lignin-derived components of the invention include those comprising alkylsulfonates, lactates, acetates, chlorides or phosphates as anions. One of the most important advantages of some ionic liquids (e.g. 1-H-3-Methylimidazolium chloride, 1-ethyl-3-imidazolium chloride) is their ability to act as both an acidic catalyst and a solvent. Such ionic liquids may be particularly preferred. Ionic liquids may be used in conjunction with suitable transition metal catalysts (e.g. 1-ethyl-3-methylimidazolium diethylphosphate and $CoCl_2.6H_2O$, 1-ethyl-3-methylimidazolium trifluoromethylsulfonate and $Mn(NO_3)_2$) which may promote the decomposition of modified lignin-derived components.

Optionally, the above-mentioned alternatives may be combined with each other. E.g., a synergistic combination of photo-electrocatalysis using a three-electrode iridium oxide system coupled with UV light may be employed. A combination of enzyme-based approaches and ionic liquid is described above.

Further, the method of the invention comprises by its step (F) an isolation step, wherein the desired low molecular weight aromatic lignin-derived compounds are separated from (residual) higher molecular weight aromatic lignin-derived components and/or other non-lignin-derived residual components, which have not been decomposed or decomposed to a less significant degree, or which have adversely re-polymerized. Decomposition reactions are avoided by step (E) of the inventive method, which are characterized by reaction conditions, which bear the risk of re-polymerization of the lignin-derived material to be decomposed. Nevertheless, any such by-products may still result from step (E), which need to be eliminated downstream of the inventive method. Components other than the desired target lower molecular weight aromatic lignin-derived compounds are either discarded, e.g. for combustion, or recycled by another step of decomposition (e.g. a second decomposition reaction according to step (E)).

The target compound of the inventive method is a low molecular weight aromatic lignin-derived compound. A "lignin-derived low molecular aromatic weight compound" is preferably a molecule, which corresponds or is derived from a (monomeric) building block of natural lignin or is a homo- or heterodimer of such (monomeric) building blocks. Such target compounds are derived from natural lignin via its modification resulting from step (B) ("pulping"), which provides the fraction of modified lignin-derived components as intermediates of the inventive method. Subsequently, a decomposition step (E) provides low molecular weight target compounds.

The term "aromatic" refers to a compound, which fulfils the criterion of aromaticity—as it is generally defined in the art. Therein, the term "aromatic" is typically used to describe a cyclic, i.e. ring-shaped, and planar system that exhibits increased stability as compared to linear, i.e. line-shaped, molecules with the same number of atoms. As a result of its increased stability, the aromatic system is less prone to react under conventional conditions. In terms of the electronic nature of the molecule, aromaticity describes a conjugated system usually described by alternating single and double bonds within the ring system. This configuration typically allows for the electrons in the molecule's pi system to be delocalized around the ring, increasing the molecules' stability. The most commonly encountered aromatic system in organic chemistry are benzene and its derivatives. The model description for benzene typically consists of two resonance forms, which corresponds to the double and single bonds superimposing to produce six one-and-a-half bonds. Benzene is more stable by its charge delocalization than is to be expected. Non-carbocyclic and/or non-hexacyclic aromatic systems understood to be aromatic as well, if they fulfil the aromaticity rules, such as heterocyclic aromatic compounds, di-tri- and tetracyclic compounds and compounds having any n-membered rings such as 5-membered rings. Any aromatic functional group may be designated as "aryl group". Aromatic compounds are commonly isolated in the art from petroleum or its refined fractions.

Preferably, aromatic target compounds of the inventive method comprise carbocyclic benzene or its benzene derivatives, such as phenolic derivatives. While compounds essentially comprising benzene-derived aromatic ring systems and its derivatives are preferred, aromatic target compounds comprising biphenylic, bi- and multicyclic (annulated) aromatic systems may likewise be envisaged.

A low molecular weight lignin-derived aromatic compound envisaged to be isolated by step (F) is preferably an aromatic compound, which typically exhibits a molecular weight of less than 1.000 Da, preferably less than 700 Da, more preferably less than 500 Da, most preferably of about 100 to 500 Da, e.g. 200 to 400 Da. It typically has a size in the order of $10^{-9}$ m or less. Preferably, such low molecular weight aromatic lignin-derived compound is based on a monomer or, alternatively, a homo- or heterodimer of the polymeric natural lignin which may have been modified in the pulping process of step (B) of the inventive method. "Monomers" essentially correspond to the (repetitive) building blocks of polymeric natural lignin. A "monomer" may be any building block of the natural lignin polymer, which may be modified in step (B). "Monomers" of the natural lignin polymer are typically of aromatic nature (e.g. contain an aromatic ring system), but may be diverse in terms of their specific chemical character. Typically, the target compound comprises one single benzene-derived (substituted) aromatic ring system.

The low molecular weight aromatic lignin-derived compound, i.e. typically a monomer comprising one aromatic ring system or a dimer comprising typically two (non-annulated) aromatic rings, shall be isolated in step (F) from other components resulting from decomposition of step (E), e.g. fragments other than the monomeric or dimeric target compounds, by appropriate techniques.

"Fragments" of the modified lignin-derived components are typically larger in molecular weight than the monomeric or dimeric target compounds, but have typically a lower molecular weight than the modified lignin-derived components obtained by step (B) as intermediates of the inventive method. Such fragments are typically not understood to be low molecular weight target compounds of the inventive method. Instead, they may comprise or they are tri- or n-mers of the building blocks of the modified lignin-derived components. Such fragments resulting from the decomposition step are typically oligomers being of smaller molecular weight than the modified lignin-derived components obtainable in the pulping process of step (B). However, such fragments may vary significantly in size and in their molecular weight, as the lignin-derived components vary.

By step (F), monomeric or dimeric target compounds (obtained from the decomposition reaction of, e.g. lignosulfonate, by step (E)) are isolated from the other fragments of the decomposition step (E). The monomeric or dimeric target compounds to be isolated are typically monocyclic phenolic derivatives or encompass two such monomeric moieties each containing individual (non-annulated) phenolic ring systems, respectively. For a dimeric target compound, the ring systems may be directly connected by a bond. Alternatively, two monomeric moieties containing an aromatic ring system each may be connected by a linker group, e.g. an aliphatic linker group, to form a homo- or heterodimer, typically a heterodimer. A heterodimer exhibits two aromatic ring systems with individual (distinct) substitution patterns. For some embodiments, it may be preferred for the dimer to represent the basic chemical structure of two (substituted) aromatic ring systems directly linked by a bond to form a bi-phenylic ring system.

The monomeric or dimeric compounds isolated by step (F) may be further modified according to the present invention. They may e.g. be oxidized or chemically modified by other reactions, which may result in modified substitution patterns or modified ring structure, e.g. result in annulated ring systems, e.g. result in naphthalene or anthracene-derived compounds. Thus, the low molecular weight compounds isolated by step (F) may be subjected to other chemical reactions and may thereby comprise functional groups or aromatic ring systems not occurring in the modified lignin-derived components obtained by step (B). They may, e.g., be of higher or lower oxidation state, they may contain functional groups not occurring in natural lignin at all, and/or they may exhibit bi-, tri-, tetra- or pentacyclic (annulated) aromatic ring systems. Either low molecular weight aromatic lignin-derived compounds isolated by step (F) or their derivatization products may serve for commercial application, e.g. as redox-active compounds or for any other use.

In principle, any lignocellulosic material from whatever plant may be employed in the inventive method. The lignocellulosic starting material of the method provided according to step (A) may preferably be based on wood of low silica and resin content, more preferably based on "northern woods", even more preferably based on the group consisting of beech, pine, birch, eucalyptus and spruce, most preferably based on beech. The lignocellulosic starting material of the method provided according to step (A) is preferably provided as chopped material, more preferably in the form of woodchips. Generally speaking, the Kraft process, which may be employed as step (B) of the inventive method, may consume a wider range of fiber sources than most of the other pulping processes, which may alternatively be used by the present invention (such as the sulfite process). Accordingly, the Kraft process is typically operable with all types of wood, from whatever plant, including more resinous wood species (like southern pine), and even non-wood species, like bamboo and kenaf.

By a preferred embodiment of the inventive method, the pulping process of step (B) may be selected from the group consisting of Kraft process, sulfite process, organosolv process, and lignin pyrolysis process. Other processes for separating lignin and cellulose components from lignocellulosic starting material (as described herein and known in the art) may also be used for the reaction of step (B) to arrive at a (modified) lignin-derived fraction. The Kraft process or, alternatively, the sulfite process are preferred as step (B) for the method of the invention.

The Kraft process may be carried out as alternative (B.1) according to the inventive method. The Kraft process may comprise the sub-steps of (a) optionally pre-steaming the (preferably chopped) lignocellulosic material, wherein the (preferably chopped) lignocellulosic material is advantageously wetted and preheated with steam, (b) adding (preferably chopped) lignocellulosic material to an aqueous alkaline solution comprising Kraft pulping agents, one or more of the agents preferably selected from the group consisting of a sulfide salt, a sulfhydryl compound or salt, and a polysulfide salt (and, typically, at least one sulfate salt is additionally comprised by the alkaline solution as well), (c) cooking the (preferably chopped) lignocellulosic material, which is provided (e.g. suspended and/or dispersed)) in said aqueous alkaline solution, and (d) optionally sulfonating the lignocellulosic material in the presence, e.g. of sulfuric acid solution and/or sulfur trioxide.

In contrast to the Kraft process, the sulfite process is referred to as alternative method step (B.2). The sulfite process may comprise the sub-steps of (a) optionally pre-steaming the (preferably chopped) lignocellulosic material, wherein the (preferably chopped) lignocellulosic material is advantageously wetted and preheated with steam, (b) adding the (preferably chopped) lignocellulosic material to an aqueous, preferably acidic solution comprising a sulfite and/or bisulfite salt, and (c) cooking the (preferably chopped) lignocellulosic material, which is provided (e.g. dispersed or and/or suspended) in said aqueous, preferably acidic, solution.

Thus, step (B) of the inventive method comprises a process as it may be commonly practiced as an initial step in pulp and/or paper manufacturing. Accordingly, both the Kraft process (step B.1) and the sulfite process (step B.2) are widely known from the afore-mentioned applications and are applied accordingly by the inventive method. They allow to separate cellulosic fibrous material (pulp), which is the target material in the production of pulp and/or paper, from other non-cellulosic wood components, in particular lignin or, rather, the lignin-derived components. For the inventive method, "pulp" is neither a target product nor an intermediate.

Rather, the target of step (B) is the provision of lignin as the other major wood component, preferably in its modified, advantageously soluble form ("modified lignin-derived components"). Typically, the present invention processes modified lignin-derived components, such as "Kraft lignin", "sulfonated Kraft lignin" or "lignosulfonate", upon separation of the cellulose fraction, as an intermediate of the inventive method.

The "pulp and/or paper manufacturing process" is typically a commercially established process for the production of pulp and/or paper in a pulp and/or paper manufacturing plant. As used herein, "pulp" is generally understood to essentially comprise preferably (enriched) cellulosic fibrous material prepared from, for example, wood, fiber crops or waste paper. A pulping process provides the preferably pure cellulosic fibrous material (pulp). Being typically in the form of fibers, pulp is usually not dissolved, but dispersed or suspended in the liquid employed in the pulping process.

Due to its fibrous form, pulp is typically separated by step (C) of the inventive method as fibrous material, preferably by mechanical means, such as sieves and/or centrifuges, from the method's process stream, which contains the (preferably dissolved, suspended and/or dispersed) fraction of lignin-derived material and which is further processed by step (D).

Generally, the objective of any pulp and/or paper manufacturing process is to allow disintegration of wood into fibrous cellulosic material, lignin and hemicellulose products. This is achieved by breaking covalent bonds of 3-dimensional polymeric lignin macromolecules. Carbon to carbon (C—C) bonds are more stable than oxygen-carbon bonds (C—O) under conditions typically applied for bond breaking by the "cooking" sub-step (c) of the inventive method. Thus, cleavage of oxygen-carbon bonds is the most prevalent and important reaction in any typical pulping process described herein as step (B). Thereby, cooking under alkaline conditions in the Kraft process, under acidic conditions in the sulfite process and in organic solvents in the organosolv process allows to break oxygen-carbon bonds of lignin. Typically, any such reaction of step (B) produces modified products characterized by phenolic hydroxyl groups due to cleavage of natural lignin's aryl-alkyl-ether bonds. The modified lignin-derived components as modified products of the pulping process, i.e. "the modified lignin-derived components", are of lower molecular size than the polymeric lignin starting material (natural lignin). Furthermore, such lower molecular weight lignin-derived polymers are usually more soluble or dispersible than natural lignin in the process stream leaving the pulping process of step (B). From that process stream non-dissolved or non-dispersed pulp, which usually is the target product of any commercial pulping process, may readily be separated from dissolved and/or suspended modified lignin-derived components (as realized by step (C) of the inventive method).

The present invention is characterized by the advantage that it may readily employ by its step (B) existing plants for pulp production. It is characterized by enabling commercial use of lignin (in the art typically regarded as the major undesired by-product of pulp production), which has essentially not yet been made accessible for other applications than as energy source. If required, the present invention may also use a smaller portion of the lignin-derived fraction of step (C) as energy source either for the pulp production or for further downstream steps. The present invention is, however, unprecedented, as it enables lignin (as abundantly available and renewable natural material) to become the starting material for the provision of a large diversity of organic compounds usable for a broad spectrum of applications. Some of them have been so far made available in the art by the methods of petroleum chemistry only.

The Kraft process according to step (B.1) is typically a higher pH pulping process in the presence of an aqueous solution containing one or more of salt or non-salt agents selected from the group consisting of sulfide, sulfhydryl and polysulfide. One or more sulfate salt(s) is/are typically added as well. By optional sub-step (a) of step (B.1), preferably chopped lignocellulosic material (such as woodchips) may be pre-treated with hot steam. Thereby, preferably chopped lignocellulosic material is wetted and heated, which typically renders it more susceptible to adsorb treatment solutions as applied by subsequent sub-step (b). Cavities of fresh wood are filled with fluids and/or air. Steam pre-treatment causes the air to expand. About 25% of the air and/or other fluids naturally occupying the cavities is thereby expelled from these cavities.

By sub-step (b) of the applied Kraft process, the optionally pre-treated, i.e. pre-steamed and pre-heated, preferably chopped lignocellulosic material is treated, preferably at elevated temperatures, with an aqueous alkaline solution ("treatment solution"). Typically, the lignocellulosic material is added to the treatment solution. Said solution typically comprises at least one chemically reactive agent for the Kraft process to operate. The treatment solution may be a liquor known in the art as "white liquor". The employed reactive agents may adjust the pH and/or provide nucleophilic sulfide ($S^{2-}$) and/or bisulfide ($HS^-$) ions and/or moieties. Typically, said treatment solution comprises a mixture of chemically reactive agents generally used for Kraft pulping to provide nucleophilic sulfide and/or bisulfide ion or moiety for rupturing the embedment of lignin in the cellulose scaffold of natural lignin. The reactive sulfur containing agents are usually provided as (dissolved) salts, but they may also be provided as non-salt agents, e.g. as (dissolved) organic compounds, which comprise one or more sulphur or sulphur-based chemical functionalities. Generally, any suitable reactive agent known in the art for use in the impregnation and cooking step of the Kraft process may be employed according to the present invention. Other than the sulfur containing reagents, further agents added to the solution in step (B) in lower amounts are typically one or more of sodium carbonate, sodium sulfate, sodium thiosulfate, sodium chloride, and calcium carbonate.

By sub-step (b) of the Kraft process, the preferably chopped lignocellulosic material is typically initially saturated with the aqueous alkaline solution, e.g. with the fresh ("white liquor") treatment solution or with its recycled equivalent ("black liquor"). The step is preferably designated as the "impregnation step", which may be performed before the chopped lignocellulosic material is forwarded to the vessel for the cooking process (sub-step (c)) to occur within the vessel. For sub-step (b), the preferably chopped lignocellulosic material is typically not exposed to elevated temperatures (corresponding to the cooking temperature), but just "pre-treated". Accordingly, the material is not or only gently heated for that pre-treatment step.

Additional reactive agents may be added to the treatment solution to improve the Kraft impregnation of e.g. the employed wood chips with the cooking liquor. Anthraquinone may be used as such an additive. It typically acts as a redox catalyst by oxidizing cellulose and reducing lignin. It protects cellulose from its degradation and makes the lignin component of the starting material more water-soluble. Further, an emulsion breaker may be added in an optional soap separation step to expedite and improve the separation of soap from the cooking liquors by flocculation, once they have been used. Soap, such as rosin soap, generally forms as by-product of the Kraft process. The soap typically floats at the surface of the aqueous liquid and has to be skimmed off. The collected soap may be further processed to tall oil. Advantageously, defoamers may be employed to remove eventually formed foam and foster the pulp production process. Drainage of washing equipment gives cleaner pulp. Dispersing agents, detackifiers and/or complexing agents preferably allow to keep the process vessels cleaner and to reduce the number of maintenance operations. Fixation agents may be used to allow finely dispersed material to be deposited on the fibers, thereby allowing such material to be readily eliminated.

Generally, aqueous alkaline solution ("liquor") used for impregnation may be applied for the cooking step as well. Hence, the aqueous alkaline solution (treatment solution) used for impregnation in sub-step (b) in the Kraft process— and likewise the corresponding aqueous acidic solution for the sulfite process—is defined as "cooking liquor" in sub-step (c). By impregnation in sub-step (b), the treatment solution (or "cooking liquor") preferably penetrates into the capillary structure of the chopped lignocellulosic material, such that initial reactions with the wood components start at low temperature conditions. Intensive impregnation supports the provision of a homogeneous cook and low rejects. Thereby, a larger portion of lignin is yielded as soluble "Kraft lignin". Usually, about 40-60% of all alkaline pulping liquor is consumed for the continuous type Kraft process in its initial impregnation step.

By sub-step (c) of step (B.1) of the inventive method, the pre-treated (impregnated) preferably chopped lignocellulosic material is cooked in said aqueous alkaline treatment solution as required. The cooking period may depend on the reaction conditions, i.e. the pH, pressure and temperature, and may further depend on the type and strength of the employed chopped lignocellulosic material. For Kraft processing, the material is cooked for several hours, e.g. 3 to 9 hours. Essentially, the Kraft process breaks natural lignin's internal ether bonds by nucleophilic attack of sulfide ($S_2^-$) and/or bisulfide ($HS^-$) ions or moieties. The function of sulfide in the Kraft process may be two-fold: It may promote and accelerate the cleavage of ether bonds between neighboring building blocks of lignin's 3-dimensional polymeric structure and it reduces the extent of undesirable condensation.

The modified lignin-derived components obtained from sub-step (c) of step (B.1) are commonly known as "Kraft lignin". These components are essentially unsulfonated or at least less sulfonated than "lignosulfonate" resulting from the sulfite process. Typically, they are more soluble in aqueous alkaline solution, preferably at a pH of greater than about 9 and reasonably soluble in strongly polar organic solvents. The average molecular weight of the lignin-derived components is generally between 1.000 and 4.000 Da, preferably 2.000 to 3.000 Da. Usually, the average component of that lignin-derived fraction comprises about 10 to 35 building blocks, preferably 10 to 25 building blocks, and thus, may have a "polymerization degree" of 10 to 35, preferably 10 to 25. The lignin-derived material typically exhibits a polydispersity of between 2 and 4, although it can be as high as 8 or 9. Material of such higher values of polydispersity may be typically employed for industrial grade applications, but does usually not allow its subsequent exploitation as basic material for the provision of a larger variety of organic target compounds as envisaged by the invention. Accordingly, polydispersity of the material obtained by sub-step (c) should not go beyond 6, preferably should be less than 5 or from 2 to 5. A "molecular formula" of $C_9H_8.5O_{2.1}S_{0.1}(OCH_3)_{0.8}(CO_2H)_{0.2}$ was previously reported for softwood Kraft lignin. About 4% by weight is typically free phenolic hydroxyl. (Lebo, S. E. et al, Lignin, Kirk-Othmer Encyclopedia of Chemical Technology, p. 18 of on-line version, (2001), John Wiley & Sons, Inc.). Kraft process-derived modified lignin-derived components typically also comprise biphenylic moieties, in particular when using lignocellulosic starting material being of spruce origin. Hence, spruce may be the preferred starting material for the inventive method, if dimeric biphenylic target products are desired.

In order to obtain material from the Kraft process, whose water-solubility is increased over a wider pH range, i.e. for acidic and neutral pH milieu, sub-step (d) may optionally be added to step (B.1). That sub-step is preferably a sulfonation step. Therein, sulfonating agents known in the art, such as a solution of preferably concentrated sulfuric acid, may be added. Aliphatic side chains are typically sulfonated, e.g. by the introduction of sulfonyl moieties as substituents of side chains of Kraft lignin. Sulfonation may occasionally also affect the aromatic rings of the Kraft lignin components.

By sulfonation of Kraft lignin, sulfonated modified lignin is obtained, which is herein understood as "sulfonated Kraft lignin".

Generally, sulfonation of sub-step (d) confers increased solubility and surfactant properties to Kraft lignin. "Sulfonated Kraft lignin" shares characteristic structural or functional properties with "lignosulfonate" of the sulfite process, such as water solubility over a broader pH range. Both, Kraft process-derived "sulfonated Kraft lignin" and sulfite process-derived "lignosulfonate" are referred to as "sulfonated lignin". Kraft process-derived "sulfonated Kraft lignin" and sulfite process-derived "lignosulfonate" are generated under distinct chemical conditions resulting in structural distinct lignin-derived compositions. The average molecular weight of components of "sulfonated Kraft lignin" is typically lower than the average molecular weight of components of "lignosulfonate" resulting from the sulfite process. Accordingly, the molecular weight of the components of sulfonated Kraft lignin may typically be about 1.000 to 4.500 Da, preferably 2.500 to 3.500 Da.

For sulfonation according to sub-step (d), overpressure and/or increased temperature may be applied. After a reaction period of preferably at least two hours, sulfonated Kraft lignin may be recovered, e.g., by water removal or by precipitation, e.g. with excess lime, as calcium lignosulfonates. As sulfonation confers improved water solubility properties to Kraft lignin, it makes such sulfonated lignin-derived material easier to separate in an aqueous environment from insoluble cellulosic material. In standard pulp and/or paper manufacturing plants operating under the Kraft process, additional sulfonation step (d) (which may also be designated as "postsulfonation" for Kraft lignin) is therefore typically beneficially applied.

Sulfonation sub-step (d) of the Kraft process (B.1) is preferably carried out at a temperature below 300° C., more preferably below 200° C. Such elevated temperatures preferably ensure both sufficiently high yields of sulfonated reaction products, while it avoids premature, i.e. uncontrolled thermal degradation of the lignin-derived Kraft lignin material. Thereby, it is ensured that the lower molecular weight (as compared to the natural lignin polymers) aromatic lignin-derived components remain intact (without uncontrolled degradation) for their further processing towards the inventive method's target compounds. Low molecular weight monomeric or dimeric target compounds are obtained by well-controlled decomposition of the modified lignin-derived components in downstream method step (E), followed by subsequent isolation (purification) in step (F). Accordingly, the largest portion of modified lignin-derived components possible resulting from step (B) shall be made available for controlled decomposition in downstream step (E). Otherwise, the yield of the target compound would be unfavorably reduced.

By alternative method step (B.2), the preferably chopped lignocellulosic material may be subjected to the sulfite process comprising the sub-steps of (a) optionally pre-steaming the chopped lignocellulosic material, wherein the preferably chopped lignocellulosic material is wetted and preheated with steam, (b) providing an aqueous, preferably acidic solution comprising sulfite and/or bisulfite, and (c) cooking the preferably chopped lignocellulosic material in said aqueous, preferably acidic solution.

The sulfite process employed by step (B.2) of the invention is another pulping process. The resulting solid cellulose fibers are obtained by using salts of sulfurous acid to separate the lignin fraction from natural lignocellulosic starting material, such as wood chips, e.g. in digesters preferably operating at larger pressure. The salt anions used in the pulping process may either be sulfites ($SO_3^{2-}$), and/or bisulfites ($HSO_3^-$), depending on the pH. At lower pH, i.e. under stronger acidic conditions, such as less than pH 2.5, the sulfite is typically provided as $HSO_3^-$. Counter cations may be sodium ($Na^+$), calcium ($Ca^{2+}$), potassium ($K^+$), magnesium ($Mg^{2+}$) or ammonium ($NH_4^+$). Particularly divalent (e.g. earth alkali) cations, such as calcium and/or magnesium, may be used as the counter cation. The preferred salt is calcium bisulfite, which may advantageously be employed, if the selected pH value for the sulfite process is 2.5 or less. Higher pH sulfite pulping (at a pH above pH 2.5 or, more specifically, above pH 4) generally employs monovalent ions, such as sodium or ammonium, as counter cations. Sulfite pulping is preferably carried out under acidic conditions, preferably at a pH below 5, preferably from pH 1.5 to 5 or 1.5 to 4. The (acidic) pH may be adapted depending on the nature of the counter cation for the sulfite (bisulfite) anion. However, it is not excluded that sulfite pulping may be carried out over a wider pH range, including alkaline conditions of about pH 7 to 12.

The aqueous, preferably acidic sulfite and/or bisulfite containing solution used as "pulping liquor" for the sulfite process may be provided as follows: Sulfur may be oxidized (burnt) with the stochiometrically adequate amount of oxygen to yield sulfur dioxide. Sulfur dioxide is preferably added, e.g. as a gas, to water to give sulfurous acid, which may be further diluted for its use as "pulping liquor".

The lignocellulosic material may be brought into contact with the pulping reactive agents for more than three hours, preferably 4 to 14 hours. The temperature is typically above 120° C., preferably ranging from 130 to 160° C., depending on the reactive agents and their concentrations used.

The modified lignin-derived components resulting from the sulfite process are generally designated as "lignosulfonate". Due to the nature of the sulfite process, "lignosulfonate" typically contains significant amounts of sulfur-based moieties (typically in the form of sulfonate groups), for example, in the aliphatic side chains of the modified lignin-derived components.

"Lignosulfonate" is a complex (heterogeneous) mixture of modified lignin-derived components, i.e. water-soluble anionic lignin-derived polyelectrolytes, which carry —$SO_3H$ functional groups. Lignosulfonate typically exhibits by its heterogeneous components a broad molecular weight range (broader than observed for Kraft lignin). Lignosulfonate is polydisperse with a polydispersity being typically higher than that of the Kraft process (about 4 to 9). As the sulfite process is less destructive than Kraft pulping, it does not degrade lignin to the same extent as the Kraft process. Thus, sulfite process-derived lignosulfonate typically has a higher average molecular weight than Kraft lignin as described herein. A maximum molecular weight of 140.000 Da is reported for softwood lignosulfonates, while maximum values for hardwoods are usually lower, e.g. lower than 50.000 Da. The typical range of the molecular weight for lignosulfonate polymers is about 5.000 to 50.000 Da, preferably about 5.000 to 20.000 Da (Brogdon, B. N., Dimmel, D. R. J. Wood Chem. Technol. 1996, 16, 297). Usually, it comprises about 10 to 300 building blocks, preferably 20 to 200, most preferably 25 to 150 building blocks, and thus, may have a "polymerization degree" of 10 to 300, preferably 20 to 200, most preferably of 25 to 150. It typically exhibits a higher sulfur content (about 3% to 8% w/w) than (unsulfonated) Kraft lignin (having a sulfur content of typically less than 1% w/w). Lignosulfonates are used in the art as low-value chemicals in tanning leather, making concrete, drilling mud and drywall, such as binders or additives for building material.

Sulfite process-derived lignosulfonates are typically soluble in water over essentially the entire pH range. Sulfite process-derived lignosulfonate may also be soluble in highly polar organic and amine solvents. Its approximate "molecular formulas" are described as $C_9H_{8.5}O_{2.5}(OCH_3)_{0.85}(SO_3H)_{0.4}$ for softwood or as $C_9H_{7.5}O_{2.5}(OCH_3)_{1.39}(SO_3H)_{0.6}$ for hardwood, respectively, as starting material for sulfite process-derived lignosulfonate. Sulfite process-derived lignosulfonate may comprise biphenylic moieties for some of the components of the larger number of components representing the "lignosulfonate" fraction. That holds specifically for lignocellulosic material of spruce origin. Hence, spruce may be the preferred starting material for the inventive method, if biphenylic target products are desired.

Generally, modified lignin-derived components, such as (sulfonated) "Kraft lignin" and/or "lignosulfonate", are typically dissolved or dispersed in the consumed pulping liquor, once processed according to step (B). Said liquor (process stream leaving step (B)) usually also comprises most of the hemicellulose and/or its hydrolysis products (poly-, oligo and/or monosaccharides) in dissolved form.

Preferably, the pH of the aqueous alkaline solution in sub-step (b) of step (B.1) is >10. More preferably, the pH in sub-step (b) of step (B.1) is >12. The temperature of the aqueous alkaline solution in sub-step (b) of step (B.1) is typically less than 100° C., e.g. in the range from 70° C. to 90° C.

For sub-step (b) of (B.2), the pH of the aqueous preferably acidic solution is preferably 1 to 5 and more preferably 1.5 to 4. The temperature of the aqueous (preferably acidic) solution in sub-step (b) of step (B.2) is also typically less than 100° C., e.g. from 70° C. to 90° C.

Preferably, either of the sulfide and/or sulfate salt comprised in the alkaline solution used in step (B.1) or the sulfite or bisulfite salt comprised in the aqueous preferably acidic solution in step (B.2) is a salt with a cationic counter ion preferably selected from the group consisting of sodium, calcium, magnesium and ammonium. The sulfhydryl and/or polysulfide agent employed by step (B.1) is preferably an organic, non-salt agent.

It is preferred that "cooking" in sub-step (c) of step (B.1) is carried out in a pressurized vessel ("digester") for at least 2 hours at a temperature of at least 150° C. Cooking in sub-step (c) of step (B.2) is carried out in a pressurized vessel for at least 3 hours at a temperature of at least 120° C. Under such conditions, pulp and modified lignin-derived components may be separated from each other. Sub-step (c) of either of step (B.1) or (B.2) may more preferably be carried out at a pressure of at least 4 bar in the pressurized vessel, preferably at 5 to 10 bar. A pressurized vessel is typically a digester as it is commonly used in the art of chemical pulping.

It is preferred that Kraft process sub-step (c) of step (B.1) is carried out at a temperature of 150 to 190° C., preferably 170 to 180° C. The sulfite process sub-step (c) of step (B.2) is preferably carried out at a temperature of 120 to 170° C., more preferably at a temperature of 130 to 160° C. Such temperatures typically provide higher yields (by improved separation of the lignin and the cellulosic fraction) and process efficiency. Increasing the temperatures significantly beyond 200° C., in particular in combination with the applied overpressure may lead to undesired excessive degradation of the lignin and/or the cellulosic fraction and is unfavorable in terms of the energy consumption involved.

Sub-step (c) of the Kraft process (B.1) is preferably carried out for 2 to 24 hours, preferably 3 to 5 hours. Sub-step (c) of the sulfite process (B.2) is preferably carried out for 4 to 24 hours, preferably 4 to 6 hours. Such conditions typically enable satisfying yields, while still ensuring overall process efficiency. Under such conditions of the Kraft process, lignin polymers and hemicellulose are sufficiently degraded, such that their lower molecular weight (lower than the starting material's natural lignin and hemicellulose) degradation products are released from the cellulose scaffold as a result of the cooking step. Such lower molecular weight degradation products are typically more soluble in (strongly) basic solution than the polymers of the lignocellulosic starting material.

Preferably, sub-step (c) of either step (B.1) or (B.2) is carried out either in a batch mode or in a continuous mode. For the continuous mode, the lignocellulosic starting material is fed into a digester at a rate, which allows the pulping reaction to be complete by the time the materials exit the reactor. The continuous mode is preferred to ensure higher throughput and improved efficiency. Digesters producing 1.000 tons or more of pulp per day are common and may be used according to the inventive method.

The lignin-derived fraction of any pulping process may be forwarded to separation step (C) for its further processing towards the low molecular weight target compound. In particular, "Kraft lignin" upon application of sub-steps (a) to (c) of the Kraft process in step (8.1), or "lignosulfonate" upon application of the sulfite process in step (B.2) or "sulfonated Kraft lignin" upon application of sub-steps (a) to (d) of the Kraft process in step (B.1) may be employed for further processing by step (C).

Further downstream, the method of the present invention employs the steps of separating pulp in step (C) from the process stream and, subsequently, isolating the fraction of modified lignin-derived components in step (D) from other components being present in the process stream.

Step (C) may be carried out by any suitable separation method preferably selected from the group consisting of blowing, sieving, countercurrent flow, centrifugation, filtration, washing, stripping, ion-exchange, or any combination thereof. Separation of the pulp from the process stream is more preferably carried out by blowing, sieving and/or washing.

Step (D), i.e. isolation of the fraction of modified lignin-derived components from other (e.g. hemicellulosic) components in the process stream, may preferably be carried out by filtration including ultra- and/or nanofiltration, extraction, countercurrent flow, stripping, ion-exchange, precipitation by di- or multivalent cations, such as calcium cations (which may e.g. be provided as calcium hydroxide), precipitation by $CO_2$ in acidic solution, or any combination of thereof. Preferably, isolation is carried out by any type of extraction or filtration, preferably ultrafiltration and/or nanofiltration.

Ultrafiltration and/or (depending on the size of the lignin-derived components to be isolated) nanofiltration may be preferably employed in step (D). Ultrafiltration typically employs a pore size of 2-100 nm and a molecular weight cut-off value of about 5 kDa. Nanofiltration typically refers to a filtration mode based on a pore size of 1-2 nm and a molecular weight cut-off value of 0.1-5 kDa. Accordingly, ultrafiltration is typically employed to separate or isolate larger lignin-derived components (e.g. larger than 5.000 Da, larger than 8.000 Da or larger than 10.000 Da) from the process stream (containing components of whatever e.g. the lignin-derived fraction or residual cellulosic fraction or the hemicellulosic fraction of a molecular weight of less than 5.000 Da). That isolated larger molecular weight fraction may be subject to further separation in order to separate larger isolated components of distinct fractions, e.g. to isolate the lignin-derived components from residual cellulosic degradation products or hemicellulosic components. The isolated lignin-derived fraction of the molecular weight retained by the chosen cut-off value of the ultrafiltration device may then be further proceed in step (D).

Also, the remaining components of the lignin-derived fraction in the process stream having a molecular weight lower than the cut-off level chosen for initial ultrafiltration may be isolated from other components in the process stream. E.g. the process stream may be subjected to another filtration step with a lower cut-off level than chosen for the initial ultrafiltration step, e.g. by additional lower cut-off level ultrafiltration and/or nanofiltration. Thereby, the lignin-derived components of a molecular weight lower than the cut-off-level of the first filtration step and larger than the cut-off level of the second filtration step may be isolated. That retained lignin-derived fraction may be subject to further isolation to separate the lignin-derived component fraction from components of similar size of other fractions (e.g. from hemicellulosic degradation products of similar size). Accordingly, the inventive method may be set up such that components of the lignin-derived fraction are isolated, which fall within the individually desired smaller molecular weight range of e.g. between 3.000, 4.000, 5.000 or 6.000 Da (cut-off level of the second filtration step) and 5.000, 6.000, 8.000 or 10.000 Da (cut-off level of the first filtration step). Thereby or by any other method known in the art to separate by molecular weight or by other physico-chemical parameters, a more homogeneous lignin-derived fraction may be forwarded to decomposition step (E). Accordingly, two ultrafiltration steps or ultrafiltration and nanofiltration, repectively, may e.g. be combined to arrive at a modified lignin-derived fraction of a defined molecular weight range (e.g. 5.000 to 10.000 or 1.000 to 5.000 Da, repectively for Kraft lignin). Whenever isolation from the process stream of the sulfite process-derived lignosulfonate is concerned, such isolation may preferably be performed by employing suitable isolation methods, e.g. as described by Lebo et al. (Lebo, Stuart E. Jr.; Gargulak, Jerry D.; McNally, Timothy J. (2001). "Lignin". Kirk-Othmer Encyclopedia of Chemical Technology. Kirk-Othmer Encyclopedia of Chemical Technology. John Wiley & Sons, Inc.), which is incorporated herein by reference. "Lignosulfonate" (due to the larger molecular weight of its components) will preferably be based on two ultrafiltration steps resulting e.g. in a molecular weight range of the isolated lignin-derived components of between 6.000 Da and 15.000 Da or 8.000 Da and 12.000 Da.

Ultra- and/or nanofiltration typically employ membranes, which are preferably tubular membranes exposing solvent resistance, i.e. which are preferably resistant at high and low pH values. Ultra- and/or nanofiltration is typically performed at elevated pressure, preferably above about 2 bar, more preferably at about 3 bar or above, even more preferably at about 4 bar or above, most preferably at about 5 bar. Higher pressures may also be applied, e.g. above 10 bar, such as between 10-15 bar. Further, the applied temperature for the filtration step is typically higher than room temperature (25° C.) to facilitate isolation of the fraction of modified lignin-derived components. Usually, the temperature is chosen such that degradation of the components to be isolated is essentially avoided. The temperature may be at least 40° C., preferably at least 50° C., most preferably about 60-65° C.

Hence, the preferred membrane's cut-off size of the employed ultra- or nanofiltration in step (D) may depend on the expected molecular weight of the target modified lignin-derived components. For example, Kraft lignin being of a relatively small molecular weight may require a membrane cut-off of about 2 to kDa or from 2 to 8 kDa, while larger lignosulfonate may require a membrane cut-off of about 5 to 50 kDa or even up to 100 kDa. Typically, the cut-off size for membranes to isolate lignosulfonate may be about 5 to 20 kDa.

If ultra- and/or nanofiltration is applied, it is preferably preceded by a pre-filtration step to separate larger debris, e.g. insoluble or poorly soluble polymers and/or fragments thereof. Thereby, efficiency may be increased as excessive blockade of the ultra- and/or nanofiltration membrane may be avoided, when isolating the fraction of modified lignin-derived components. Accordingly, the pre-filter typically has a larger pore size and/or molecular weight cut-off than the ultra- and/or nanofiltration membrane.

In a preferred embodiment of the present invention, step (E.1) comprises oxidizing the modified lignin derived-components, preferably in the presence of a heterogeneous or homogeneous catalyst or a combination of catalysts. Preferably oxidative cracking (cracking and oxidizing) of the modified lignin-derived components is performed. Oxidative cracking (cracking and oxidizing) is preferably carried out in a single reaction vessel, preferably simultaneously. "Cracking" and in particular "oxidative cracking (cracking and oxidizing)" and "reductive cracking (cracking and reducing)" as used herein preferably refers to one-step catalytic reactions to break or dissociate larger molecules into their smaller fragments by dissociation of covalent bonds of the larger molecule by oxidation ("oxidative cracking (cracking and oxidizing)") or reduction ("reductive cracking (cracking and reducing)"). Therein, the molecules are brought into contact with an aqueous solution comprising the catalysator (which may be dissolved or suspended therein).

The term "cracking" may also be used to refer to reactions developed for petrochemistry to disrupt larger e.g. gasoil molecules into smaller gasoline molecules and olefinsIn that context, "cracking" makes use of a reactor and a regenerator for regenerating the catalytic material. Therein, starting material may be injected into preferably hot, fluidized catalysts. The resulting vapor-phase products may be separated from the catalytic materials and fractionated into various product or product fragment fractions by condensation. The catalyst is typically introduced into a regenerator, wherein air or oxygen is preferably used to separate any residual components by an oxidation reaction, such that the surface of the catalyst is freed from any by-products, which are formed as a result of the cracking process. The hot regenerated catalyst may then be recycled to the reactor to complete its cycle. Modified lignin-derived products may be subjected to "cracking" conditions according to this definition as well, although the term "cracking" is preferably and typically to be understood as "oxidative cracking (cracking and oxidizing)" or "reductive cracking (cracking and reducing)" as defined above.

Advantageously, analogous cracking reactions may be applied to modified lignin-derived material of step (D) obtainable from renewable sources, according to the present invention.

Step (E.1) (Oxidative cracking (cracking and oxidizing)) is typically carried out in the presence of an oxidizing agent such as air, $O_2$ or $H_2O_2$ and preferably a catalyst or a mixture of catalysts, which is/are preferably of heterogeneous nature, e.g. with regard to a cracking reaction, but may also be of homogeneous nature. Homogenous and heterogenous catalysts of interest for oxidative cracking (cracking and oxidizing) in step (E.1) of the inventive method are exemplified above.

Preferably, the catalyst may comprise a metal ion, preferably selected from Co(II), Cu(II), Fe(II) and Fe(III), more preferably Fe(III). Alternatively, the catalyst may comprise a metalloid element. The "metalloid element" and/or the metal ion is/are preferably provided as coordination complex or, alternatively, as a salt. In such a coordination complex, a metalloid element or metal ion forms the coordination center. Typically, a "metalloid" is a chemical element with metallic and non-metallic properties. Metalloid may be any element selected from boron, silicon, germanium, arsenic, antimony, tellurium, aluminum, and selenium. A metalloid may have a metallic appearance, it is typically brittle and only a fair conductor of electricity. Chemically, it may behave mostly like a non-metal. Metalloid comprising agents are particularly useful as catalysts. Preferably, the metalloid catalyst comprises the metalloids B(III), Si(IV) and/or Al(III). The metalloid catalyst may preferably be a boron catalyst, comprising preferably B(III). As an example: When using a boron catalyst, step (E.1) may be a hydroboration-oxidation reaction, which is preferably a two-step organic reaction. It converts, e.g., an alkene into a neutral alcohol by the net addition of water to the double bond. The hydrogen and hydroxyl group are preferably added in syn addition providing an alcohol in cis stereochemistry. Hydroboration-oxidation typically reflects an anti-Markovnikov reaction, with the hydroxyl group being attached to the less-substituted carbon.

More preferably, the homogeneous catalyst in step (E.1) is selected from the group consisting of a salt, a coordination complex, a zeolite, a polyoxometalate, and a combination of any of them. Any such catalysts preferably comprises a metal ion selected from Co(II), Cu(II), Fe(II) and Fe(III), most preferably Fe(III). Specifically when using Cu(II)-based (homogenous or heterogenous) catalysts may be recovered e.g. by sulphide precipitation and subsequent filtration.

(Synthetic) zeolites are typically microporous, aluminosilicate minerals, which are known as adsorbents and catalysts. Zeolites are widely used as catalysts in the petrochemical industry, for instance in fluid catalytic cracking and hydrocracking. Zeolites may also be used as active catalytic solid-state acids in applications other than in petrochemistry. Hence, zeolites may facilitate numerous acid-catalyzed reactions, as they may be foreseen for the present invention. They may be employed as catalysts for the oxidative cracking (cracking and oxidizing) reaction e.g. of step (E.1) of the present inventive method.

Catalysts reflecting polyoxometalate(s) (POM(s)) are polyatomic ions, usually anions that may be composed of three or more transition metal oxyanions, which are linked together by shared oxygen atoms to form a closed 3-dimensional framework. POMs may advantageously be employed for oxidation of organic compounds, in particular for oxidation of the fraction of modified lignin-derived components isolated in step (D).

It is preferred that oxidative cracking (cracking and oxidizing) according to step (E.1) may be performed in the presence of a metal catalyst, in particular a Cu(II) or Fe(III) containing catalyst. Alternatively, a Co(II) comprising catalyst may be employed. The catalyst may be selected from a heterogeneous catalyst or a homogeneous catalyst. The metal catalyst, in particular the Cu(II) or Fe (III) containing catalyst, is preferably a (metal) salt.

The oxidative cracking (cracking and oxidizing) reaction is preferably carried out under elevated temperature and/or pressure conditions.

The reaction of step (E.1) may be carried out at a temperature of 30 to 400° C., preferably 100 to 350° C. The temperature chosen for that reaction is selected such that it is significantly lower than pyrolytic temperatures, e.g. lower than 1000° C. or 800° C. or lower than 500° C. By such a lower temperature reaction, the reaction products are typically less diverse than by a purely pyrolytic reaction (or pyrolytic decomposition).

For example, the solution comprising the fraction of modified lignin-derived components of step (D), e.g. lignosulfonate, is made alkaline, preferably by adjusting the pH value to at least 9. In another preferred embodiment, the medium may be acidic. The metal and/or metalloid catalyst, in particular the Fe(III) containing catalyst, may be added thereafter to that solution. Said catalyst comprising solution may be heated to a temperature of at least 150° C., preferable to a temperature of 150 to 300° C., more preferably 160-170° C. The pressure may be set to an overpressure of at least 5 atm, preferably from 10 to 12 atm. When applying such temperature and pressure conditions, cracking occurs and oxidizing may typically take place simultaneously due to the air's oxygen as oxidizing agent.

In contrast to employing air as oxidizing agent, step (E.1) employing a metal and/or metalloid catalyst, in particular the Cu(II) containing catalyst, may be conducted in an oxygen enriched environment, more preferably under increased pressure, in particular increased oxygen partial pressure. Said pressure may—preferably under alkaline conditions—be at least 3 bar $p(O_2)$, more preferably 4 to 5 bar $p(O_2)$. Under acidic conditions, the $p(O_2)$ may advantageously be at least 10 bar, sometimes at least 20 bar. Further advantageously, an alcohol, preferably methanol, may be added to the reaction to avoid re-polymerisation of the lignin-derived components.

The alcohol, preferably methanol, may be added in an amount of at least 5%, preferably at least 10%, more preferably at least 20%, even more preferably at least 30%, even more preferably at least 40%, even more preferably at least 50%, even more preferably at least 60%, even more preferably at least 70%, most preferably at least 80% with respect to the total reaction volume.

The alcohol, preferably methanol, may be recovered before or after isolation/purification of the target compound in step (F) of the inventive method. In the recovery step, the alcohol, in particular methanol, is preferably recovered by heating and vaporization. The recovery step is preferably performed after isolation step (F) of the inventive method.

The temperature is preferable at least 150° C., more preferably at least 170° C. The reaction may be carried out in solution under constant stirring, e.g. at about 10 rpm or above, preferably at about 50 rpm or above, e.g. at about 100 rpm, or even higher, e.g. at least 500 rpm, or 1.000 rpm, depending inter alia on the size of the reactor. Said oxidation in the presence of an oxygen environment may be performed in a fluidized bed reactor, particularly a reactor comprising a sand bed, or a plug flow reactor, wherein use of a plug flow reactor may be preferred. Under such conditions, the temperature may be set to at least 250° C., preferably to at least 300° C. Thereby, the oxidation rate may advantageously be increased. Upon application of a fluidized bed reactor, less desired or undesired by-products other than the target aromatic or phenolic compounds are preferably less frequently observed, which is preferred for step (E) of the inventive method.

In the alternative, decomposition in step (E) may be carried out by reductive cracking (cracking and reducing) of the fraction of modified lignin-derived components isolated in step (D), which is carried out in the presence of a reducing agent (alternative E.2). The reducing agent is preferably hydrogen or an alcohol as H-donor. Such a reaction under reducing conditions typically also requires a heterogeneous catalyst comprising, e.g., a metal selected from nickel, platinum, palladium, ruthenium, rhenium and gold. The catalyst is preferably provided on the surface of a support material preferably selected from the group consisting of active carbon, silica, titaniumoxide and/or aluminumoxide. Thereby, the lignin-derived components may be subject to e.g. hydrogen based "lysis" by cleavage of carbon-carbon or carbon-heteroatom single bonds (hydrogenolysis).

For example, reductive cracking (cracking and reducing) of the fraction of modified lignin-derived components isolated in step (D) may be carried out by means of a catalyst comprising nickel, e.g. supported on activated carbon (Ni/C). Therein, a fragmentation-hydrogenolysis process of the modified lignin into lower molecular weight lignin-derived target compounds, e.g. di- or monomeric phenolic target compounds, in alcoholic solvents over nickel-based catalysts may be performed. This reaction involves hydrogenolysis of modified lignin components into di- or monomeric phenolic compounds over nickel catalysts, wherein alcohol is preferably the source of active hydrogen as the reducing agent.

In an alternative example, the fraction of modified lignin-derived components from step (D) may be preferably cracked and reduced in the presence of Ruthenium deposited on a carbon catalyst (Ru/C) in preferably an organic solvent, such as methanol, under a reducing atmosphere, such as an $H_2$ atmosphere, preferably at elevated temperatures. Such a reaction preferably provides, other than residual carbohydrate pulp, lignin oil. The resulting phenol-rich lignin oil typically consist more than 50% (w/w) of phenolic monomers as target compounds of the present invention (mainly) and 10% to 25%, preferably less than 20% (w/w) of phenolic dimers. The obtainable target compounds by that reaction (or alternative reactions) are one or more of syringol, in particular 4-n-propylsyringol, 4-ethylphenol, and guaiacol, in particular 4-ethylguaiacol and 4-n-propylguaiacol.

In an alternative embodiment of the present invention, steps (B) (degradation) and (E) (decomposition) may be combined, which does preferably not require steps (C) and (D). The combined degradation/decomposition reaction (steps (B) and (E) combined) mode of the inventive method may preferably, but not necessarily be carried out by employing step (E.2) according to the inventive method. Therein, the natural lignocellulosic material provided in step (A) may be delignified through simultaneous solvolysis and catalytic hydrogenolysis of the lignin material in one single step. Combined solvolysis and catalytic hydrogenolysis may preferably be carried out in the presence of Ruthenium preferably deposited on a carbon catalyst (Ru/C), preferably in an organic solvent, such as methanol, under a reducing atmosphere, such as an $H_2$ atmosphere. The reaction is preferably carried out at elevated temperatures. The resulting product of combined solvolysis and catalytic hydrogenolysis may be further processed as described herein to obtain a purified fraction of low molecular weight aromatic lignin-derived (mono- or dimeric) compounds.

Finally, decomposition in step (E) may be carried out by electro-oxidation (alternative E.3). "Electro-oxidation" is defined as an electrochemical process, wherein the oxidation reaction occurs by applying an electric field between two electrodes, e.g. a working electrode and a counter electrode, for the oxidation reaction to take place. The "working electrode" (electrode in an electrochemical system, on which the reaction of interest takes place) is cathodic or anodic, respectively, depending on whether the reaction on the electrode is reduction or oxidation. Common working electrodes may comprise inert metals, such as gold, silver or platinum, or inert carbon, such as glassy carbon or pyrolytic carbon, or mercury drop and film electrodes. The working electrode employed by the present invention may alternatively also be a nickel or nickel alloy electrode. The counter electrode may be a platinum electrode, in particular whenever the working electrode is a nickel electrode. The electrodes may be, for example, sintered electrodes, which preferably benefit from extended life time and show a higher oxidation capacity than other technologies. Electro-oxidation may be advantageous, as it provides instant operation on demand ("on/off"). Further, no aggressive chemicals are required, and reaction temperatures may be kept low. As the large diversity of by-products is avoided, it allows to efficiently produce lower molecular weight aromatic lignin-derived target compounds. As compared to thermal decomposition methods, energy consumption is reduced.

The electro-oxidation reaction may preferably performed in strong alkaline solution of at least pH 10, and preferably, constant current is applied. Preferred is electro-oxidation carried out galvanostatically at pH 10 to 14. Preferably, the solution comprising the modified lignin-derived components, e.g. lignosulfonate, acts as anolyte and, typically, NaOH solution as catholyte. In general, an anolyte is the part of the electrolyte, which is under direct influence of the anode upon electrolysis. Correspondingly, a catholyte is the part of the electrolyte, which is under direct influence of the cathode upon electrolysis. Alternatively, electro-oxidation may preferably also be carried out under acidic conditions. Further, the modified lignin-derived components in solution may serve as anolyte and catholyte at the same time. Advantageously, no (semi-permeable) membrane is required for the inventive method. In terms of the electrolyte, no specific electrolyte is required, if the reaction is carried out in acidic or alkaline medium. Alternatively or additionally, a salt or distinct salts, preferably an alkali salt, may be added to the electrolyte, e.g. a sodium salt, preferably sodium sulfate. Electro-oxidation may also directly yield the target compounds (e.g. quinones). In such cases, the isolation/purification step (F) may be omitted.

In another embodiment, decomposition may alternatively be accomplished by biotechnological means, e.g. by enzymatic degradation of lignin. Therein, typically cellulose and hemicellulose are degraded, and low molecular weight lignin-derived components may advantageously be obtained by chemical decomposition. They may be isolated from the cellulosic and hemicellulosic fraction by the means disclosed herein.

Finally, isolation step (F) of the inventive method is another purification and isolation step, which may preferably comprise filtration and/or extraction, preferably filtration. Filtration may be selected from ultrafiltration and nanofiltration, which may be carried out by an ultrafiltration and/or nanofiltration cell, preferably having a pre-filtration section for increasing the efficiency of the filtration step (e.g. avoidance of membrane blockade, e.g. by higher molecular weight lignin-derived components). Stirred ultrafiltration cells as described by Duval et al. (Holzforschung 2015, 69, 127-134) may be applied as well. Preferably, the ultrafiltration and/or nanofiltration cell comprises at least one molecular weight cut-off unit, preferably at least two molecular weight cut-off units allowing to isolate target compounds within a molecular weight range, which reflects the molecular weight of monomeric and dimeric target compounds, e.g. from 150 Da to 1.000 Da or from 150 to 500 Da. Preferably, a cascade of cut-off units (e.g. strating with one or more ultrafiltration cell(s) and one or more subsequent nanofiltration cell(s) with preferably decreasing cut-off values may be employed to fractionate the resulting lignin-derived decomposition products obtained in step (E). The decomposition products obtained in step (E) may usually be fractionated in solution or may be isolated as dried matter and be re-dissolved thereafter, if required.

Preferably, the ultra- and/or nanofiltration may be followed by further purification steps to increase purity of the lower molecular weight aromatic lignin-derived target compound according to the present invention. For example, diafiltration against water may be used to remove residual sugars and reactive agents from the low molecular weight target compound fraction. Alternatively, the low molecular weight target compounds may be isolated by extraction, optionally followed by fractional distillation.

By a second aspect, the present invention refers to low molecular weight lignin-derived compounds, which are obtainable by a method according to the first aspect.

Preferably, the target compound obtained by step (F) of the inventive method comprises one or two aromatic (carbocyclic) ring(s), separated by a linker or directly linked by a bond (biphenylic compound). A target compound comprising one aromatic ring is typically derived from a monomer of the modified lignin precursor component as the intermediate of the inventive method. A target compound comprising two aromatic rings is typically derived from two covalently linked monomers (dimer) of the modified lignin precursor component as the intermediate of the inventive method.

Target compounds containing two aromatic rings, which form a biphenylic system, are obtainable by choosing the appropriate lignocellulosic starting material, which encompasses such moieties, e.g. from spruce. Such a biphenylic system typically comprises phenylbenzene or 1,1'-biphenyl as essential chemical structure. Biphenylic moieties are typically formed by 5-5-linkage of natural lignin monomers. Such a bond occurs more frequently in softwood than in hardwood. For example, spruce may comprise more than 15%, preferably more than 20%, even more preferred more than 25% biphenylic moieties among its phenyl-propane units making up its natural lignin. Whenever biphenylic target compounds are envisaged, it may be preferred to use spruce wood as a lignocellulosic starting material in step (A) of the inventive method. Biphenylic low molecular weight compounds may be further processed by chemical reactions, e.g. in further oxidizing reactions, in order to provide e.g. redox active compounds for multiple beneficial uses.

The aromatic ring(s) of the low molecular weight aromatic lignin-derived compound is/are substituted in at least one, preferably in at least two positions by a functional group, wherein the at least one functional group is preferably alkoxy or hydroxyl. Therein, a monocyclic compound is typically substituted in at least two positions by a functional group, wherein the functional group is preferably alkoxy or hydroxyl. A compound having two ring systems, in particular a biphenylic compound, is typically substituted in at least one position per aromatic ring by a functional group. Preferably, each ring system exhibits its individual substitution pattern being different from the other substitution pattern of the other ring system. Preferably, the at least one functional group is alkoxy or hydroxyl.

In particular, the at least one low molecular weight aromatic lignin-derived compound of the invention is characterized by general Formula (Ia):

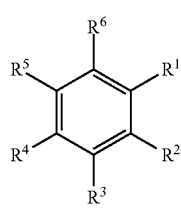

(Ia)

wherein
each of $R^1$-$R^5$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl;
   wherein at least one of $R^1$, $R^3$ or $R^5$ is preferably hydroxy or linear or branched, optionally substituted, $C_{1-6}$ alkoxy; and
   $R^6$ is selected from the group consisting of hydrogen, hydroxy, linear or branched, optionally substituted, $C_{1-6}$ carboxyl, linear or branched, optionally substituted, $C_{1-6}$ aldehyde, and linear or branched, optionally substituted, $C_{1-6}$ alcohol.

Or the at least one low molecular weight aromatic lignin-derived compound is characterized by general Formula (Ib):

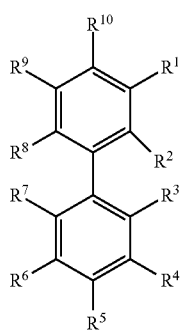

(Ib)

each of $R^1$-$R^9$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl;
   wherein $R^5$ is preferably hydroxy or optionally substituted $C_{1-6}$ alkoxy; and
   $R^{10}$ is selected from the group consisting of hydrogen, hydroxy, linear or branched, optionally substituted, $C_{1-6}$ carboxyl, linear or branched, optionally substituted, $C_{1-6}$ aldehyde, and linear or branched, optionally substituted, $C_{1-6}$ alcohol.

Alternatively, the at least one low molecular weight aromatic lignin-derived compound of the invention may be characterized by general Formula (Ia):

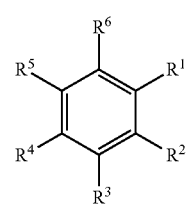

(Ia)

wherein
each of $R^1$-$R^5$ is independently selected from H, optionally substituted $C_{1-6}$ alkyl, optionally substituted $C_{1-6}$ alkenyl, halogen, optionally substituted $C_{1-6}$ alkoxy, amino, nitro, phosphoryl, and phosphonyl; wherein preferably at least one of $R^1$, $R^3$ or $R^5$ is hydroxy or optionally substituted $C_{1-6}$ alkoxy; and
   $R^6$ is selected from the group consisting of hydrogen, hydroxy, linear or branched $C_{1-6}$ carboxyl, linear or branched $C_{1-6}$ aldehyde, and linear or branched $C_{1-6}$ alcohol.

Or the at least one low molecular weight aromatic lignin-derived compound is characterized by general Formula (Ib):

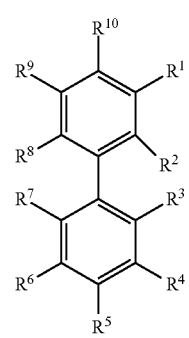

(Ib)

each of $R^1$-$R^9$ is independently selected from H, optionally substituted $C_{1-6}$ alkyl, optionally substituted $C_{1-6}$ alkenyl, halogen, optionally substituted $C_{1-6}$ alkoxy, amino, nitro, phosphoryl, and phosphonyl; wherein $R^5$ is preferably hydroxy or optionally substituted $C_{1-6}$ alkoxy; and
   $R^{10}$ is selected from the group consisting of hydrogen, hydroxy, linear or branched $C_{1-6}$ carboxyl, linear or branched $C_{1-6}$ aldehyde, and linear or branched $C_{1-6}$ alcohol.

As used herein, "Hydrogen" is H. "Hydroxy" or "Hydroxyl" is —OH. "Carboxy" or "carboxyl" is preferably —COOH. An exemplary ion of carboxy is —COO⁻. The term "alkyl" refers to a saturated aliphatic groups, including linear (straight-chain) and branched alkyl groups, cycloalkyl (alicyclic) groups, alkyl substituted cycloalkyl groups, and cycloalkyl substituted alkyl groups. The term "alkenyl" refers to unsaturated aliphatic groups analogous in length and possible substitution to the alkyls described above, but that contain at least one C—C double bound. The term "alkoxy" or "alkoxyl" refer to an alkyl group, as defined above, having an oxygen radical attached thereto. Representative alkoxyl groups include methoxy, ethoxy, propyloxy, tert-butoxy and the like. "Alkoxy" thus preferably refers to a group of formula —OR, wherein R is preferably an alkyl group, as defined herein. The term "aldehyde" refers to a group of formula —RCHO, wherein R is preferably selected from H or an alkyl group as defined above. "Halogen" is fluoro, chloro, bromo, or iodo. The terms "amine" and "amino" refer to both unsubstituted and substituted amines, i.e. groups of formula —NR$^1$R$^1$R$^3$, wherein R$^1$, R$^2$ and R$^3$ are independently selected from H and an alkyl group or another functional group.

The term includes "amino" (—NH$_2$). An exemplary ion of amino is —NH$_3^+$. The term further includes primary amines, wherein one of R$^1$, R$^2$ and R$^3$ is an alkyl group or other functional group. The term further includes secondary amines, wherein two R$^1$, R$^2$ and R$^3$ are independently selected from an alkyl group or other functional group. The term further includes tertiary amines, wherein all of R$^1$, R$^2$ and R$^3$ are independently selected from an alkyl group or other functional group. The term "amide" refers to a group of formula —RC(O)NR$^1$R$^2$, wherein R$^1$ and R$^2$ are independently selected from H, alkyl, or alkenyl. "Nitro" is —NO$_2$. "Oxo" is =O. The term "carbonyl" refers to a group of the formula —R$^1$C(O)R$^2$, wherein R$^1$ and R$^2$ are independently selected from nothing, a bond, H, O, S, alkyl, or alkenyl. "Phosphoryl" is —PO$_3$H$_2$. Exemplary ions of phosphoryl are —PO$_3$H— and —PO$_3^{2-}$. "Phosphonyl" is —PO$_3$R$_2$, wherein each R is independent H or alkyl, as defined herein. An exemplary ion of phosphoryl is —PO$_3$K. "Cyanide" is —CN. "Sulfonyl" is —SO$_3$H. An exemplary ion of sulfonyl is —SO$_3$—.

Preferably, the at least one low molecular weight aromatic lignin-derived compound is selected from the group consisting of phenolic derivatives of biphenyl, benzylalcohol, benzalde-hydes and benzoic acid, preferably derivatives of p-hydroxy benzylalcohol, p-hydroxy benzaldehydes and p-hydroxy benzoic acid, or more preferably vanillin, guaiacol, eugenol, syringol, phenol, syringaldehyde, and/or a derivative of any of the above, and/or a combination of the above.

Preferred are the low molecular weight aromatic lignin-derived compounds, which are represented by the following structures and corresponding esters:

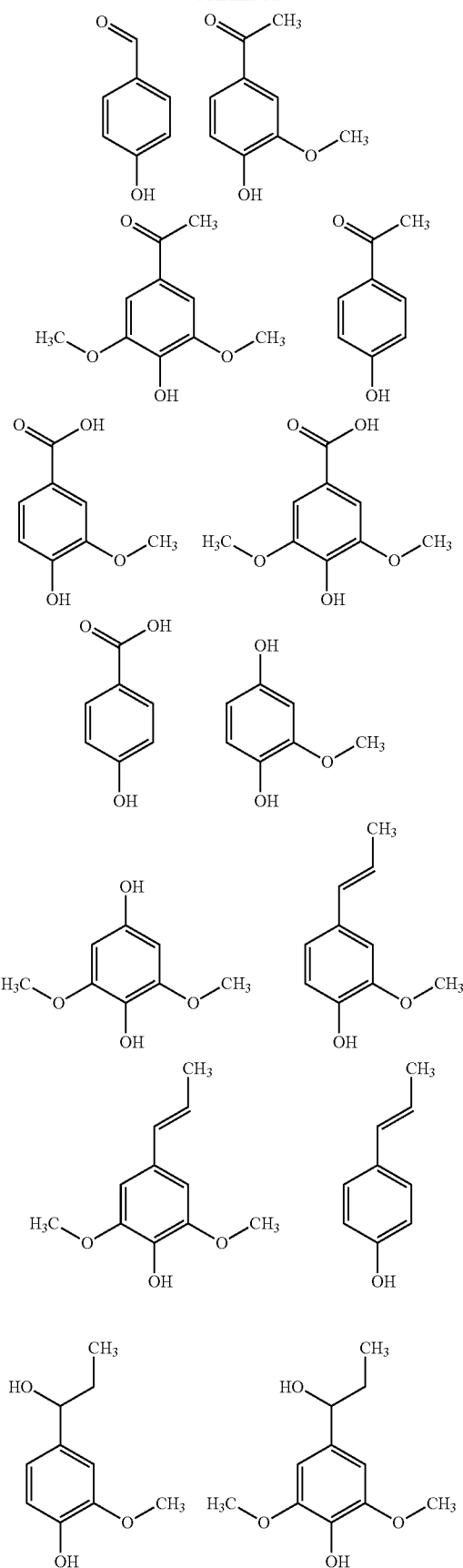

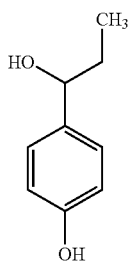

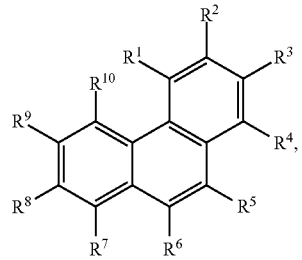

In a preferred embodiment of the second aspect according to the present invention, a monocyclic compound provided by step (F) is further reacted in a step (G) to an aromatic bi- or tricyclic compound, to a tetracyclic or pentacyclic compound. Annulated bicyclic or pentacyclic compounds may be preferred. They may be purified and further processed according to the present invention.

Such an aromatic annulated compound comprising more than one ring is of particular value as a precursor for further oxidation.

Said reaction type is typically known as annulation, which serves in organic chemistry as a chemical reaction, which allows to anneal two aromatic (mono-, di- or n-aromatic) ring systems. Preferably, the two or more precursor molecules of the annulation reaction are both or all e.g. monomeric or dimeric target compounds. The annulation is, for example, achieved by a Diels-Alder reaction or a Friedel-Crafts acylation.

Preferably, the at least one low molecular weight aromatic lignin-derived compound provided by step (F) comprises one aromatic ring and is further processed in a step (G), wherein said low molecular weight aromatic lignin-derived compound comprising one aromatic ring is subjected to an annulation reaction, preferably a Diels-Alder reaction or a Friedel-Crafts acylation, wherein the annulation reaction product is a low molecular weight aromatic bi- or tricyclic annulated aromatic lignin-derived compound, wherein said compound is characterized by general Formula (II), (III) or (IV)

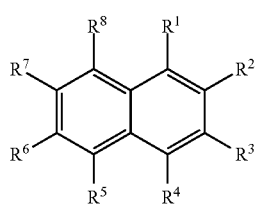

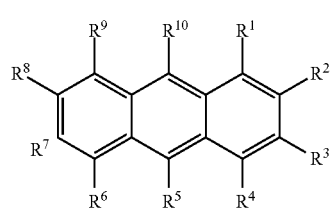

wherein
each of $R^2$, $R^3$, $R^5$-$R^8$ of Formula (II) is independently selected from hydrogen, hydroxy, carboxy, linear or branched, optionally substituted, $C_{1-6}$ alkyl, linear or branched, optionally substituted, $C_1$ alkenyl, linear or branched, optionally substituted, $C_1$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl, wherein preferably at least one of $R^2$, $R^3$, $R^5$-$R^8$ is hydroxy or $C_{1-3}$ alkoxy, and $R^1$ and $R^4$ of Formula (II) is/are selected from the group consisting of hydrogen, hydroxy, linear or branched, optionally substituted, $C_{1-6}$ carboxyl, linear or branched, optionally substituted, $C_{1-6}$ aldehyde, and linear or branched, optionally substituted, $C_{1-6}$ alcohol, each of $R^1$-$R^{10}$ of Formula (III) is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl, wherein preferably at least one of $R^2$, $R^5$, $R^6$ and $R^8$ is hydroxy or $C_{1-3}$ alkoxy, and wherein preferably $R^1$, $R^4$, $R^9$ and $R^{10}$ of Formula (III) is/are selected from the group consisting of hydrogen, hydroxy, linear or branched, optionally substituted, $C_{1-6}$ carboxyl, linear or branched, optionally substituted, $C_{1-6}$ aldehyde, and linear or branched, optionally substituted, $C_{1-6}$ alcohol, each of $R^2$, $R^3$ and $R^7$-$R^{10}$ of Formula (IV) is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl, wherein preferably at least one of $R^2$, $R^3$ and $R^7$-$R^{10}$ is hydroxy or $C_{1-3}$ alkoxy, and $R^1$, $R^4$, $R^5$ and $R^6$ of Formula (IV) is selected from the group consisting of hydrogen, hydroxy, linear or branched, optionally substituted $C_{1-6}$ carboxyl, linear or branched, optionally substituted, $C_{1-6}$ aldehyde, and linear or branched, optionally substituted, $C_{1-6}$ alcohol.

Alternatively, the at least one low molecular weight aromatic lignin-derived compound provided by step (F) comprises one aromatic ring and is further processed in a step (G), wherein said low molecular weight aromatic lignin-derived compound comprising one aromatic ring is subjected to an annulation reaction, preferably a Diels-Alder reaction or a Friedel-Crafts acylation, wherein the annulation reaction product is a low molecular weight aromatic bi- or tricyclic annulated aromatic lignin-derived compound, wherein said compound is characterized by general Formula (II), (III) or (IV)

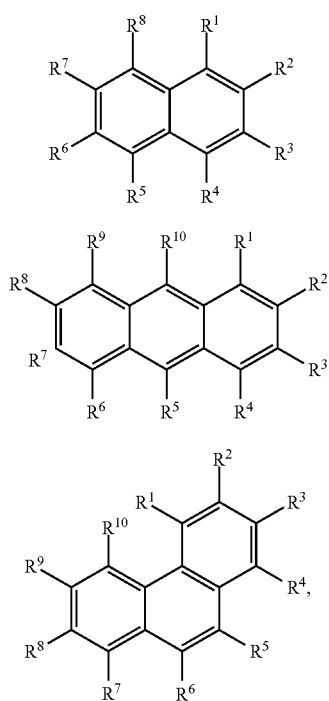

wherein
each of $R^2$-$R^7$ of Formula (II) is independently selected from H, optionally substituted $C_{1-6}$ alkyl, optionally substituted $C_{1-6}$ alkenyl, halogen, optionally substituted $C_{1-6}$ alkoxy, amino, nitro, phosphoryl, phosphonyl, wherein at least one of $R^2$, $R^4$, $R^5$, and $R^7$ is hydroxy or $C_{1-3}$ alkoxy, and $R_1$ and/or $R_8$ of Formula (II) is/are selected from the group consisting of hydrogen, hydroxy, linear or branched, $C_{1-6}$ carboxyl, linear or branched $C_{1-6}$ aldehyde, and linear or branched $C_{1-6}$ alcohol, each of $R^2$-$R^8$ of Formula (III) is independently selected from H, optionally substituted $C_{1-6}$ alkyl, optionally substituted $C_{1-6}$ alkenyl, halogen, optionally substituted $C_{1-6}$ alkoxy, amino, nitro, phosphoryl, phosphonyl, wherein at least one of $R^2$, $R^4$, $R^5$, $R^6$ and $R^8$ is hydroxy or $C_{1-3}$ alkoxy, and $R^1$, $R^9$ and/or $R^{10}$ of Formula (III) is/are selected from the group consisting of hydrogen, hydroxy, linear or branched $C_{1-6}$ carboxyl, linear or branched $C_{1-6}$ aldehyde, and linear or branched $C_{1-6}$ alcohol, each of $R^2$-$R^9$ of Formula (IV) is independently selected from H, optionally substituted $C_{1-6}$ alkyl, optionally substituted $C_{1-6}$ alkenyl, halogen, optionally substituted $C_{1-6}$ alkoxy, amino, nitro, phosphoryl, phosphonyl, wherein at least one of $R^2$, $R^4$, $R^7$, and $R^9$ is hydroxy or $C_{1-3}$ alkoxy, and $R^1$ and/or $R^{10}$ of Formula (IV) is selected from the group consisting of hydrogen, hydroxy, linear or branched $C_{1-6}$ carboxyl, linear or branched $C_{1-6}$ aldehyde, and linear or branched $C_{1-6}$ alcohol.

Preferably, the annulation reaction is a Friedel-Crafts acylation. This is particularly surprising as such acylation reactions were previously known preferably in the petrochemical field with regard to annulation reactions. Transferring said annulation reaction to compounds according to the present invention from renewable sources opens new synthesis options.

Friedel-Crafts acylation is the acylation of aromatic rings with an acyl chloride using a strong Lewis acid catalyst. Friedel-Crafts acylation is also possible with acid anhydrides. This reaction typically involves the acylation of an aromatic ring with an alkyl halide using a strong Lewis acid catalyst, e.g. an anhydrous ferric chloride as a catalyst.

In the context of the present invention, a Diels-Alder reaction is understood as an organic chemical reaction, typically a [4+2] cycloaddition, between a conjugated diene and a substituted alkene, commonly termed the dienophile, to form a substituted cyclohexene system. Said formed cyclohexene system is preferably aromatic. The Diels-Alder reaction is particularly useful in synthetic organic chemistry as a reliable method for forming 6-membered systems with good control over regio- and stereochemical properties.

In a preferred embodiment of the present invention, monocyclic compounds comprising only one aromatic ring may be subjected to reactions, which increase the number of aromatic ring. Hence, the respective compound undergoes annulation. Generally, an "annulation" in organic chemistry is a chemical reaction, in which a new ring is constructed on another molecule, typically another ring. For example, through the conduction of a Diels-alder reaction, a monocyclic compound provided by step (F) of the present invention may be extended to a bicyclic, tricyclic, tetracyclic or even higher n-cyclic compound. Without wanting to be bound by theory, it is believed that compounds with increased annulation are advantageous as further processed redox active compounds. For example, anthracene derivatives, which may be precursors for anthraquinone-derivatives, are preferred in the context of the present invention as they show that redox potentials decrease with increased annulation and, thus, the more annulated derivatives are more stable. This is of particular importance for compounds, which—according to a further aspect of the present invention—are preferably oxidized to a redox active compound for versatile use, which compound advantageously requires a long operational life to be fit for practice. By providing redox active compounds of increased stability, this important practical demand is met. With an appropriate selection of a diene, it is possible to convert less stable benzoquinone structures to naphthacenes, anthracene and/or phenanthrenes. The fusion of a benzene ring onto an existing monocyclic compound according to the present invention, preferably an oxidized compound such as quinone, may be accomplished on a ring which has two adjacent positions unsubstituted or substituted. However, unsubstituted positions are generally preferred due to higher yields. Hence, it is preferred in the context of the present invention that if a compound of more than one aromatic ring is desired, compounds are preferably subjected to further substitution reactions only after the annulation reaction was performed. It may be further advantageous in large-scale reactions to add one or more polymerization inhibitors known in the art. The Diels-alder reaction may be catalysed by any suitable catalyst known in the art, preferably by one or more metallic chlorides and/or zeolites. The subsequent oxidation step may or may not be necessary. If a reduced catalyst is still present from earlier reaction steps, the newly annulated ring may be instantly oxidized and aromatized, yielding in a multi-ring quinone. Alternatively, aeration in alkaline solution may be used, e.g., to obtain an anthraquinone derivative.

The condensation is preferably carried out prior to the optional downstream oxidation to obtain a redox active compound, or prior to derivatization in order to avoid, e.g. steric hindrance, and, in consequence, lower yields in condensed and derivatized product. Derivatization as used herein with regard to the compounds obtainable from step (F) or (G) aims to improve solubility and electrochemical properties.

It is a preferred embodiment of the present invention, that the at least one low molecular weight aromatic lignin-derived compound obtained from step (F) (or (G)) is further modified in a step (H) by oxidizing the at least one low molecular weight aromatic lignin-derived compound in the presence of (i.) an oxidizing agent selected from the group consisting of $H_2O_2$, $O_2$ and air and (ii.) a heterogeneous catalyst comprising a metal ion or a metalloid, or performing homogeneous catalysis in the presence of NaOH. In said preferred embodiment, usually no catalyst comprising a metal ion or a metalloid is required.

In one embodiment of the present invention, Co(II) complexes are employed because they have a high selectivity towards quinones. For example, (pyr)Co(II)salen may be employed in the presence of $O_2$ at overpressure, e.g. at least 3 bar. Such a reaction may preferably be conducted at room temperature in an organic solvent such as MeOH. Other preferred catalysts are Co(3-methoxysalen) and Co(N—N-Me salpr). In the latter case, the preferred organic solvent may be $CH_2Cl_2$. Said oxidation provides an oxidized low molecular weight aromatic lignin-derived compound, which is generally understood herein as hydroquinone compound according to the present invention and/or, upon further oxidation, as a quinone compound according to the present invention.

Preferably, step (H) provides at least one hydroquinone compound (step H.1), characterized by general Formula (Va):

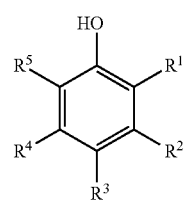

(Va)

wherein each of $R^1$-$R^5$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl and wherein one of $R^1$, $R^3$ and $R^5$ is hydroxy; or by general formula (Vb),

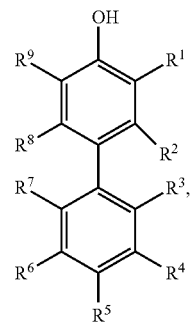

(Vb)

wherein each of $R^1$-$R^9$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl, and wherein $R^5$ is preferably hydroxy.

Said hydroquinone compound is preferably a redox active material, which may be beneficial in a variety of uses.

In a particularly preferred embodiment, step (H) provides at least one quinone compound (step H.2) under harsher oxidation conditions than in step (H.1), characterized by any of general Formulae (VIa) to (VIb):

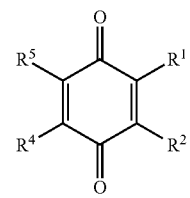

(VI a)

wherein each of $R^1$-$R^2$ and $R^4$-$R^5$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl; or

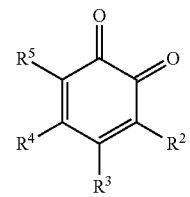

(VI b)

wherein each of $R^2$-$R^5$ is independently selected from hydrogen, hydroxy, carboxy, linear or branched, optionally substituted, $C_{1-6}$alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl; or

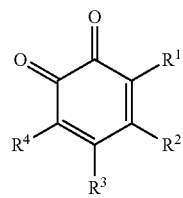

(VIc)

wherein each of $R^1$-$R^4$ is independently selected from hydrogen, hydroxy, carboxy, linear or branched, optionally substituted, $C_{1-6}$alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl; or

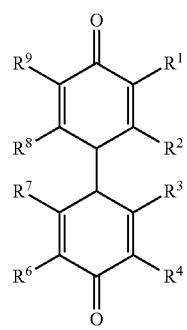

(VId)

wherein each of $R^1$-$R^4$ and $R^6$-$R^9$ is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl.

Alternatively, step (H) may provide at least one hydroquinone compound (step H.1), characterized by general Formula (Va):

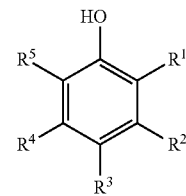

(Va)

wherein each of $R^1$-$R^5$ is independently selected from optionally substituted $C_{1-6}$ alkyl, optionally substituted $C_{1-6}$ alkenyl, halogen, optionally substituted $C_{1-6}$ alkoxy, amino, carboxyl, nitro, phosphoryl, and phosphonyl, and wherein one of $R^1$, W and $R^5$ is hydroxy; or by general formula (Vb),

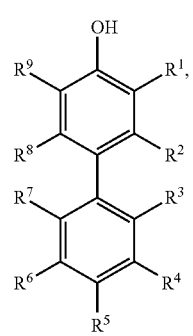

(Vb)

wherein each of $R^1$-$R^9$ is independently selected from optionally substituted $C_{1-6}$ alkyl, optionally substituted $C_{1-6}$ alkenyl, halogen, optionally substituted $C_{1-6}$ alkoxy, amino, carboxyl, nitro, phosphoryl, and phosphonyl; and wherein $R^5$ is hydroxy.

Said hydroquinone compound is preferably a redox active material, which may be beneficial in a variety of uses.

In a particularly preferred embodiment, step (H) provides at least one quinone compound (step H.2) under harsher oxidation conditions than in step (H.1), characterized by any of general Formulae (Via) to (VIb):

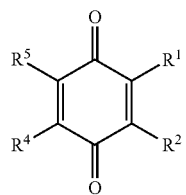

(VIa)

wherein each of $R^1$-$R^2$ and $R^4$-$R^5$ is independently selected from optionally substituted $C_{1-6}$ alkyl, optionally substituted $C_{1-6}$ alkenyl, halogen, optionally substituted $C_{1-6}$ alkoxy, amino, carboxyl, nitro, phosphoryl, and phosphonyl; or

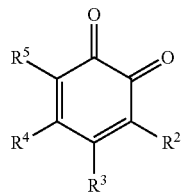

(VI b)

wherein each of $R^2$-$R^5$ is independently selected from optionally substituted $C_{1-6}$ alkyl, optionally substituted $C_{1-6}$ alkenyl, halogen, optionally substituted $C_{1-6}$ alkoxy, amino, carboxyl, nitro, phosphoryl, and phosphonyl; or

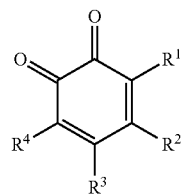

(VI c)

wherein each of $R^1$-$R^4$ is independently selected from optionally substituted $C_{1-6}$ alkyl, optionally substituted $C_{1-6}$ alkenyl, halogen, optionally substituted $C_{1-6}$ alkoxy, amino, carboxyl, nitro, phosphoryl, and phosphonyl; or

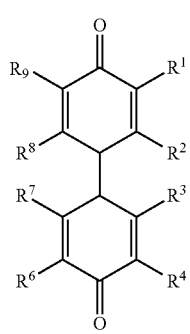

(VI d)

wherein each of $R^1$-$R^4$ and $R^6$-$R^9$ is independently selected from H, optionally substituted $C_{1-6}$ alkyl, halogen, optionally substituted $C_{1-6}$ alkoxy, amino, nitro, carboxyl, phosphoryl, and phosphonyl.

Preferably, the at least one hydroquinone compound provided by step (H.1) is further oxidized, preferably in the cell stack of a battery or by an oxidant, optionally in the presence of a heterogeneous catalyst, in a step (I) to obtain a quinone compound characterized by any of Formulas (VI a) to (VI d) as defined herein. Usually, it is sufficient to provide a hydroquinone compound according to the present invention, which compound already is redox active and may be oxidized or a part of the total amount of employed molecules of said hydroquinone compound may get oxidized.

In a preferred embodiment, step (H) and optionally step (I) provide a compound represented by one or both of the following structures:

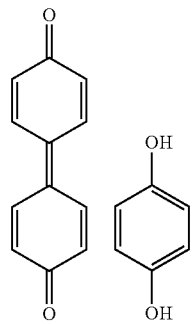

In another preferred embodiment, steps (E) and (H) of the inventive method may be combined together in one step. Therein, for example, (cracking and) oxidizing of a modified lignin-derived component (typically alternative (E.1) or (E.3)) takes place, and instantaneously or concurrently, the component is oxidized to a hydroquinone and/or quinone compound according to the present invention. Advantageously, said combination may save time and resources in terms of reactants, reactive agents and/or process equipment and apparatus means. Accordingly, such a combination lead to significant more economic and simple method for producing redox active compounds of renewable origin such as the hydroquinone and/or quinone compounds according to the present invention. Such a combined method step is preferably facilitated by applying electrooxidation of step (E.3), but catalyst-facilitated oxidation under (E.1) may also be applied. Preferred is electrooxidation, wherein direct oxidation from a modified lignin such as lignosulfonate to a hydroquinone and/or quinone compound is controlled by the respective set electrochemical conditions. Preferably, the modified lignin is diluted to a concentration below 20% (w/w), preferably below 10% (w/w), more preferably below 5% (w/w), even more preferably below 2% (w/w). The solution may have a pH of 1 to 14. Preferred is electrooxidation under acidic conditions. Alternatively, under alkaline conditions, the preferred pH is at least 11, more preferably at least 13. The electrooxidation is preferably conducted in a flow cell, wherein the flow is at least corresponding to 1 ml/min, preferably 10 ml/min or 50 ml/min, more preferably at least 200 ml/min, but may be up-scaled to significantly higher flows. Electrolysis may typically be conducted galvanostatically, preferably for at least 10 min, preferably at least 30 min, alternatively for at least 1 hour, preferably for at least 4 hours. Most preferred is a time period for conducting electrolysis of at least 30 min, e.g. to save time and resources. Preferably, electrolysis is carried out by applying a current of preferably at least 0.5 mA/cm$^2$, more preferably 1 mA/cm$^2$, even more preferably at least 5, 10 or 100 mA/cm$^2$.

It is also preferred that the low molecular weight aromatic bi- or tricyclic annulated compound obtained from step (G) is further modified in a step (H) by oxidizing the at least one low molecular weight aromatic bi- or tricyclic annulated compound in the presence of (i.) an oxidizing agent selected from the group consisting of $H_2O_2$, $O_2$ and air, and (ii.) a heterogeneous catalyst comprising a metal ion or a metalloid, or performing homogeneous catalysis in the presence of NaOH (in which case, usually no catalyst comprising a metal ion or a metalloid is required), to obtain at least one quinone and/or hydroquinone compound, wherein said compound is characterized by any of general Formula (VII), (VIII) and/or (IX):

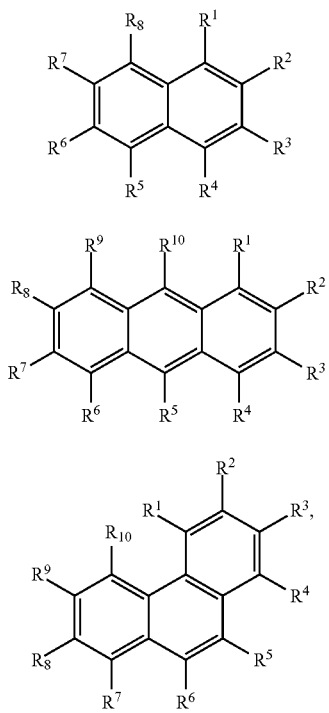

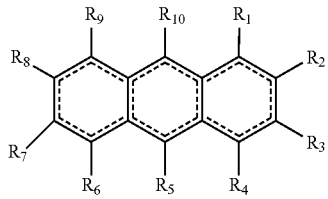

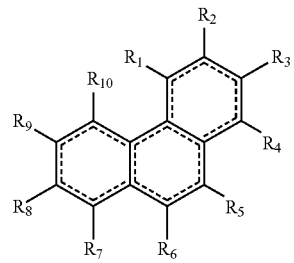

wherein each of $R^1$-$R^8$ with regard to Formula (VII) and/or each of $R_1$-$R^{10}$ with regard to Formula (VII) and (IX) is independently selected from H, optionally substituted $C_{1-6}$ alkyl, halogen, optionally substituted $C_{1-6}$alkoxy, amino, nitro, carboxyl, phosphoryl, phosphonyl;

wherein at least one of $R^8$ and $R^5$ or $R^1$ and $R^4$ of Formula (VII) are hydroxy or oxo, or at least one of $R^9$ and $R^6$, $R^{10}$ and $R^5$, or $R^1$ and $R^4$ of Formula (VIII) are hydroxy or oxo, or at least one of $R^{10}$ and $R^7$ or $R^1$ and $R^4$ of Formula (IX) are hydroxy or oxo.

For example, step (H) may provide a compound characterized by the following structure:

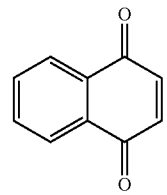 [SMILES: O=C1C=CC(=O)c2ccccc21]

wherein each of $R^1$-$R^8$ with regard to Formula (VII) and/or each of $R^1$-$R^{10}$ with regard to Formula (VIII) and (IX) is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo or carbonyl. wherein at least one of $R^8$ and $R^5$ or $R^1$ and $R^4$ of Formula (VII) are hydroxy or oxo, or at least one of $R^9$ and $R^6$, $R^{10}$ and $R^5$, or $R^1$ and $R^4$ of Formula (VIII) are hydroxy or oxo, or at least one of $R^{10}$ and $R^7$ or $R^1$ and $R^4$ of Formula (IX) are hydroxy or oxo.

Alternatively, said compound may be characterized by any of general Formula (VII), (VIII) and/or (IX):

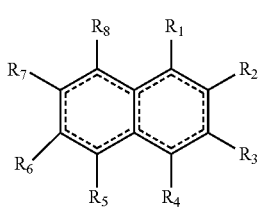

It is further preferred that the at least one quinone and/or hydroquinone compound, provided by step (F), (G), (H), (H.1), (H.2) or (H.1) and/or (I) is subjected to an isolation and/or purification step (J) to separate the at least one quinone and/or hydroquinone compound from residual compounds by suitable method, preferably by precipitation, recrystallization, distillation, sublimation, solid phase extraction or fluid-fluid phase extraction as generally known in the art, most preferably by precipitation.

Said at least one filtered quinone and/or hydroquinone typically is a redox active compound. A redox active compound is understood in the context of the present invention as a chemical compound, which may form a pair of an oxidizing and reducing agent, i.e. a redox pair, which are involved in a particular reaction. Thus, said compound is preferably suitable for any electrochemical application.

In a preferred embodiment of the second aspect of the present invention, the at least one quinone and/or hydroquinone compound is further modified by being subjected to a derivatization step (K), wherein preferably one or more hydrogen, hydroxy (OH—), carboxy, linear or branched, optionally substituted, $C_{1-6}$ alkyl (e.g. $CH_3$—), linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, halogen, amine, amino, amide, nitro, oxo, carbonyl, phosphoryl, phosphonyl, cyanide or sulfonyl ($SO_3H$—) groups (or other groups) are introduced into a compound according to any of Formulae (I) to (IX) at a position of the aryl structure other than those characterized by an oxo or hydroxyl group, wherein said group(s) is/are directly bound to the aryl structure or bound via an alkyl linker to the aryl structure, preferably via a methyl linker. $NO_2^-$ may be introduced but may be less preferred for stability reasons of the resulting compound.

In the context of the present invention, a monomeric aromatic lignin-derived compound substituted for instance with one or more $SO_3H$, OH and/or $CH_3$-groups may be provided as a material for a low potential electrolyte. Additionally, or alternatively, a monomeric aromatic lignin-derived substituted with one or more —$NO_2$-groups may provide a material for a high potential electrolyte.

The use of lignin as a starting material of the inventive method has the advantage that the compounds obtained from steps (F), (G), (H), (I) and (J) preferably already comprise $C_{1-6}$ alkoxy groups (in particular methoxy or ethoxy groups), which may confer further desired properties in particular when the target compounds are intended for use as redox active compounds. Such $C_{1-6}$ alkoxy groups could otherwise typically be introduced into precursor compounds under considerable (technological and/or financial) effort only. The compounds obtained from steps (F), (G), (H), (I) and (J) that are further modified in step (K) of the inventive method may thus advantageously carry $C_{1-6}$ alkoxy groups as substituents. The modification step (K) may then be employed to introduce further substituents of interest.

The modification reactions can be performed with benzoquinones, benzohydroquinones and their derivatives and naphthoquinones, naphthohydroquinones and their derivatives as starting materials as well as mixtures of the starting materials. Each starting material, intermediate or product can be transferred to its corresponding quinone or hydroquinone form via oxidation or reduction. Suitable oxidization agents may be selected from be air, oxygen or hydrogen peroxide, in combination with or without catalysts. The catalysts may be selected from metal based-catalysts (preferably comprising copper and aluminium), iodine, non-organic and organic acids or other quinones. Suitable reduction agents may be hydrogen, sodium dithionate, sodium borohydride, iron, tin(II)-chloride or zinc, in combination with or without catalysts, with hydrogen and sodium dithionate being preferred. The catalysts may be metal based, preferably palladium or nickel.

Quinones and hydroquinones can be modified or derivatized by substitution and addition reactions or rearrangements, preferably substitution reactions on hydroquinones and addition reactions on quinones (cf. reaction schemes 1 and 2). Substitution reactions include any reaction wherein a proton on the aromatic ring is exchanged by a different group, e.g. via an electrophile substitution. Suitable electrophiles may be selected from sulfur trioxide, aldehydes, ketones, esters, lactone, carboxylic acids, anhydrides, imine, carbon dioxide, chlorosulfonic acid, acyl halides, halogens, $NO_2$ and epoxides, preferably carbon dioxide, anhydrides, imines and acyl halides.

Addition reactions include any reaction that introduces a new group in the aromatic ring except for protons, preferably via a nucleophile addition on the aromatic ring with subsequent tautomeric rearrangement. Suitable nucleophiles include ammonia, amines, nitrogen containing heterocycles, thiols, alcohols, cyanides and azides, preferably amines, alcohols and nitrogen containing heterocycles.

Reactions can be performed step wise or in several steps in a one pot reaction. The modified target compounds may exhibit favorable redox properties rendering them useful in a variety of applications.

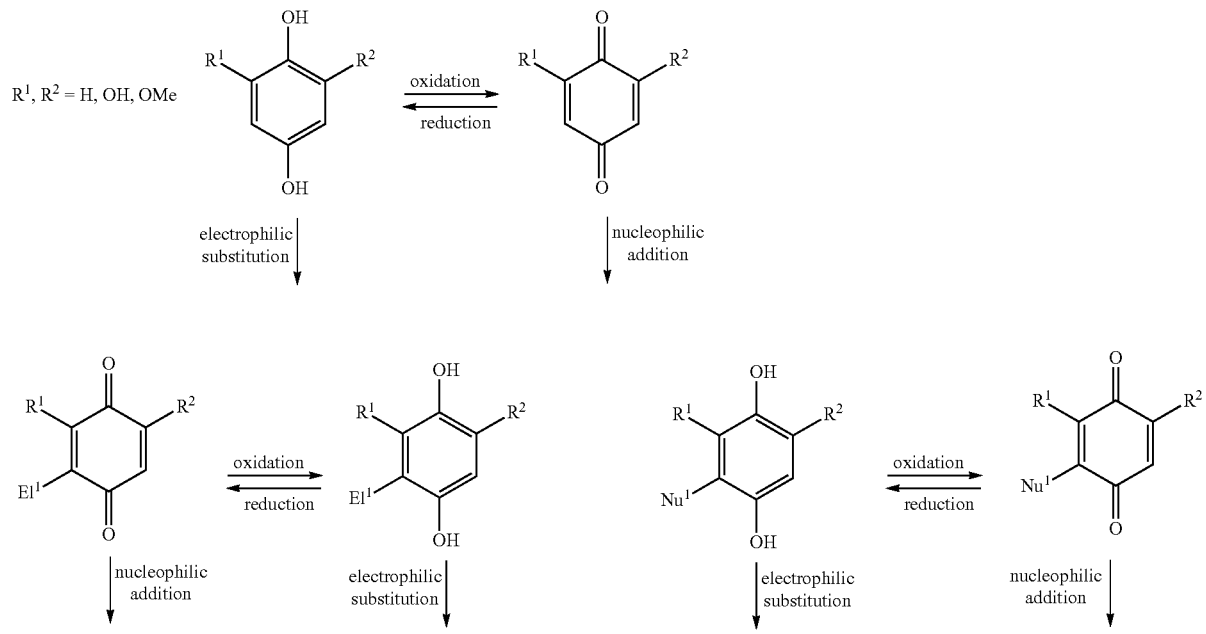

Scheme 1

-continued

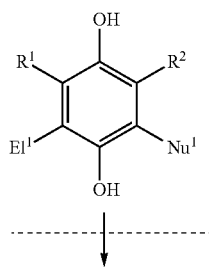 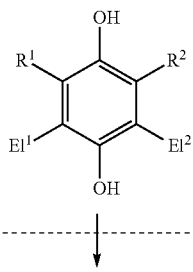 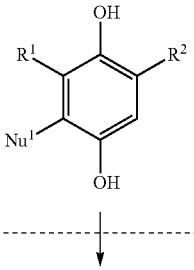 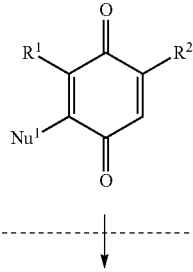

R¹/R² = H  ↓  ↓ Further reaction till full substitution  ↓  ↓

Scheme 2

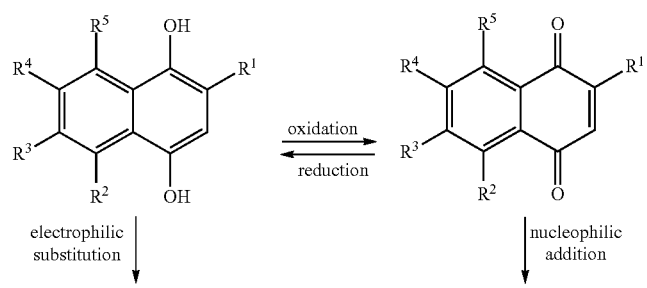

R¹ = H, OH, OMe
R², R³, R⁴, R⁵ = H, OH, OAlkyl, NR₂, NR¹R², NHR, SO₃H, quart N, Alkyl

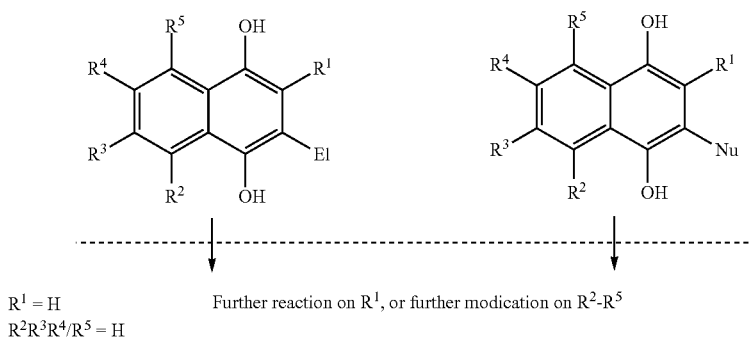

R¹ = H
R²R³R⁴/R⁵ = H

Further reaction on R¹, or further modication on R²-R⁵

Further substituents can be introduced into napthoquinones and napthohydroquinones after the modification reaction on R²-R⁵ (Scheme 2). Typical (further) substituents R²-R⁵ are hydrogen, methoxy, ethoxy, primary, secondary, tertiary and quaternary amines, carboxyalkyl, aminoalkyl, carboxylic acids, esters, amides, cyanides and alkyl-groups.

Anthaquinones and anthrahydroquinones can be modified by oxidation and reduction as described in the context of other (hydro-)quinones above. Subsequently, substituents can be introduced on R²-R¹⁰ in suitable substitution reactions, which typically do not involve electrophilic substitution.

Sulfonation of (hydro-)quinones (in particular benzo-, naphtho- and anthraquinones) is a modification reaction of particular interest in the context of the present invention.

In general, sulfonation may be carried out in the presence of concentrated aqueous sulfuric acid or oleum. Alternatively, sulfur trioxide may be mixed with inert gas, such as air, $N_2$ and/or $CO_2$, or complexed with a complexing agent such as pyridine, dioxane, $(CH_3)_3N$ or DMF. In general, sulfonation is preferably performed at higher temperatures due to increased yields. Therein, an increased temperature is understood to be at least 50° C., preferably 100° C. However, the temperature is not so high that the modified compound is prone to pyrolysis.

Separation of the sulfonated compound bay may subsequently be carried out, for example, by filtration or salting out as described herein.

Oxidized annulated compounds preferably are superb redox active compounds for versatile use. It is especially preferred that they may be produced from renewable sources and, at the same time, contribute to the valorization of otherwise by products from the pulping industry.

Modified low molecular weight aromatic lignin-derived compounds obtained from step (K) of the inventive method may preferably be characterized by any of general Formula (VII), (VIII), (IX) or (X):

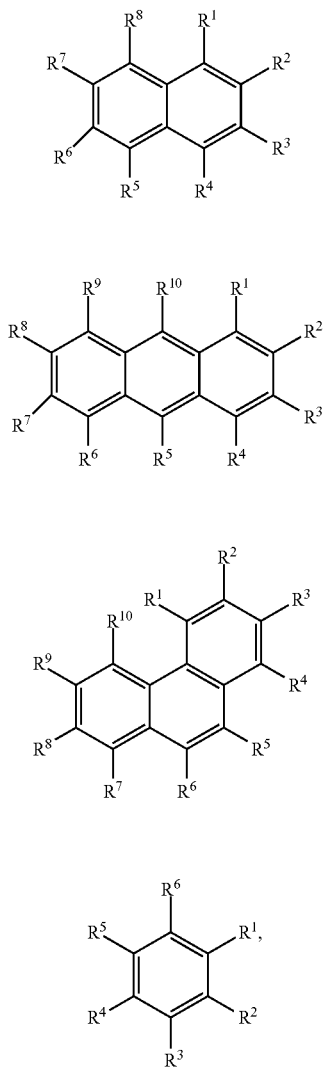

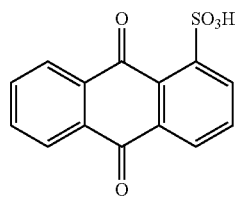

wherein each of $R^1$-$R^8$ with regard to Formula (VII) and/or each of $R^1$-$R^{10}$ with regard to Formula (VIII) and (IX) and/or each of $R^1$-$R^6$ with regard to Formula (X) is independently selected from hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, halogen, amine, amino, amide, nitro, oxo, carbonyl, phosphoryl, phosphonyl, cyanide and sulfonyl, wherein at least one of $R^8$ and $R^5$ or $R^1$ and $R^4$ of Formula (VII) are hydroxy or oxo, or at least one of $R^9$ and $R^6$, $R^{10}$ and $R^5$, or $R^1$ and $R^4$ of Formula (VIII) are hydroxy or oxo, or at least one of $R^{10}$ and $R^7$ or $R^1$ and $R^4$ of Formula (IX) are hydroxy or oxo, or at least one of $R^7$ and $R^{10}$, $R^5$ and $R^6$, or $R^6$ and $R^2$ are hydroxyl or oxo.

For example, step (K) of the method according to a second aspect of the present invention may preferably provide a compound characterized by the following structure:

A low molecular weight aromatic lignin-derived compound is provided, which is obtainable by a method according to the present invention. Preferably, said compound is of a structure as defined herein. The compound may be a low molecular weight aromatic lignin compound obtainable by step (F). Said compound may serve as a precursor for any of steps (G) to (K). Hence, the final compound is preferably a valuable, e.g. redox active compound resulting from a renewable lignocellulosic source.

In accordance with the above, an exemplary method according to the present invention may include the steps as described in the following. In a first step (A), a lignocellulosic material is provided. Said material may be in chopped form (e.g. as woodchips) and may for instance derived from wood of low silica and resin content, such as beech (or any other wood described above).

In a second step (B), the lignocellulosic material is subjected to a pulping process as described herein. Typically, said pulping process may be a Kraft process or a sulfite process as described above. In the Kraft process, the lignocellulosic material is typically wetted and pre-heated with steam, and cooked (e.g. under at least 4 bar for 3-5 hours at 150° C. or more, e.g. 170 to 180° C.) in an aqueous alkaline solution (e.g. sodium hydroxide) comprising a suitable Kraft pulping reactive agent (such as a sulfide salt, a sulfhydryl compound or salt, and a polysulfide salt, additionally, a sulfate salt may be added). Such a solution may be "white liquor" containing sodium hydroxide and sodium sulfide. The Kraft process typically yields "Kraft lignin" which may be further sulfonated to obtain "sulfonated Kraft lignin". However, other pulping processes as described herein may be applied as well. In particular, the sulfite process may be employed. In the sulfite process, lignocellulosic material is typically wetted and preheated with steam, and cooked (e.g. under at least 4 bar for 4-6 hours at 120° C. to 170° C., e.g. 130° C.-160° C.) in an aqueous, typically acidic solution of low pH (e.g. pH 1-5) comprising a sulfite or bisulfite agent.

The pulping process preferably disintegrates wood into its components lignin, cellulose and hemicellulose, which may be separated in a subsequent step.

In step (C) of the inventive method, the pulp is separated from the process stream, to provide at least one process stream that is substantially free from cellulose and comprises modified lignin-derived components, hemicellulose, and the like. Separation may typically be accomplished by blowing, sieving, filtration and one or more washing steps.

Subsequently, in step (D), modified lignin-derived components may be isolated from other components of the process stream(s), e.g. by ultra- and/or nanofiltration with suitable molecular weight cut-off values (such as about 5 kDa for ultrafiltration and 0.1-5 kDa for nanofiltration).

The isolated modified lignin-derived components are then subjected to chemical decomposition in step (E), e.g. by oxidative cracking (cracking and oxidizing) (although other chemical decomposition methods described herein are also applicable), to break or dissociate larger molecules into their smaller fragments by dissociation of covalent bonds of the larger molecule. Oxidative cracking (cracking and oxidizing) may be effected in the presence of a suitable oxidizing agent, such as air, and a suitable catalyst. The catalyst may be a homogenous catalyst, e.g. a metal salt comprising a metal ion such as Cu(II) or Fe(III), or comprising a metalloid component such as B(Ill), Si(IV) and Al(III). Chemical decomposition may be conducted at elevated temperatures (i.e. >30° C., e.g. 150° C.) but is typically performed at temperatures that do not induce pyrolysis of the treated materials (i.e. <350° C.).

In a further step (F), low molecular weight aromatic lignin-derived components are isolated from higher molecular weight aromatic lignin-derived components and/or other non-lignin-derived residual components, e.g. by ultra- or nanofiltration. The employed ultra- or nanofilters may have a molecular weight cut-off of 0.15 kDa to 1 kDa or less, eg. 0.5 kDa.

Isolation step (F) may further involve the purification of said low molecular weight aromatic lignin-derived components, e.g. by diafiltration or extraction, optionally followed by fractionated distillation.

Low molecular weight aromatic lignin-derived compounds may preferably be aromatic and include one or two (non-annulated) aromatic rings, optionally joined by an aliphatic linker. Exemplary low molecular weight aromatic lignin-derived compounds obtainable by the inventive method include phenolic derivatives of biphenyl, benzylalcohol, benzaldehydes and benzoic acid, preferably derivatives of p-hydroxy benzylalcohol, p-hydroxy benzaldehydes and p-hydroxy benzoic acid, or more preferably vanillin, guaiacol, eugenol, syringol, phenol, syringaldehyde, or derivatives thereof.

Monocyclic compounds may be subjected to a Friedel Crafts acylation (or another suitable annulation reaction) to produce annulated bi- or tricyclic compounds (or tetra- or pentacyclic, or even higher n-cyclic compounds) in step (G) of the inventive method. However it is also possible to subject the obtained compounds to annulation at a later stage of the process, e.g. after step (H).

The (optionally annulated) low molecular weight lignin-derived compounds obtained from isolation/purification step (F) or annulation step (G) of the inventive method may then be oxidized in a step (H) in the presence of an oxidizing agent, such as $H_2O_2$ or $O_2$, and a suitable catalyst. Useful catalysts in this context include, for instance, Co(II) complexes such as (pyr)Co(II)salen, Co(3-methoxysalen) and Co(N—N-Me salpr. The oxidation step (H) of the inventive method may preferably yield hydroquinone compounds (such as benzohydroquinones, napthohydroquinones or anthrahydroquinones).

Said hydroquinones may be subjected to a further oxidation step (I) in order to obtain the respective quinone compounds. Hydroquinone oxidation may preferably be perform end by an oxidant, optionally in the presence of a suitable heterogeneous catalyst such as CuOAlO(OH).

The inventive process may include at least one further isolation/purification step (J) after step (G), (H) and/or (I), which may involve extraction, precipitation and/or distillation.

Finally, the (isolated and/or purified) (hydro-)quinones obtained from step (H), (I) or (J) may be derivatized to introduce one or more functional groups of interest. Such reactions may involve oxidation, reduction, (optionally electrophilic) substitution, and/or nucleophilic addition reactions, as described herein. The introduced functional group may be selected from a variety of groups, depending on the desired use of the obtained compounds. For instance, $SO_3H$-groups may be of particular interest and may yield redox active compounds.

In a third aspect of the present invention, an assembly is provided for conducting steps (C) to (F), which are not part of a conventional pulp and/or paper manufacturing plant. With regard to step (C), pulp separation from the process stream originating from the pulping process (step (B)) is conducted as a core activity to obtain the target product of a conventional pulp and/or paper manufacturing plant. However, the separation of the process stream into at least two partial process streams as optionally devised in step (C) is not part of a known pulp and/or paper manufacturing plant. Hence, the assembly according to the present invention comprises (i) optionally a stream separator, (ii) an isolation unit, (iii) a decomposition unit, and (iv) a separation unit. Therein, the provision of the process stream in step (D) to provide partial process streams in step (D.2) is preferably conducted in a stream separation unit, comprising mechanical and/or pneumatic means known in the art. The isolation of the modified lignin may be conducted in an isolation unit, comprising, for example, means for conducting (ultra-) filtration, extraction and countercurrent flow.

In another preferred embodiment of the present invention, the (i) stream separator of the assembly facilitates that the substantially pulp-free process stream of step (C) is divided into at least two partial process streams. By means of the stream separator, the ratio of the at least two partial process streams may be controlled, which streams may be supplied to different further processing. Typically, the fraction of modified lignin-derived components of one of the partial process streams is not isolated. Instead the stream comprising the original content of modified lignin is forwarded to a combustion and recovery unit. Using some of the fraction of modified lignin-derived components as an internal energy fuel for the energy supply for the pulp and/or paper manufacturing plant. Additionally, residual reactive agents are regained, e.g. from the black or brown liquor or from organic solvents. These reactive agents are typically salts, which withstand temperatures of, for example, at least 500° C., or even at least 750° C., or even at least 1000° C. During combustion, e.g. sodium sulfate may be reduced to sodium sulfide by the organic carbon in the mixture, which may be reused in the pulping process. In contrast, the organic material, which serves as internal fuel, such as the modified lignin, hemicellulose, residual cellulose and/or fragments thereof, are burned at temperatures of, for example, at least 500° C., or even at least 750° C., or even at least 1000° C.

The combustion and recovery process is more frequently employed in plants operating according to the Kraft process. Therein, excess black liquor typically contains about 15% (w/w) solids and may be concentrated in a multiple effect evaporator. After said concentration, the black liquor is typically enriched to about 20-30% (w/w) solids. At such a concentration of solids, a naturally comprised soap called rosin soap rises to the surface and is skimmed off. The collected soap is further processed to tall oil. Removal of the soap improves the combustion operation. Soap-depleted black liquor with about 20-30% (w/w) solids is be called weak black liquor. It may then be further evaporated to 65% or even 80% solids, which may be called "heavy black liquor", and may be burnt in a recovery boiler to provide energy and to recover the inorganic chemicals for reuse in the pulping process. Concentrated black liquor is usually appreciated for its large heating value (about 12.000 to 13.000 Btu/dry Ib). The heat released from the combustion is used to generate high pressure and power. Therefore, the high pressure steam may be fed to turbogenerators, reducing the steam pressure for the plant use and generating electricity. Some of the heat released and part of the reducing value in black liquor is used to drive the pulp and/or paper production plant's reactive agent recovery operation.

Thus, the fraction of modified lignin-derived components of the process stream coming from step (B) of the inventive method is typically an important fuel for paper and pulp manufacturing plant as it contributes heavily to a pulp and/or paper production plant's energy self-sufficiency. Moreover, the pulp and paper industry traditionally has a highly efficient infrastructure for growth, harvesting, transport, and processing of forest materials. For example, Kraft operations are highly integrated and depend on the (modified) lignin fraction from wood as a fuel to operate the incredibly expensive chemical recovery boilers that are the heart of their operation. In the past, diverting this fuel source to other uses would have required the pulping operation to supplement its energy needs by purchasing natural gas or coal, potentially upsetting the plant's economics. Therefore, the Kraft process in contrast to the sulfite process essentially did not provide a source of lignin-derived raw material.

However, modern pulp and/or paper production plants, including such running under the Kraft process, become more and more energy efficient. Additionally, bark and wood residues may be burned in a separate power boiler to generate steam. Said overflow in energy sources available to a modern pulp and/or paper manufacturing plant may provide a sufficient "safety margin" to divert lignin-derived combustible material while the plant remains self-sufficient in terms of energy supply.

The "safety margin" of overflow modified lignin available form modern pulp and/or paper production plants may be even larger considering the fact that high solid contents in the concentrated (black) liquor have the typical drawback of resulting in higher viscosity and precipitation of solids in the ducts and the combustion and recovery unit. This precipitation leads to adverse plugging and fouling of equipment, which has to be preferably avoided. Thus, controlling the isolation of the fraction of modified lignin-derived components, e.g. also by means of the stream divider of the inventive assembly, and thereby reducing the modified lignin load in the process stream supplied to the combustion and recovery unit, may advantageously contribute to avoid such adverse plugging and fouling of equipment.

In this regard, the inventive assembly provides means to balance the needs for energy supply to the Kraft process on the one hand and the diverting of lignin and derivatives thereof on the other hand. First, the flexible control of the diverting means allows to direct exactly the share of the process stream to the generation of electricity and/or steam, which is actually needed to run the pulp and/or paper manufacturing plant. Thereby, modified lignin-derived components not required in combustion may entirely be directed to other uses such as the further processing of modified lignin according to the present invention. Therefore, less or even no modified lignin is wasted anymore as fuel in excess generation of electricity and/or steam. Second, any modified lignin or lignin-derived compound or fragment thereof, which does not yield the target low molecular weight aromatic lignin-derived compound may be recycled back to the process stream feeding the energy supply of the pulp and/or paper manufacturing plant. Third, as explained herein, pulp and/or paper manufacturing plants become more and more energy efficient, thus the required modified lignin supply for energy providing purposes is about to shrink. Alternatively, energy losses could be mediated by using forest residues and/or by transferring to black liquor gasification. In that scenario, the industry could continue to generate the power they need, but because of the higher efficiency of gas turbines, could also produce a separate syngas stream for the production of higher-value products.

For carrying out step (E), the assembly comprises a decomposition unit, providing means to sustain elevated temperature and/or pressure, and to provide the required reactants in solid, liquid and/or gaseous form, preferably in one reaction vessel only. Alternatively, the decomposition unit of the assembly provides a suitable electrochemical cell such as a flow cell.

For conducting step (F), the assembly comprises an isolation unit providing means for isolating low molecular weight aromatic lignin-derived compounds, such as monomers and dimers are used herein, from higher molecular weight lignin-derived components and/or other material involved in the inventive method. Preferably said means is an ultra- and/or nanofiltration unit or an extraction. All ducts and/or product and/or process stream contacting parts are preferably made from inert materials. The preferred details of said assembly are described herein with regard to the method, which is performed in said assembly. For example, valves and/or pumps or gravity assisting means may typically be employed to facilitate the required flow of the stream downwards to the next step of the inventive method.

It is even more preferred that said assembly for conducting the steps (C) to (K) further comprises (v) optionally an annulation unit, (vi) an oxidizing unit, (vii) optionally a derivatization unit and (viii) optionally a purification unit. Therein, typically step (G) is conducted in an annulation unit, step (H) and optionally (I), in an oxidizing unit, step (J) in a derivatizing unit and step (K) in a purification unit. The preferred requirements for such assembly units may be derived from the conditions and characteristics of the method steps described herein, which are performed in said assembly units.

Preferably, said assembly is directly connected to a conventional pulp and/or paper production plant. However, in an alternative embodiment, the apparatus is not directly associated or attached with the conventional pulp and/or paper manufacturing plant. Instead. The process stream originating from step (B), e.g. of a conventional pulp and/or paper manufacturing plant, is collected and then transferred to a distinct apparatus suitable to conduct the steps (C) to (F) and optionally (G) to (K). Yet, in the context of the present invention, a direct integration of the apparatus suitable to conduct the steps (C) to (F) and optionally (G) to (K) is preferred, as such direct integration provides for a flexible separation of the lignin-derived compounds in the process stream depending on the energy needs and further parameters of the pulp and/or paper manufacturing plant.

In a fifth aspect of the present invention, a method is provided for applying a pulp and/or paper manufacturing process using the pulping process by a plant, wherein the plant is equipped with an assembly according to the present invention. Accordingly, said method refers to modifying an existing pulp and/or paper manufacturing plant, working e.g. under the Kraft or sulfite process, wherein the plant is provided with the assembly according to the present invention. This may be of particular benefit, as an existing plant is thereby upgraded to provide potentially simultaneously (i) conventional pulp and/or paper, (ii) energy supply from lignin combustion to run the plant in a preferably self-sustaining manner, and (iii) intermediates of fine chemicals or fine chemicals such as redox active compounds based on the otherwise by-product of modified lignins. The such upgraded plant may be versatilely operated depending on actual demand for pulp, energy or fine chemical. Hence, this method significantly adds flexibility and appreciation to the existing pulp and/or paper manufacturing plant.

Any technical features disclosed thereby can be part of each and every embodiment of the invention. Additional definitions and explanations can be provided in the context of this disclosure.

The present invention as described in detail above should not to be understood to be limited to the particular methodologies, protocols and reagents described herein as these may vary. It is also to be understood that the terminology used herein is not intended to limit the scope of the present invention, which will be limited only by the appended claims. Unless defined otherwise, all technical and scientific terms used herein have the same meanings as commonly understood by one of ordinary skill in the art.

The herein described elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims, which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The examples shown in the following are merely illustrative and shall describe the present invention in a further way. These examples shall not be construed to limit the present invention thereto. The following preparations and examples are given to enable those skilled in the art to more clearly understand and to practice the present invention. The present invention, however, is not limited in scope by the exemplified embodiments, which are intended as illustrations of single aspects of the invention only, and methods, which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Preparation of Low Molecular Weight Aromatic Lignin-Derived Compounds by Cracking and Reduction by a Nickel Catalyst Reductive cracking (cracking and reducing) of a modified lignin-derived component according to step (E.2) of the inventive method may for example be carried out by means of a catalyst comprising nickel, e.g. supported on activated carbon (Ni/C). The catalysts are typically prepared by an incipient-wetness impregnation method and further treated by a carbothermal reduction method known in the art.

Herein, nickel nitrate(II) hexahydrate [$Ni(NO_3)_2 \cdot 6H_2O$] is used and optionally added into water in a beaker known in the art. The solution is then stirred, e.g. for at least 30 min, to prepare an impregnation stock solution. Activated carbon having a water absorption capacity of typically above 1.8 mL $g^{-1}$ is added into the solution and the beaker may then covered by a culture dish to keep the sample wet for a prescribed time, preferably more than 12 h, more preferably 24 h. The sample is then dried at a temperature above 80° C., e.g. 120° C. overnight. The actual reduction is carried out in a container such as a preferably horizontal furnace in a flow of inert gas such as $N_2$. The flow is, e.g., 10 mL $min^{-1}$ or more, preferably 30 mL $min^{-1}$ or more. The reduction temperature preferably reaches at least 400° C., preferably 450° C., e.g. over set time period such as at least 30 min, preferably at least 60 min. The temperature for conducting the reduction is maintained at 450° C. for at least 1 h, more preferably for at least 2 h. The Ni/SBA-15 catalysts are reduced at 550° C. for 2 h. The Ni/$Al_2O_3$ catalyst is reduced at 700° C. for 2 h. The metal loading for each nickel- and copper-based catalyst is 10% (w/w) relative to the support. Herein, birch sawdust serves as lignocellulosic material and is treated with the ethanol-benzene mixture (v/v ratio 1:2) for 12 h. The treated birch sawdust, solvent (m/v 1:20), and catalyst (w/w 20:1) are placed in an autoclave reactor. The reactor is sealed and purged with Ar 4 to 6 times to expel air. Then, the reducing reaction is conducted at 200° C. at a stirring speed of at least 300 rpm, preferably 500 rpm. When the desired reaction time (usually 2 to 10 h) is reached, the reactor is cooled to ambient temperature before sampling.

Typically, the reaction generates 4-propylguaiacol and 4-propylsyringol as major products, together with minor alkene-substituted 4-propylguaiacol and 4-propylsyringol, as determined by standard gas chromatography. The compounds are isolated according to step (F), preferably by extraction.

Example 2: Preparation of Monomeric Aromatic Lignin-Derived Molecules from Lignosulfonate of a Sulfite Process by Electrooxidation Lignosulfonate is provided by step (D) according to the present invention. Thereof, a 1 M aqueous NaOH solution is prepared, comprising 1% (W/W) lignosulfonate. Said solution is subjected to an electrooxidation according to step (E.3). Therein, the solution is employed as anolyte. A 1 M aqueous solution is employed as katalyte. A flow cell with a flow rate of 250 ml/min is used. Electrolysis is allowed to take place galvanostatically for 8 h applying current of 1 mA/cm². A typical resulting voltage is 1,4 V. The voltage curve typically is asymptotic and the solution changes preferably color from brown to dark brown.

Samples of the solution are taken every hour over a time span of 8 h and subsequently examined photometrically. Thereof, an absorption profile typical for ortho-benzoquinone is determined. Hence, a lower molecular weight aromatic lignin-derived compound, quinone compound, is prepared by said method.

Said compound is then isolated according to step (F) of the present invention. Therefore, said compound is extracted by dichloromethane and subsequently subjected to cycles of charging and discharging processes in a flow cell. The voltage curve shows that the compound is redox active, which may be reversibly electrolyzed.

Example 3: Preparation of an Annulated Quinone Compound by a Friedel-Crafts Acylation Vanillin as a low molecular weight aromatic lignin-derived compound is provided by step (F) according to the present invention. Said compound is further annulated according to step (G) and oxidized according to step (H) according to the present invention in five steps as follows:

(i) Synthesis of 4-(benzyloxy)-3-methoxybenzaldehyde (2)

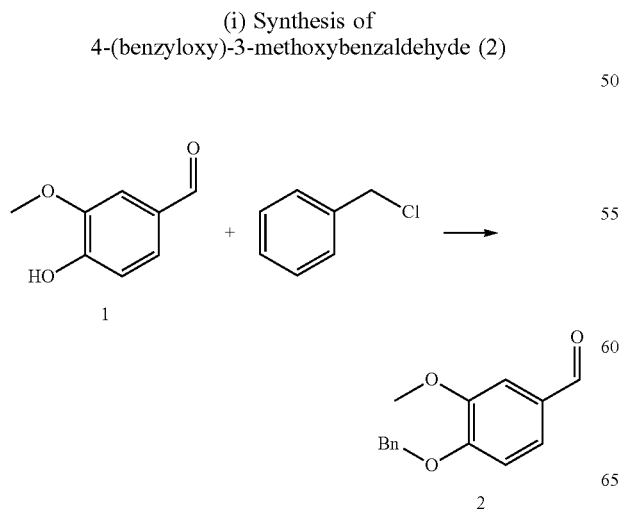

-continued

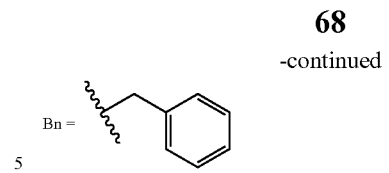

Vanillin (1) (1.0 eq.) and benzyl chloride (1.2 eq.) are dissolved in N,N-dimethylformamide and potassium iodine (0.5 mol %) is added. Afterwards potassium carbonate is added and the reaction is stirred above 60° C., preferably between 60 to 120° C. for at least 1 h, preferably 1 to 8 h. After completion of the reaction, the solution is diluted with distilled water and extracted with an appropriate solvent. The organic phase is washed with brine and the product is then isolated from the organic phase.

(ii) Synthesis of 4-(benzyloxy)-3-methoxybenzoic acid (3)

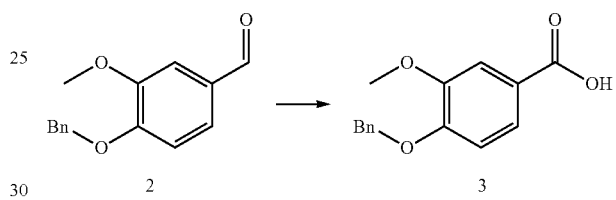

A mixture of 1,2-dimethoxyethane and potassium hydroxide (5 to 20 eq.) is purged with oxygen and the calculated amount of isolated product 2 (1.0 eq.) is added. After the absorption of oxygen ceases, the mixture is diluted with distilled water and neutral organic products are extracted with an appropriate solvent. The aqueous layer is acidified and the acidic organic products are extracted with an appropriate solvent. Product 3 is isolated from the organic layer.

(iii) Synthesis of 4-(benzyloxy)-3-methoxybenzoyl chloride (4)

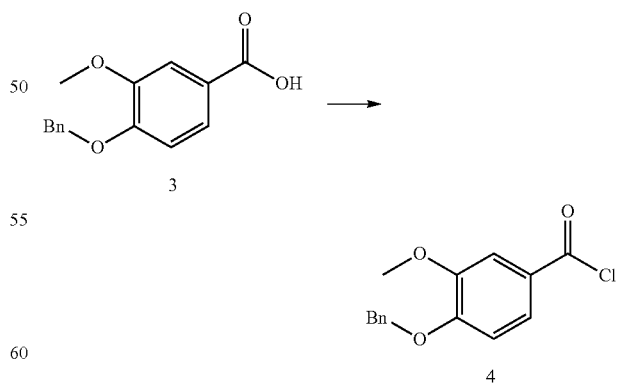

Isolated product 3 (1.0 eq.) is dissolved in thionyl chloride (5-20 eq.) and the mixture is stirred at 60 to 120° C. for 1 to 8 h. After completion of the reaction excess thionyl chloride is evaporated to yield desired acyl chloride 4.

(iv) Synthesis of Anthraquinones (5-7)

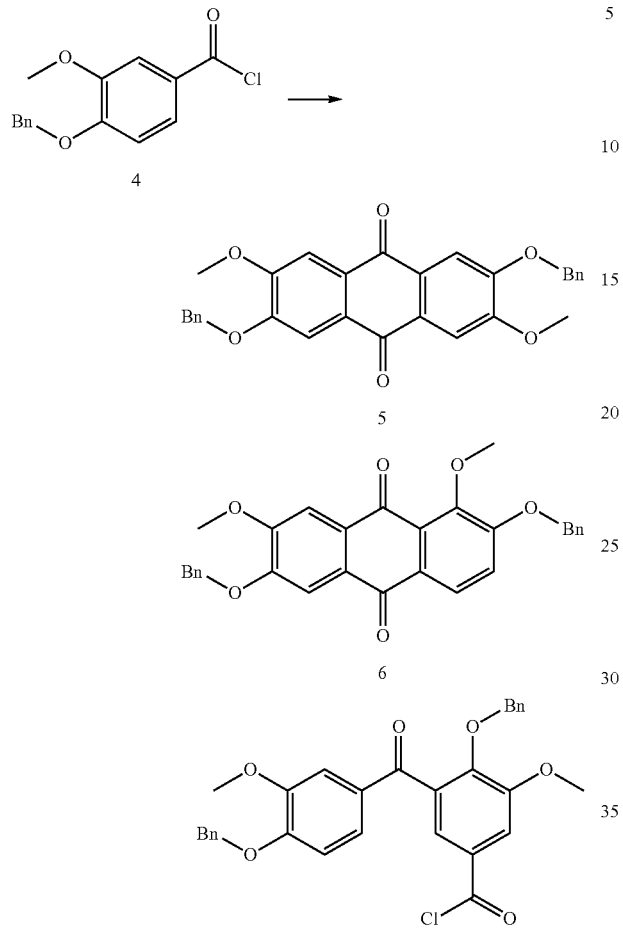

Aluminiumtrichloride (0.1 eq.) is added to the crude acyl chloride 4 and the mixture is stirred for 30 to 300 min at −20 to 60° C. After completion of the reaction the mixture is carefully quenched with bicarb solution. The product is extracted with an appropriate solvent and the organic layer is washed with brine. The product is then isolated from the organic phase.

(v) Synthesis of 2,6-dihydroxy-3,7-dimethoxyanthracene-9,10-dione 8 and 2,6-dihydroxy-1,7-dimethoxyanthracene-9,10-dione 9

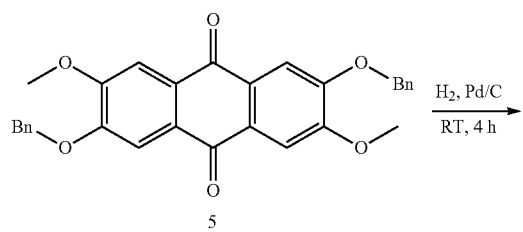

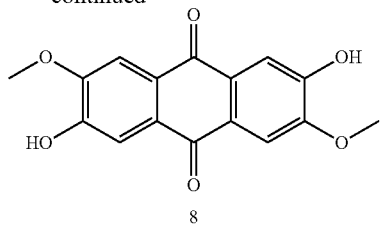

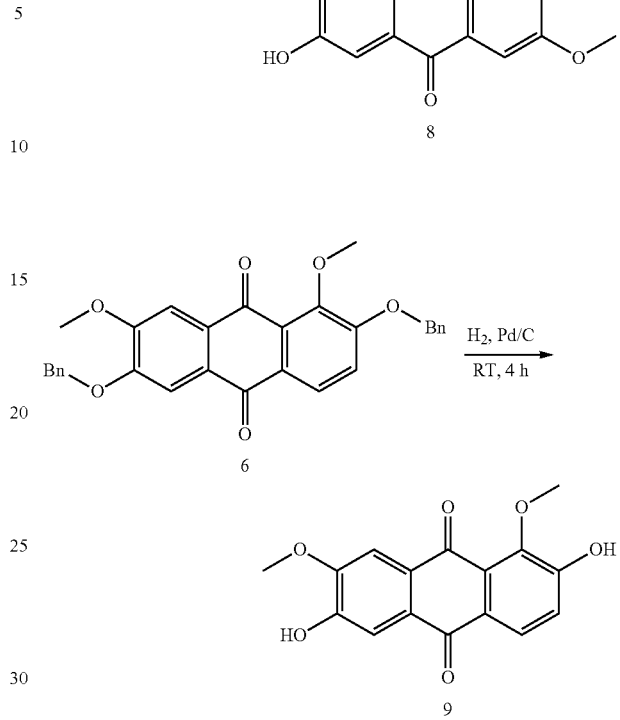

Anthraquinone 5 or 6 are dissolved in ethyl acetate, methanol or ethanol and palladium on charcoal (1 to 30 weight %) is added. The mixture is stirred at room temperature under hydrogen atmosphere (1-10 bar). The catalyst is filtered off and the product (9) is isolated from the mixture.

The product is then characterized by spectrographic means, and provided as redox active compound according to the present invention.

Example 4: Derivatization of (Hydro-)quinones

Example 4.1 Reduction of Dimethoxy Benzoquinone

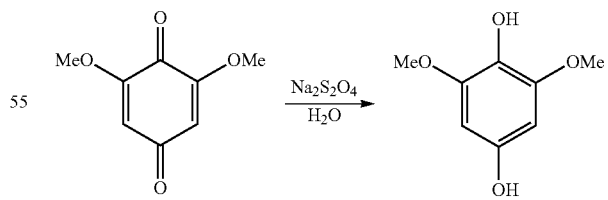

23.2 g of sodium dithionite (0.134 mol, 1.32 eq.) was added to the suspension of 17.0 g (0.101 mol, 1.0 eq.) 2,6-dimethoxycyclohexa-2,5-diene-1,4-dione in 100 mL $H_2O$. After 2 h stirring at room temperature the precipitate was filtered off and dried in the air to give 15.85 g (0.093 mol, 92% yield) of 2,6-dimethoxybenzene-1,4-diol as a white solid.

Example 4.2: Oxidation of Methoxy Benzohydroquinone

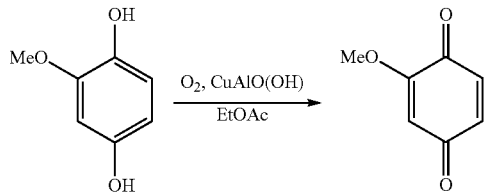 [SMILES: "EtOAc" ; COc1cc(O)ccc1O ; COC1=CC(=O)C=CC1=O]

1.4 g of catalyst Cu/AlO(OH) was added to a solution of 8.2 g (0.059 mol) 2-methoxy-1,4-dihydroxybenzene in 250 mL ethyl acetate, and the reaction mixture was stirred at room temperature for 147 h under an $O_2$ atmosphere. After the conversion determined by HPLC reached 99%, the reaction mixture was filtered, and the recovered catalyst was washed with ethyl acetate (100 mL×3). The filtrate was collected and solvent was removed in vacuo to give 7.66 g (0.055 mol, 95% yield) of 2-methoxycyclohexa-2,5-diene-1,4-dione as a yellow-brownish solid.

Example 4.3: Acetylation of Methoxy Benzohydroquinone 8.24 g (0.059 mol, 1.0 eq.) of 2-methoxybenzene-1,4-diol was weighed into a 250 mL reaction flask equipped with a reflux condenser. 60 mL of dichloroethane and 15 mL (0.159 mol, 2.7 eq.) of acetic anhydride were added. 12 ml (0.096 mol, 1.63 eq.) of boron trifluoride ether solution was then slowly added at room temperature with stirring. The reaction mixture was heated to 90° C. for 20 hours. The mixture was cooled to 60° C., 30 mL $H_2O$ was added followed by 10 mL HCl (6 M). The resulting mixture was heated to 100° C. for 30 min, cooled down and extracted with ethyl acetate (150 mL×3). The combined extracts were washed sequentially with $H_2O$ (100 mL), saturated sodium bicarbonate (100 mL) and $H_2O$ (100 mL) and then dried with anhydrous sodium sulfate. The solvent was removed in vacuo to give a brown solid residue, which was washed with methanol to give 7.49 g (0.041 mol, 70% yield) of 1-(2,5-dihydroxy-4-methoxyphenyl)ethan-1-one as a beige solid.

Example 4.4 Addition of Isonicotinic Acid to Benzoquinone 2.16 g (0.02 mol, 1.0 eq.) of p-benzoquinone was suspended in 6.4 mL of acetic acid. 2.46 g (0.02 mol, 1.0 eq.) of nicotinic acid was added and the mixture was stirred for 2 h at rt. The resulting dark mixture was diluted with 3 mL of water and treated with 6.6 mL of HCl (6 M). On cooling, solid precipitated which was filtered off and dried overnight at 60° C. to give 3.13 g (0.012 mol, 59% yield) of 3-carboxy-1-(2,5-dihydroxyphenyl)pyridin-1-ium chloride as an yellow solid.

Example 4.5 Sulfonation of Anthraquinone

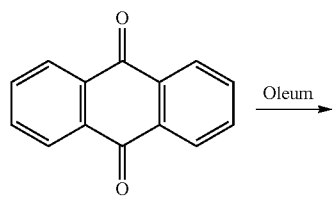

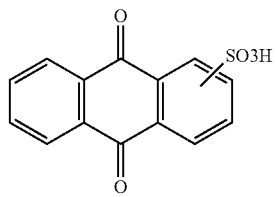

A solution of anthraquinone was heated (180° C.) in a solution of 20%-40% $SO_3$ in concentrated sulfuric acid (oleum), resulting in a mixture of sulfonated anthraquinones. The crude mixture was poured onto ice and partially neutralized with calcium hydroxide. Subsequently, the mixture was filtrated and concentrated to yield the final product.

Example 4.6: Sulfonation of hydroquinone (1,4-Dihydroxybenzene)

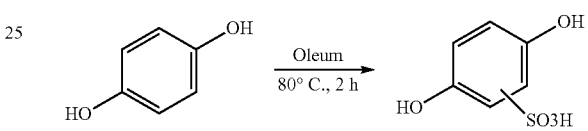

A solution of hydroquinone was heated (80° C.) in a solution of 20%-40% $SO_3$ in concentrated sulfuric acid (oleum), resulting in a mixture of sulfonated hydroquinones. The crude mixture was poured onto ice and partially neutralized with calcium hydroxide. Subsequently, the mixture was filtrated and concentrated to yield the final product.

Example 4.7: Sulfonation of 1,4-Dihydroxy-2,6-dimethoxybenzene

A solution of hydroquinone was heated (80° C.) in a solution of 20%-35% $SO_3$ in concentrated

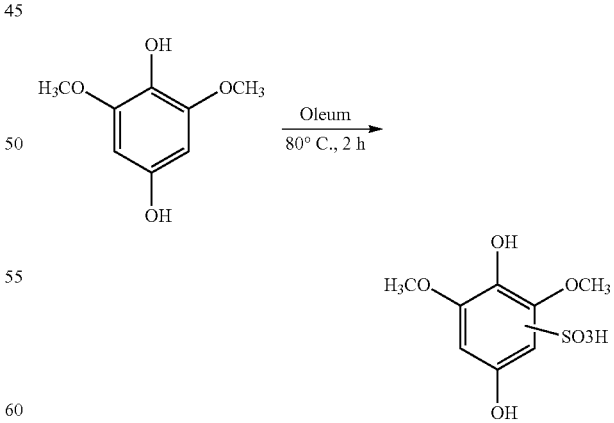

sulfuric acid (oleum), resulting in a mixture of sulfonated 1,4-dihydroxy-2,6-dimethoxybenzenes. The crude mixture was poured onto ice and partially neutralized with calcium hydroxide. Subsequently, the mixture was filtrated and concentrated to yield the final product.

Example 4.8: Sulfonation of 2-Methoxyhydroquinone

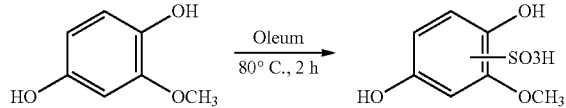

A solution of 2-methoxyhydroquinone was heated (80° C.) in a solution of 20%-40% $SO_3$ in concentrated sulfuric acid (oleum), resulting in a mixture of sulfonated 2-methoxyhydroquinones. The crude mixture was poured onto ice and partially neutralized with calcium hydroxide. Subsequently, the mixture was filtered and concentrated to yield the final product.

The invention claimed is:

1. A method for producing at least one low molecular weight aromatic lignin-derived compound, the method comprising the steps of
   (A) providing optionally chopped lignocellulosic material;
   (B) subjecting the lignocellulosic material to a pulping process;
   (C) separating cellulose obtained in step (B) in a pulp separating step from the process stream obtainable from step (B), to provide a substantially cellulose-free process stream, wherein the process stream comprises modified lignin-derived components, hemicellulose and/or fragments thereof; wherein the process stream is provided as one single process stream or as at least two partial process streams;
   (D) isolating a fraction of modified lignin-derived components being comprised
      (D.1) in the process stream of step (C) or,
      (D.2) in at least one of the at least two partial process streams in step (C)
      from either of these process streams;
   (E) subjecting the fraction of modified lignin-derived components of step (D) to a chemical decomposition step, wherein the chemical decomposition step comprises
      (E.1) oxidative cracking (cracking and oxidizing) of the modified lignin components in the presence of a heterogenous or homogeneous catalyst comprising a metal ion or a metalloid component;
      (E.2) reductive cracking (cracking and reducing) of the modified lignin components in the presence of a heterogeneous or homogeneous catalyst comprising a metal ion or metalloid component; or
      (E.3) subjecting the modified lignin components to electro-oxidation in alkaline or acidic solution;
   (F) subjecting resulting modified lignin-derived products obtained in step (E) to an isolation and optionally purification step, wherein low molecular weight aromatic lignin-derived compounds are isolated from higher molecular weight aromatic lignin-derived components and/or other non-lignin-derived residual components and optionally purified, and
   wherein the at least one low molecular weight aromatic lignin-derived compound provided by step (F) comprises one aromatic ring and is further processed in a step (G), wherein said low molecular weight aromatic lignin-derived compound comprising one aromatic ring is subjected to an annulation reaction, wherein the annulation reaction product is a low molecular weight aromatic bi- or tricyclic annulated aromatic lignin-derived compound, wherein said compound is characterized by Formula (II), (III) or (IV)

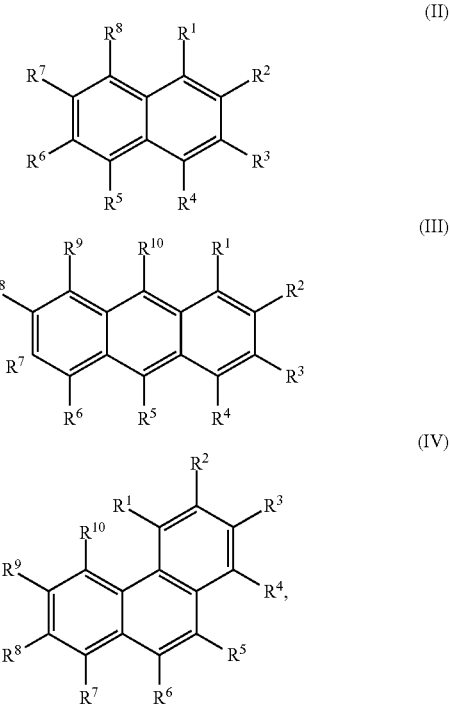

wherein
   each of $R^2$, $R^3$, $R^5$-$R^8$ of Formula (II) is independently selected from the group consisting of hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo and carbonyl; and optionally at least one of $R^2$, $R^3$, $R^5$-$R^8$ is hydroxy or $C_{1-3}$ alkoxy,
   $R^1$ and $R^4$ of Formula (II) is/are selected from the group consisting of hydrogen, hydroxy, linear or branched, optionally substituted, $C_{1-6}$ carboxyl, linear or branched, optionally substituted, $C_{1-6}$ aldehyde, and linear or branched, optionally substituted, $C_{1-6}$ alcohol,
   each of $R^1$-$R^{10}$ of Formula (III) is independently selected from the group consisting of hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo and carbonyl; and optionally at least one of $R^2$, $R^4$, $R^5$, $R^6$ and $R^8$ is hydroxy or $C_{1-3}$ alkoxy,
   each of $R^2$, $R^3$ and $R^7$-$R^{10}$ of Formula (IV) is independently selected from the group consisting of hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo and carbonyl; and optionally at least one of $R^2$, $R^3$ and $R^7$-$R^{10}$ is hydroxy or $C_{1-3}$ alkoxy, and $R^1$, $R^4$, $R^5$ and $R^6$ of Formula (IV) is selected from the group consisting of hydrogen, hydroxy, linear or branched, optionally substituted $C_{1-6}$ carboxyl, linear or branched, optionally substituted, $C_{1-6}$ aldehyde, and linear or branched, optionally substituted, $C_{1-6}$ alcohol.

2. The method of claim 1, wherein separation of step (C) is carried out by blowing, sieving, centrifugation, filtration and/or washing, or any combination thereof.

3. The method of claim 1, wherein isolation of step (D) is carried out by extraction, countercurrent flow, stripping, ion-exchange, precipitation by a di- or multivalent cation, precipitation by $CO_2$ in acidic solution, filtration or any combination thereof.

4. The method of claim 1, wherein in step (E.2) reductive cracking (cracking and reducing) of the modified lignin-derived components is carried out in the presence of a reducing agent and a heterogeneous catalyst comprising a metal selected from nickel, platinum, palladium, ruthenium, rhenium and gold.

5. The method of claim 4, wherein in step (E.2) reductive cracking (cracking and reducing) of the modified lignin-derived components is carried out on the surface of a support material selected from the group consisting of active carbon, silica, titaniumoxide and aluminumoxide.

6. The method of claim 4, wherein the reducing agent is hydrogen or a hydrogen donating alcohol.

7. The method of claim 4, wherein the heterogeneous catalyst comprises a metal selected from the group consisting of nickel and ruthenium, and the heterogeneous catalyst is optionally supported on activated carbon.

8. The method of claim 7, wherein the metal is nickel and the reductive cracking is carried out in an alcoholic solvent.

9. The method of claim 7, wherein the metal is ruthenium and the reductive cracking is carried out in an organic solvent.

10. The method of claim 1, wherein in step (E.3) electrooxidation is carried out galvanostatically and optionally at a pH from pH 1 to 14.

11. The method of claim 1, wherein isolation step (D) and/or isolation step (F) comprises filtration and/or extraction.

12. The method of claim 11, wherein the filtration is carried out in a ultrafiltration and/or nanofiltration cell comprising at least one molecular weight cut-off unit, wherein the at least one molecular weight cut-off unit has a cut-off level of 0.5 kDa to 2 kDa for step (D), and 1 kDa to 1.5 kDa for step (F).

13. The method according to claim 1, wherein the annulation reaction is a Friedel Crafts acylation.

14. The method of claim 1, wherein the low molecular weight aromatic bi- or tricyclic annulated compound provided by step (G) is further modified in a step (H) by oxidizing the at least one low molecular weight aromatic bi- or tricyclic annulated compound in the presence of (i.) an oxidizing agent selected from the group consisting of $H_2O_2$, $O_2$ and air, and (ii.) a heterogeneous or homogeneous catalyst optionally comprising a metal ion or a metalloid component, to provide at least one quinone and/or hydroquinone compound, wherein said compound corresponds in structure to any of Formula (VII), (VIII) and/or (IX):

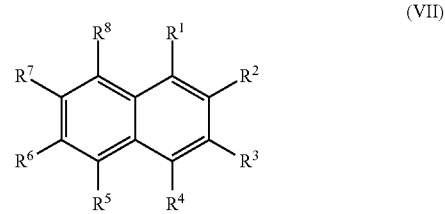

(VII)

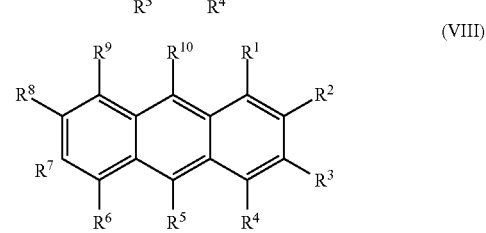

(VIII)

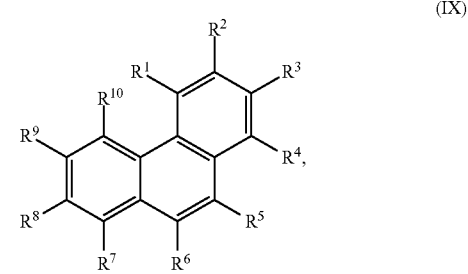

(IX)

wherein each of $R^1$-$R^8$ with regard to Formula (VII) and/or each of $R^1$-$R^{10}$ with regard to Formula (VII) and (IX) is independently selected from the group consisting of hydrogen, hydroxy, carboxy, linear or branched, optionally substituted, $C_{1-6}$ alkyl, linear or branched, optionally substituted, $C_{1-6}$ alkenyl, linear or branched, optionally substituted, $C_{1-6}$ alcohol, linear or branched, optionally substituted, $C_{1-6}$ aminoalkyl, linear or branched, optionally substituted, $C_{1-6}$ carboxyalkyl, linear or branched, optionally substituted, $C_{1-6}$ alkoxy, linear or branched, optionally substituted, $C_{1-6}$ aldehyde, ester, oxo and carbonyl, wherein at least one of $R^8$ and $R^5$ or $R^1$ and $R^4$ of Formula (VII) are hydroxy or oxo, or at least one of $R^9$ and $R^6$, $R^{10}$ and $R^5$, or $R^1$ and $R^4$ of Formula (VIII) are hydroxy or oxo, or at least one of $R^{10}$ and $R^7$ or $R^1$ and $R^4$ of Formula (IX) are hydroxy or oxo.

15. The method of claim 14, wherein the at least one quinone and/or hydroquinone compound is anthraquinone.

16. The method of claim 14, wherein the at least one quinone and/or hydroquinone compound is

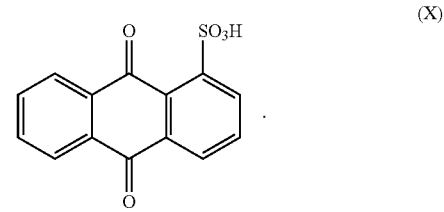 [SMILES: O=C1c2ccccc2C(=O)c2c1cccc2S(=O)(=O)O]

(X)

17. The method of claim 1, wherein in step (E.1) oxidative cracking (cracking and oxidizing) of the modified lignin-derived components is carried out in the presence of an oxidizing agent and a heterogeneous or homogeneous catalyst comprising
- a. a metal ion selected from Co(II), Cu(II) and Fe(III); or
- b. a metalloid component selected from B(III), Si(IV) and Al(III);

optionally at a temperature of 30-400° C.

18. The method of claim 1, wherein in step (E.1) the homogeneous catalyst is selected from the group consisting of a salt, a coordination complex, a zeolite and a polyoxometalate comprising a metal ion selected from Co(II), Cu(II) and Fe(III).

19. The method of claim 17, wherein step (B) is carried out according to the acidic sulfite process (B.2) of step (B) and/or wherein step (E) is carried out in the presence of a catalyst according to step (E.1).

20. The method of claim 1, wherein step (B) comprises a process selected from (B.1) a Kraft process comprising the steps of
- (a) optionally pre-steaming the optionally chopped lignocellulosic material, wherein the preferably chopped lignocellulosic material is wetted and preheated with steam,
- (b) adding the optionally chopped lignocellulosic material to an aqueous alkaline solution comprising a Kraft pulping reactive agent selected from the group consisting of a sulfide agent, a sulfhydryl agent, a polysulfide agent and a sulfate salt,
- (c) cooking the optionally chopped lignocellulosic material in said aqueous alkaline solution, and
- (d) optionally conducting sulfonation in the presence of a sulfuric acid solution or sulfur trioxide;

or (B.2) a sulfite process comprising the steps of
- (a) optionally pre-steaming the optionally chopped lignocellulosic material, wherein the optionally chopped lignocellulosic material is wetted and preheated with steam,
- (b) adding optionally chopped lignocellulosic material to an aqueous, optionally acidic solution comprising a sulfite or bisulfite agent, and
- (c) cooking the optionally chopped lignocellulosic material in said aqueous optionally acidic solution.

21. The method of claim 20,
wherein the pH of the aqueous alkaline solution in sub-step (b) of step (B.1) is >10 and/or the temperature of the aqueous alkaline solution in sub-step (b) of step (B.1) is less than 100° C.;

or wherein the pH of the aqueous optionally acidic solution in sub-step (b) of step (B.2) is 1 to 5 and/or the temperature of the aqueous optionally acidic solution in sub-step (b) of step (B.2) is less than 100° C.

22. The method of claim 20,
wherein the pH of the aqueous alkaline solution in sub-step (b) of step (B.1) is >10 and/or the temperature of the aqueous alkaline solution in sub-step (b) of step (B.1) is less than 100° C.;

or wherein the pH of the aqueous, optionally acidic, solution in sub-step (b) of step (B.2) is 1 to 5 and/or the temperature of the aqueous, optionally acidic, solution in sub-step (b) of step (B.2) is less than 100° C.

23. The method of claim 20,
wherein cooking in sub-step (c) of step (B.1) is carried out in a pressurized vessel for at least 2 hours and optionally at a temperature of at least 150° C.;

or wherein cooking in sub-step (c) of step (B.2) is carried out in a pressurized vessel for at least 3 hours at a temperature of at least 120° C.

24. The method of claim 20, wherein sub-step (c) of the Kraft process (B.1) is carried out for 2 to 24 hours, or wherein sub-step (c) of the sulfite process (B.2) is carried out for 4 to 24 hours.

25. The method of claim 20,
wherein Kraft process sub-step (c) of step (B.1) is carried out at a temperature of 150 to 190° C., or wherein sulfite process sub-step (c) of step (B.2) is carried out at a temperature of 120 to 170° C.

26. The method of claim 20, wherein sub-step (c) of step (B.1) or (B.2) is carried out at a pressure of at least 4 bar in the pressurized vessel.

27. The method of claim 20, wherein in sub-step (c) of step (B.1) or (B.2) is carried out in a batch mode or in a continuous mode.

* * * * *

UNITED STATES PATENT AND TRADEMARK OFFICE
CERTIFICATE OF CORRECTION

| | |
|---|---|
| PATENT NO. | : 11,225,756 B2 |
| APPLICATION NO. | : 16/091437 |
| DATED | : January 18, 2022 |
| INVENTOR(S) | : Krawczyk et al. |

It is certified that error appears in the above-identified patent and that said Letters Patent is hereby corrected as shown below:

In the Claims

Column 78, Line 11, cancel the text beginning with "22. The method of" to and ending "less than 100° C." in Column 78, Line 20, and insert the following claim:
--22. The method of claim 20,
wherein the sulfide and sulfate agent added according to sub-step (b) of step (B.1) is a salt with a counter cation selected from the group consisting of sodium, calcium, magnesium and ammonium; or
wherein the sulfite or bisulfite agent added according to sub-step (b) of step (B.2) is a salt with a counter cation selected from the group consisting of sodium, calcium, magnesium and ammonium.--

Signed and Sealed this
Nineteenth Day of April, 2022

*Katherine Kelly Vidal*

Katherine Kelly Vidal
*Director of the United States Patent and Trademark Office*